US010006027B2

(12) United States Patent
Bennett et al.

(10) Patent No.: US 10,006,027 B2
(45) Date of Patent: Jun. 26, 2018

(54) METHODS FOR MODULATING ATAXIN 2 EXPRESSION

(71) Applicants:Ionis Pharmaceuticals, Inc., Carlsbad, CA (US); University of Utah Research Foundation, Salt Lake City, UT (US)

(72) Inventors: C. Frank Bennett, Carlsbad, CA (US); Susan M. Freier, San Diego, CA (US); Stefan M. Pulst, Salt Lake City, UT (US); Daniel R. Scoles, Salt Lake City, UT (US); Gene Hung, San Diego, CA (US)

(73) Assignees: Ionis Pharmaceuticals, Inc., Carlsbad, CA (US); University of Utah Reseach Foundation, Salt Lake City, UT (US)

( * ) Notice: Subject to any disclaimer, the term of this patent is extended or adjusted under 35 U.S.C. 154(b) by 0 days. days.

(21) Appl. No.: 15/127,352

(22) PCT Filed: Mar. 19, 2015

(86) PCT No.: PCT/US2015/021607
§ 371 (c)(1),
(2) Date: Sep. 19, 2016

(87) PCT Pub. No.: WO2015/143245
PCT Pub. Date: Sep. 24, 2015

(65) Prior Publication Data
US 2017/0175113 A1    Jun. 22, 2017

Related U.S. Application Data

(60) Provisional application No. 61/955,704, filed on Mar. 19, 2014, provisional application No. 61/982,124, filed on Apr. 21, 2014.

(51) Int. Cl.
*C07H 21/02* (2006.01)
*C07H 21/04* (2006.01)
*A61K 31/70* (2006.01)
*C12N 15/113* (2010.01)

(52) U.S. Cl.
CPC ........ *C12N 15/113* (2013.01); *C12N 2310/11* (2013.01); *C12N 2310/14* (2013.01); *C12N 2310/141* (2013.01); *C12N 2310/315* (2013.01); *C12N 2310/317* (2013.01); *C12N 2310/321* (2013.01); *C12N 2310/323* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |

(Continued)

FOREIGN PATENT DOCUMENTS

| EP | 0878543 | 11/1998 |
|---|---|---|
| EP | 2399611 A2 | 12/2011 |

(Continued)

OTHER PUBLICATIONS

Bezprozvanny et al., "Therapeutic prospects for spinocerebellar ataxia type 2 and 3." Drugs Future (2009) 34(12):1-17.

(Continued)

*Primary Examiner* — Sean McGarry
(74) *Attorney, Agent, or Firm* — McNeill Baur PLLC

(57) ABSTRACT

Disclosed herein are methods for decreasing Ataxin 2 mRNA and protein expression. Such methods are useful to treat, prevent, or ameliorate Ataxin 2 associated diseases, disorders, and conditions. Such Ataxin 2 associated diseases include spinocerebellar ataxia type 2 (SCA2), amyotrophic lateral sclerosis (ALS), and parkinsonism. Provided are methods for reducing expression of Ataxin 2 (ATXN2) mRNA and protein in an animal. Such methods are useful to treat, prevent, or ameliorate neurodegenerative diseases, including spinocerebellar ataxia type 2 (SCA2), amyotrophic lateral sclerosis (ALS), and parkinsonism by inhibiting expression of Ataxin 2 in an animal.

30 Claims, No Drawings

(56) References Cited

U.S. PATENT DOCUMENTS

| | | |
|---|---|---|
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehter et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,673,535 B1 | 1/2004 | Pulst |
| 6,770,748 B2 | 8/2004 | Imanishi et al. |
| 6,844,431 B1 | 1/2005 | Pulst |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,888,497 B2 | 2/2011 | Bentwich et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,501,805 B2 | 4/2013 | Seth et al. |
| 8,440,803 B2 | 5/2013 | Swayze et al. |
| 8,530,640 B2 | 9/2013 | Seth et al. |
| 8,546,556 B2 | 10/2013 | Seth et al. |
| RE44,779 E | 2/2014 | Imanishi et al. |
| 8,728,736 B2 | 5/2014 | Leamon et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2004/0220132 A1* | 11/2004 | Kaemmerer ......... A61K 9/0085 514/44 A |
| 2005/0100885 A1 | 5/2005 | Crooke et al. |
| 2005/0130923 A1 | 6/2005 | Bhat et al. |
| 2005/0209178 A1 | 9/2005 | Pulst |
| 2005/0244851 A1 | 11/2005 | Blume et al. |
| 2005/0255487 A1 | 11/2005 | Khvorova et al. |

(56) References Cited

U.S. PATENT DOCUMENTS

| | | |
|---|---|---|
| 2006/0148740 A1 | 7/2006 | Platenburg |
| 2007/0031844 A1 | 2/2007 | Khvorova et al. |
| 2007/0224624 A1 | 9/2007 | Pulst |
| 2008/0039618 A1 | 2/2008 | Allerson et al. |
| 2008/0113351 A1 | 5/2008 | Naito et al. |
| 2010/0190837 A1 | 7/2010 | Migawa et al. |
| 2010/0197762 A1 | 8/2010 | Swayze et al. |
| 2011/0054005 A1 | 3/2011 | Naito et al. |
| 2011/0142789 A1 | 6/2011 | Gitler et al. |
| 2013/0130378 A1 | 5/2013 | Manoharan et al. |
| 2013/0172399 A1* | 7/2013 | Corey .................. A61K 31/713 514/44 A |
| 2013/0225659 A1 | 8/2013 | Bennett et al. |
| 2014/0107330 A1 | 4/2014 | Freier et al. |
| 2014/0303238 A1 | 10/2014 | Linsley et al. |
| 2015/0018540 A1 | 1/2015 | Prakash et al. |
| 2015/0141320 A1 | 5/2015 | Krieg et al. |
| 2015/0184153 A1 | 7/2015 | Freier et al. |
| 2015/0191727 A1 | 7/2015 | Migawa et al. |
| 2015/0259679 A1 | 9/2015 | Bennett et al. |
| 2015/0267195 A1 | 9/2015 | Seth et al. |
| 2015/0275212 A1 | 10/2015 | Albaek et al. |
| 2016/0053254 A1* | 2/2016 | De Kimpe ........... C12N 15/113 514/44 R |
| 2017/0175114 A1 | 6/2017 | Freier et al. |

FOREIGN PATENT DOCUMENTS

| | | |
|---|---|---|
| WO | WO 1997/042314 | 11/1997 |
| WO | WO 2004/003201 | 1/2004 |
| WO | WO 2004/047872 | 6/2004 |
| WO | WO 2004/070062 | 8/2004 |
| WO | WO 2005/116204 | 12/2005 |
| WO | WO 2005/116212 | 12/2005 |
| WO | WO 2006/131925 | 12/2006 |
| WO | WO 2006/109379 | 9/2008 |
| WO | WO 2008/109450 | 9/2008 |
| WO | WO 2008/152636 | 12/2008 |
| WO | WO 2010/014592 | 2/2010 |
| WO | WO 2011/006121 | 1/2011 |
| WO | WO 2011/097641 | 8/2011 |
| WO | WO 2012/012467 | 1/2012 |
| WO | WO 2012/079578 | 6/2012 |
| WO | WO 2013/081864 | 6/2013 |
| WO | WO 2013/162363 | 10/2013 |
| WO | WO 2013/173645 | 11/2013 |
| WO | WO 2015/002971 | 1/2015 |
| WO | WO 2015/072438 | 5/2015 |
| WO | WO 2015/143245 | 9/2015 |
| WO | WO 2015/143246 | 9/2015 |
| WO | WO 2017/117496 | 7/2017 |

OTHER PUBLICATIONS

Branch et al., "A good antisense molecule is hard to find," TIBS (1998) 23:45-50.

Burke et al., "Huntingtin and DRPLA proteins selectively interact with the enzyme GAPDH." Nat. Med. (1996) 2(3):347-350.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Ciosk et al., "ATX-2, the C. elegans ortholog of ataxin 2 functions in translational regulation in the germline." Development (2004) 131(19):4831-4841.

Corrado et al., "ATXN-2 CAG repeat expansions are interrupted in ALS patients." Hum. Genet. (2011) 130(4):575-580.

Crooke, ST., et al., "Antisense Drug Technology" Second Edition, CRC Press (2008) Chapters 1-28.

Duvick et al., "SCA1-like disease in mice expressing wild-type ataxin-1 with a serine to aspartic acid replacement at residue 776." Neuron (2010) 67(6): 929-935.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Elden et al., "Ataxin-2 intermediate-length polyglutamine expansions are associated with increased risk for ALS." Nature (2010) 466: 1069-1075.

Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.

GenBank: NM_002973.3, Homo sapiens Ataxin 2 (ATXN2), transcript variant 1, mRNA, NCBI Accession No. NM_002973 (2015) (retrieved from the internet Jun. 28, 2017: https://www.ncbi.nlm.nih.gov/nuccore/171543894/).

GenBank: NT_009775.17 (truncated from nucleotides 2465000 to 2616000) Homo sapiens chromosome 12 genomic contig, GRCh37.p13 Primary Assembly (2013) (retrieved from the internet Jun. 28, 2017: https://www.ncbi.nlm.nih.gov/nuccore/NT_009775.17?report=genbank).

GenBank: BX410018.2, BX410018 Homo sapiens Fetal Brain Homo sapiens cDNA clone CS0DF030YB07 5-Prime, mRNA sequence; (2003) (retrieved from the internet Jun. 28, 2017: https://www.ncbi.nlm.nih.gov/nucest/BX410018.2).

Heuvel et al., "Taking a risk: a therapeutic focus on ataxin-2 in amyotrophic lateral sclerosis?" Trends Mol Med (2014) 20(1): 25-35.

Huynh et al., "Expression of ataxin-2 in brains from normal individuals and patients with Alzheimer's disease and spinocerebellar ataxia 2." Ann Neurol. (1999) 45: 232-241.

Huynh et al., "Expansion of the polyQ repeat in ataxin-2 alters its Golgi localization, disrupts the Golgi complex and causes cell death." Hum. Mol. Genet. (2003) 12: 1485-1496.

International Search Report for application PCT/US2015/021607 dated Jun. 29, 2015.

International Search Report for application PCT/US2015/021608 dated Jul. 1, 2015.

International Search Report for application PCT/US2016/069406 dated Mar. 31, 2017.

Kim et al., "Importance of low-range CAG expansion and CAA interruption in SCA2 Parkinsonism." Arch. Neurol. (2007) 64(10): 1510-1518.

Koshy et al., "Spinocerebellar ataxia type-1 and spinobulbar muscular atrophy gene products interact with glyceraldehyde-3-phosphate dehydrogenase" Hum. Mol. Genet. (1996) 5(9): 1311-1318.

Lajoie et al., "Formation and toxicity of soluble polyglutamine oligomers in living cells." PLoS One (2010) 5(12): e15245 1-15.

Lovett-Racke et al., Therapeutic Potential of Small Interfering RNA for Central Nervous System Diseases. Archives of Neurobiology (2005) 62:1810-1813.

Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.

New England Biolabs 1998/99 Catalog (cover page and pp. 121 and 284).

Nonhoff et al., "Ataxia-2 interacts with the DEAD/H-box RNA helicase DDX6 and interferes with P-bodies and stress granules." Mol. Biol. Cell (2007) 18(4):1385-1396.

Nonis et al., "Ataxin-2 associates with the endocytosis complex and affects EGF receptor trafficking" Cell Signal (2008) 20(10):1725-1739.

Pulst S.M. (ed.) "Inherited Ataxias: An Introduction" Genetics of Movement Disorders. Elsevier, Inc., Amsterdam, published Oct. 3, 2002, pp. 19-34.

Pulst S.M., "Rare mendelian diseases: pathways to therapy development" Oral presentation, American Academy of Neurology Annual Meeting, Philadelphia, PA, Apr. 29, 2014.

Ramachandran, P. "RNA interference therapy for the Spinocerebellar ataxias." Thesis, May 2014, University of Iowa, pp. 1-140.

Reynolds et al., "Rational siRNA design for RNA interference" Nature Biotechnology (2004) 22(3):326-330.

Ross et al., "Ataxin-2 repeat-length variation and neurodegeneration." Hum. Mol. Genet. (2011) 20(16): 3207-3212.

(56) References Cited

OTHER PUBLICATIONS

Sanghvi et al., "Heterocyclic Base Modifications in Nucleic Acids and Their Applications in Antisense Oligonucleotides" Antisense Research and Applications (1993) pp. 273-288.
Satterfield et al., "Ataxin-2 and its *Drosophila* homolog, ATX2, physically assemble with polyribosomes." Hum. Mol. Genet. (2006) 15(16):2523-2532.
Scoles et al., "Antisense oligonucleotides for the treatment of spinocerebellar ataxia type 2 (SCA2)" AAN Annual Meeting abstract published online Feb. 26, 2015; Neurology (2015) 82(Meeting Abstracts): S32.002.
Scoles et al, Antisense oligonucleotides for the treatment of spinocerebellar ataxia type 2 (SCA2), 5th Ataxia Investigators Meeting (AIM) meeting abstract presented Mar. 20, 2014.
Scoles et al., "ETS1 regulates the expression of ATXN2" Human Mol Genetics (2012) 21(23): 5048-65.
Scoles et al., "Treatment of Spinocerebellar Ataxia Type 2 (SCA2) with MOE Antisense Oligonucleotides." AAN Annual Meeting abstract published online Feb. 26, 2014; Neurology (2014) 82(10 Supplement): S47.006.
Seth et al., "Short Antisense Oligonucleotides with Novel 2'-4' Conformationally Restricted Nucleoside Analogues Show Improved Potency Without Increased Toxicity in Animals." J Med Chem (2009) 52:10-13.
Shibata et al., "A novel protein with RNA-binding motifs interacts with ataxin-2." Hum. Mol. Genet. (2000) 9(9): 1303-1313.
Van Damme et al., "Expanded ATXN2 CAG repeat size in ALS identifies genetic overlap between ALS and SCA2." Neurology (2011) 76(24):2066-2072.
Woolf et al. "Specificity of antisense oligonucleotides in vivo" PNAS (1992) 89:7305-7309.
Yamanaka et al., "Transcription factor sequestration by polyglutamine proteins." Methods Mol. Biol. (2010) 648:215-229.
European partial search report for application No. 15765851.9, dated Oct. 25, 2017, 14 pages.
Scoles et al., "ATXN2 is Regulated by a Promoter Associated Antisense Long Noncoding RNA (lncRNA)," Neurology, 2013, 80:P05030, 2 pages.
Evers et al., "Targeting Several CAG Expansion Diseases by a Single Antisense Oligonucleotide" PLoS ONE (2011) 6(9):e24308.
Extended Ep Search Report for 15765851.9 dated Jan. 30, 2018.

\* cited by examiner

METHODS FOR MODULATING ATAXIN 2 EXPRESSION

STATEMENT OF GOVERNMENT SUPPORT

This invention was made with government support under R21 NS081182 awarded by the National Institutes of Health. The government has certain rights in the invention.

SEQUENCE LISTING

The present application is being filed along with a Sequence Listing in electronic format. The Sequence Listing is provided as a file entitled BIOL0242USASEQ_ST25.txt created Sep. 12, 2016, which is 232 Kb in size. The information in the electronic format of the sequence listing is incorporated herein by reference in its entirety.

FIELD

Provided are methods for reducing expression of Ataxin 2 (ATXN2) mRNA and protein in an animal. Such methods are useful to treat, prevent, or ameliorate neurodegenerative diseases, including spinocerebellar ataxia type 2 (SCA2), amyotrophic lateral sclerosis (ALS), and parkinsonism by inhibiting expression of Ataxin 2 in an animal.

BACKGROUND

Spinocerebellar ataxia type 2 (SCA2) is an autosomal dominant neurodegenerative disease characterized by progressive functional and cell loss of neurons in the cerebellum, brain stem and spinal cord. The cause of SCA2 is CAG expansion in the ATXN2 gene resulting in polyglutamine (polyQ) expansion in the ataxin-2 protein. Patients with SCA2 are characterized by progressive cerebellar ataxia, slow saccadic eye movements and other neurologic features such as neuropathy (Pulst, S. M. (ed.), *Genetics of Movement Disorders.* Elsevier, Inc., Amsterdam, 2003, pp. 19-34.). Moderate CAG expansion in the ATXN2 gene is also associated with parkinsonism or amyotrophic lateral sclerosis (ALS) indistinguishable from the idiopathic forms of these diseases (Kim et al., *Arch. Neurol.,* 2007, 64: 1510-1518; Ross et al., *Hum. Mol. Genet.,* 2011, 20: 3207-3212; Corrado et al., *Hum. Genet.,* 2011, 130: 575-580; Elden et al., *Nature,* 2010, 466: 1069-1075; Van Damme et al., *Neurology,* 2011, 76: 2066-2072).

The pathogenic functions of polyQ disease proteins that occur with polyQ expansion may be attributed to the gain of toxicity associated with the development of intranuclear inclusion bodies or with soluble toxic oligomers (Lajoie et al., *PLoS One,* 2011, 5: e15245). While SCA2 patient brains are characterized by loss of Purkinje cells, SCA2 Purkinje cells lack inclusion bodies indicating polyQ-expanded ataxin-2 may cause toxicity that is unrelated to inclusion body formation (Huynh et al., *Ann. Neurol.,* 1999, 45: 232-241). Functions gained in polyQ-expanded ataxin-2 may include anomalous accumulation in Golgi bodies (Huynh et al., *Hum. Mol. Genet.,* 2003, 12: 1485-1496), gain-of-normal functions (Duvick et al., *Neuron,* 2010, 67: 929-935) and sequestering of transcription factors (TFs) and glyceraldehyde-3-phosphate dehydrogenase like for other polyQ proteins (Yamanaka et al., *Methods Mol. Biol.,* 2010: 648, 215-229; Koshy et al., *Hum. Mol. Genet.,* 1996, 5: 1311-1318; Burke et al., *Nat. Med.,* 1996, 2: 347-350). Some normal functions of ataxin-2 have been characterized. Ataxin-2 is present in stress granules and P-bodies suggesting functions in sequestering mRNAs and protein translation regulation during stress (Nonhoff et al., *Mol. Biol. Cell,* 2007, 18: 1385-1396). Ataxin-2 overexpression interfered with the P-body assembly, while underexpression interfered with stress granule assembly (Nonhoff et al., *Mol. Biol. Cell,* 2007, 18: 1385-1396). Interactions with polyA-binding protein 1, the RNA splicing factor A2BP1/Fox1 and polyribosomes further support roles for ataxin-2 in RNA metabolism (Shibata et al., *Hum. Mol. Genet.,* 2000, 9: 1303-1313; Ciosk et al., *Development,* 2004, 131: 4831-4841; Satterfield et al., *Hum. Mol. Genet.,* 2006, 15: 2523-2532). Ataxin-2 is a regulator of EGF receptor internalization and signaling by the way of its interactions with SRC kinase and the endocytic protein C1N85 (Nonis et al., *Cell Signal.,* 2008, 20: 1725-1739). Ataxin-2 also interacts with the ALS-related protein TDP-43 in an RNA-dependent manner and familial and sporadic ALS associates with the occurrence of long normal CAG repeat expansion ATXN2 (Elden et al., *Nature,* 2010, 466: 1069-1075; Van Damme et al., *Neurology,* 2011, 76: 2066-2072).

Currently there is a lack of acceptable options for treating such neurodegenerative diseases. It is therefore an object herein to provide methods for the treatment of such diseases.

SUMMARY

Provided herein are methods for modulating expression of Ataxin 2 (ATXN2) mRNA and protein. In certain embodiments, compounds useful for modulating expression of Ataxin 2 mRNA and protein are antisense compounds. In certain embodiments, the antisense compounds are modified oligonucleotides.

In certain embodiments, modulation can occur in a cell or tissue. In certain embodiments, the cell or tissue is in an animal. In certain embodiments, the animal is a human. In certain embodiments, Ataxin 2 mRNA levels are reduced. In certain embodiments, Ataxin 2 protein levels are reduced. Such reduction can occur in a time-dependent manner or in a dose-dependent manner.

Also provided are methods useful for preventing, treating, and ameliorating diseases, disorders, and conditions. In certain embodiments, such Ataxin 2 related diseases, disorders, and conditions are neurodegenerative diseases. In certain embodiments, such neurodegenerative diseases, disorders, and conditions include spinocerebellar ataxia type 2 (SCA2), amyotrophic lateral sclerosis (ALS), and parkinsonism.

Such diseases, disorders, and conditions can have one or more risk factors, causes, or outcomes in common. Certain risk factors and causes for development of neurodegenerative disorder include growing older, having a personal or family history, or genetic predisposition. Certain symptoms and outcomes associated with development of a neurodegenerative disorder include but are not limited to: ataxia, speech and swallowing difficulties, rigidity, tremors, ophthalmoplegia, saccadic slowing, peripheral neuropathy, atrophy, dystonia, chorea, and dementia.

In certain embodiments, methods of treatment include administering an Ataxin 2 antisense compound to an individual in need thereof. In certain embodiments, methods of treatment include administering an Ataxin 2 modified oligonucleotide to an individual in need thereof.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Ataxin 2", it is implied that the Ataxin 2 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Ataxin 2" means the mammalian gene Ataxin 2 (ATXN2), including the human gene Ataxin 2 (ATXN2). Human Ataxin 2 has been mapped to human chromosome 12q24.1.

"Ataxin 2 associated disease" means any disease associated with any Ataxin 2 nucleic acid or expression product thereof. Such diseases may include a neurodegenerative disease. Such neurodegenerative diseases may include spinocerebellar ataxia type 2 (SCA2), amyotrophic lateral sclerosis (ALS), and parkinsonism.

"Ataxin 2 mRNA" means any messenger RNA expression product of a DNA sequence encoding Ataxin 2.

"Ataxin 2 nucleic acid" means any nucleic acid encoding Ataxin 2. For example, in certain embodiments, an Ataxin 2 nucleic acid includes a DNA sequence encoding Ataxin 2, an RNA sequence transcribed from DNA encoding Ataxin 2 (including genomic DNA comprising introns and exons), and an mRNA sequence encoding Ataxin 2. "Ataxin 2 mRNA" means an mRNA encoding an Ataxin 2 protein.

"Ataxin 2 protein" means the polypeptide expression product of an Ataxin 2 nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH($CH_3$)—O-2'.

"Constrained ethyl nucleoside" (also cEt nucleoside) means a nucleoside comprising a bicyclic sugar moiety comprising a 4'-CH($CH_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having an Ataxin 2 associated disease" means identifying an animal having been diagnosed with an Ataxin 2 associated disease or predisposed to develop an Ataxin 2 associated disease. Individuals predisposed to develop an Ataxin 2 associated disease include those having one or more risk factors for developing an Ataxin 2 associated disease, including, growing older, having a personal or family history, or genetic predisposition of one or more Ataxin 2 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting Ataxin 2" means reducing the level or expression of an Ataxin 2 mRNA and/or protein. In certain embodiments, Ataxin 2 mRNA and/or protein levels are inhibited in the presence of an antisense compound targeting Ataxin 2, including an antisense oligonucleotide targeting Ataxin 2, as compared to expression of Ataxin 2 mRNA and/or protein levels in the absence of an Ataxin 2 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

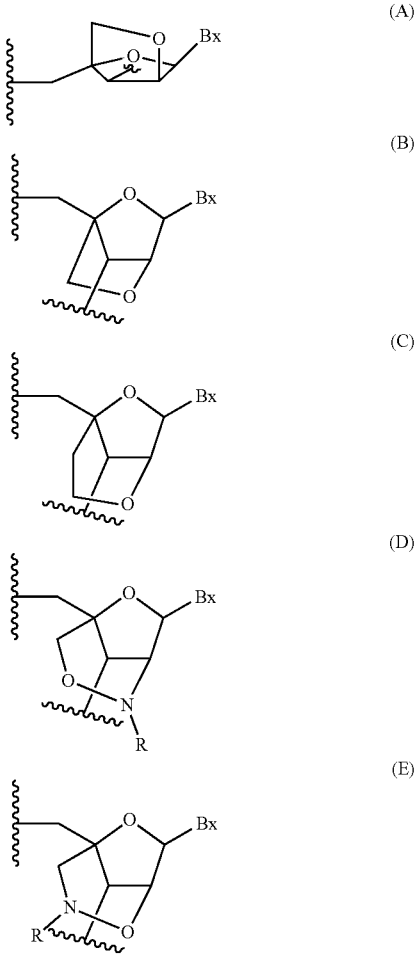

As used herein, LNA compounds include, but are not limited to, compounds having at least one bridge between the 4' and the 2' position of the sugar wherein each of the bridges independently comprises 1 or from 2 to 4 linked groups independently selected from $-[C(R_1)(R_2)]_n-$, $-C(R_1)=C(R_2)-$, $-C(R_1)=N-$, $-C(=NR_1)-$, $-C(=O)-$, $-C(=S)-$, $-O-$, $-Si(R_1)_2-$, $-S(=O)_x-$ and $-N(R_1)-$; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: $-[C(R_1)(R_2)]_n-$, $-[C(R_1)(R_2)]_n-O-$, $-C(R_1R_2)-N(R_1)-O-$ or $-C(R_1R_2)-O-N(R_1)-$. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

A "modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to Ataxin 2 is a pharmaceutical agent.

"Pharmaceutical composition" means a mixture of substances suitable for administering to a subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disease or condition.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide methods for inhibiting Ataxin 2 mRNA and protein expression. Certain embodiments provide methods, compounds, and composition for decreasing Ataxin 2 mRNA and protein levels.

Certain embodiments provide antisense compounds targeted to an Ataxin 2 nucleic acid. In certain embodiments, the Ataxin 2 nucleic acid is the sequence set forth in GENBANK Accession No. NM_002973.3 (incorporated herein as SEQ ID NO: 1), the complement of GENBANK Accession No. NT_009775.17 truncated from nucleotides 2465000 to U.S. Pat. No. 2,616,000 (incorporated herein as SEQ ID NO: 2) and GENBANK Accession No. BX410018.2 (incorporated herein as SEQ ID NO: 3).

Certain embodiments provide methods for the treatment, prevention, or amelioration of diseases, disorders, and conditions associated with Ataxin 2 in an individual in need thereof. Also contemplated are methods for the preparation of a medicament for the treatment, prevention, or amelioration of a disease, disorder, or condition associated with Ataxin 2. Ataxin 2 associated diseases, disorders, and conditions include neurodegenerative diseases. In certain embodiments, Ataxin 2 associated diseases include spinocerebellar ataxia type 2 (SCA2), amyotrophic lateral sclerosis (ALS), and parkinsonism.

Certain embodiments provide methods comprising administering an Ataxin 2 antisense compound to an animal for treating an Ataxin 2 associated disease.

Certain embodiments provide methods comprising identifying an animal having an Ataxin 2 associated disease; and administering an Ataxin 2 antisense compound.

In certain embodiments, the Ataxin 2 associated disease is a neurodegenerative disease.

In certain embodiments, the Ataxin 2 associated disease is spinocerebellar ataxia type 2 (SCA2), amyotrophic lateral sclerosis (ALS), or parkinsonism.

In certain embodiments, the animal is a human.

In certain embodiments, the administering is parenteral administration.

In certain embodiments, the parenteral administration is any of intrathecal administration or intracerebroventricular administration.

In certain embodiments, the administering distributes the antisense compound to the Purkinje cells.

In certain embodiments, the administering improves rotarod performance.

In certain embodiments, rotarod performance is improved by 10 percent, 15 percent, or 20 percent.

In certain embodiments, the administering improves motor function.

In certain embodiments, at least one symptom of an Ataxin 2 associated disease is ameliorated, treated, prevented, or slowed.

In certain embodiments, the antisense compound is a modified oligonucleotide.

In certain embodiments, the modified oligonucleotide has the nucleobase sequence of SEQ ID NO: 15, 20, 26, 36, 43, 81, 103, or 109.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an Ataxin 2 nucleic acid is 12 to 30 subunits in length. In certain embodiments, an antisense compound targeted to an Ataxin 2 nucleic acid is 12 to 25 subunits in length. In certain embodiments, an antisense compound targeted to an Ataxin 2 nucleic acid is 12 to 22 subunits in length. In certain embodiments, an antisense compound targeted to an Ataxin 2 nucleic acid is 14 to 20 subunits in length. In certain embodiments, an antisense compound targeted to an Ataxin 2 nucleic acid is 15 to 25 subunits in length. In certain embodiments, an antisense compound targeted to an Ataxin 2 nucleic acid is 18 to 22 subunits in length. In certain embodiments, an antisense compound targeted to an Ataxin 2 nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to an Ataxin 2 nucleic acid is 12 subunits in length. In certain embodiments, an antisense compound targeted to an Ataxin 2 nucleic acid is 13 subunits in length. In certain embodiments, an antisense compound targeted to an Ataxin 2 nucleic acid is 14 subunits in length. In certain embodiments, an antisense compound targeted to an Ataxin 2 nucleic acid is 15 subunits in length. In certain embodiments, an antisense compound targeted to an Ataxin 2 nucleic acid is 16 subunits in length. In certain embodiments, an antisense compound targeted to an Ataxin 2 nucleic acid is 17 subunits in length. In certain embodiments, an antisense compound targeted to an Ataxin 2 nucleic acid is 18 subunits in length. In certain embodiments, an antisense compound targeted to an Ataxin 2 nucleic acid is 19 subunits in length. In certain embodiments, an antisense compound targeted to an Ataxin 2 nucleic acid is 20 subunits in length. In certain embodiments, an antisense compound targeted to an Ataxin 2 nucleic acid is 21 subunits in length. In certain embodiments, an antisense compound targeted to an Ataxin 2 nucleic acid is 22 subunits in length. In certain embodiments, an antisense compound targeted to an Ataxin 2 nucleic acid is 23 subunits in length. In certain embodiments, an antisense compound targeted to an Ataxin 2 nucleic acid is 24 subunits in length. In certain embodiments, an antisense compound targeted to an Ataxin 2 nucleic acid is 25 subunits in length. In certain embodiments, an antisense compound targeted to an Ataxin 2 nucleic acid is 26 subunits in length. In certain embodiments, an antisense compound targeted to an Ataxin 2 nucleic acid is 27 subunits in length. In certain embodiments, an antisense compound targeted to an Ataxin 2 nucleic acid is 28 subunits in length. In certain embodiments, an antisense compound targeted to an Ataxin 2 nucleic acid is 29 subunits in length. In certain embodiments, an antisense compound targeted to an Ataxin 2 nucleic acid is 30 subunits in length. In certain embodiments, the antisense compound targeted to an Ataxin 2 nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to an Ataxin 2 nucleic acid may be shortened or truncated. For example, a single subunit may be deleted from the 5' end (5' truncation), or alternatively from the 3' end (3' truncation). A shortened or truncated antisense compound targeted to an Ataxin 2 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an Ataxin 2 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)$n-O-2' bridge, where n=1 or n=2 and 4'-$CH_2$—O—$CH_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X—Y—Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5.

In certain embodiments, gapmers provided herein include, for example 19-mers having a motif of 5-9-5.

In certain embodiments, gapmers provided herein include, for example 18-mers having a motif of 5-8-5.

In certain embodiments, gapmers provided herein include, for example 18-mers having a motif of 4-8-6.

In certain embodiments, gapmers provided herein include, for example 18-mers having a motif of 6-8-4.

In certain embodiments, gapmers provided herein include, for example 18-mers having a motif of 5-7-6.

Target Nucleic Acids, Target Regions and Nucleotide Sequences

Nucleotide sequences that encode Ataxin 2 include, without limitation, the following: GENBANK Accession No. NM_002973.3 (incorporated herein as SEQ ID NO: 1), the complement of GENBANK Accession No. NT_009775.17 truncated from nucleotides 2465000 to U.S. Pat. No. 2,616,000 (incorporated herein as SEQ ID NO: 2) and GENBANK Accession No. BX410018.2 (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Ataxin 2 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Ataxin 2 mRNA levels are indicative of inhibition of Ataxin 2 expression. Reductions in levels of an Ataxin 2 protein are also indicative of inhibition of target mRNA expression. Phenotypic changes are indicative of inhibition of Ataxin 2 expression. Improvement in neurological function is indicative of inhibition of Ataxin 2 expression. Improved motor function and memory are indicative of inhibition of Ataxin 2 expression.

Hybridization

In some embodiments, hybridization occurs between an antisense compound disclosed herein and an Ataxin 2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an Ataxin 2 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Ataxin 2 nucleic acid).

Non-complementary nucleobases between an antisense compound and an Ataxin 2 nucleic acid may be tolerated provided that the antisense compound remains able to specifically hybridize to a target nucleic acid. Moreover, an antisense compound may hybridize over one or more segments of an Ataxin 2 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Ataxin 2 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an Ataxin 2 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Ataxin 2 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Ataxin 2 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Ataxin 2 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C($R_1$)($R_2$) (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Serial Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

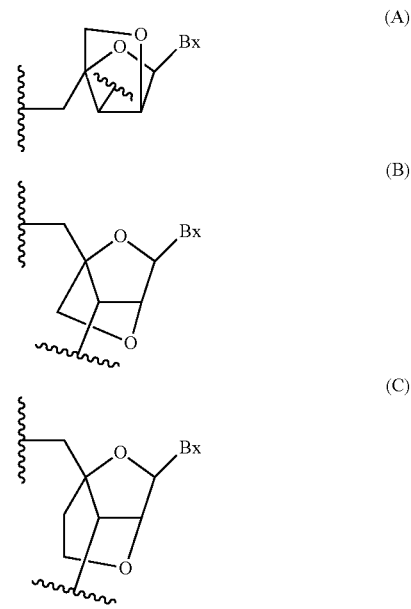

-continued (D) 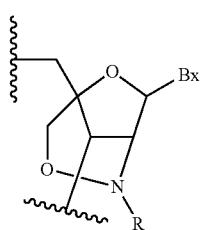

(E) 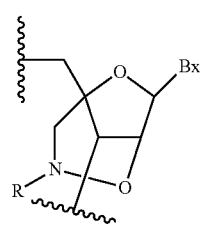

(F) 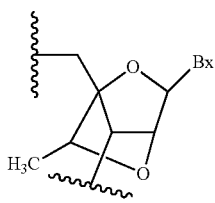

(G) 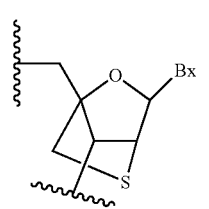

(H) 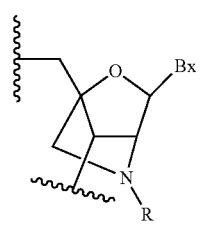

(I) 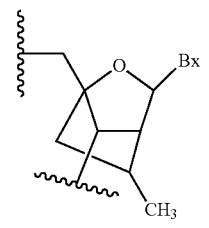

(J) 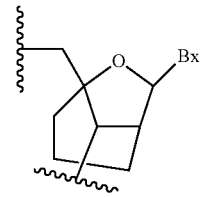

wherein Bx is the base moiety and R is independently H, a protecting group or $C_1$-$C_{12}$ alkyl.

In certain embodiments, bicyclic nucleosides are provided having Formula I:

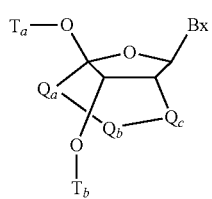

I wherein:
Bx is a heterocyclic base moiety;
-$Q_a$-$Q_b$-$Q_c$- is —$CH_2$—$N(R_c)$—$CH_2$—, —$C(=O)$—$N(R_c)$—$CH_2$—, —$CH_2$—O—$N(R_c)$—, —$CH_2$—$N(R_c)$—O— or —$N(R_c)$—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

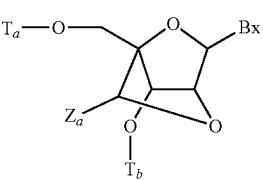

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_cC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

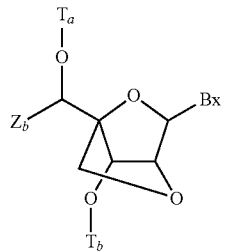

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

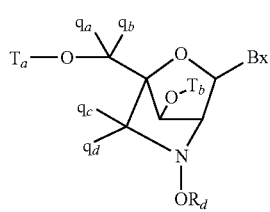

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

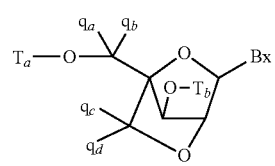

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl. The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

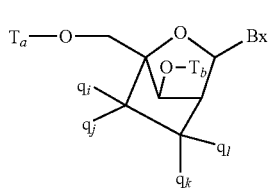

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)$—$CH_3$, $O(CH_2)_nF$, $O(CH_2)_nONH_2$, $OCH_2C(\!=\!O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

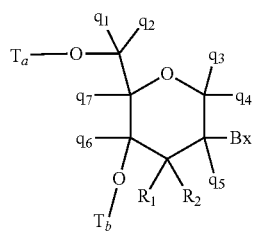

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(\!=\!X)J_1$, $OC(\!=\!X)NJ_1J_2$, $NJ_3C(\!=\!X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—$C(\!=\!O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an Ataxin 2 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an Ataxin 2 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Ataxin 2 nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of an Ataxin 2 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900

Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an Ataxin 2 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Ataxin 2 nucleic acids can be assessed by measuring Ataxin 2 protein levels. Protein levels of Ataxin 2 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Ataxin 2 and produce phenotypic changes, such as, improved motor function and cognition. In certain embodiments, motor function is measured by walking initiation analysis, rotarod, grip strength, pole climb, open field performance, balance beam, hindpaw footprint testing in the animal.

Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in Ataxin 2 nucleic acid expression are measured.

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, spinocerebellar ataxia type 2 (SCA2), amyotrophic lateral sclerosis (ALS), and parkinsonism. In certain embodiments, the individual has been identified as having an Ataxin 2 associated disease. In certain embodiments, provided herein are methods for prophylactically reducing Ataxin 2 expression in an individual. Certain embodiments include treating an individual in need thereof by administering to an individual a therapeutically effective amount of an antisense compound targeted to an Ataxin 2 nucleic acid.

In one embodiment, administration of a therapeutically effective amount of an antisense compound targeted to an Ataxin 2 nucleic acid is accompanied by monitoring of Ataxin 2 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to an Ataxin 2 nucleic acid results in reduction of Ataxin 2 expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values. In certain embodiments, administration of an antisense compound targeted to an Ataxin 2 nucleic acid results in improved motor function in an animal. In certain embodiments, administration of an Ataxin 2 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, pharmaceutical compositions comprising an antisense compound targeted to Ataxin 2 are used for the preparation of a medicament for treating a patient suffering or susceptible to a neurodegenerative disease including spinocerebellar ataxia type 2 (SCA2), amyotrophic lateral sclerosis (ALS), and parkinsonism.

EXAMPLES

Non-Limiting Disclosure and Incorporation by Reference

While certain methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Ataxin 2 in HepG2 Cells by MOE Gapmers

Antisense oligonucleotides were designed targeting an ataxin 2 nucleic acid and were tested for their effects on ataxin 2 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and ataxin 2 mRNA levels were measured by quantitative real-time PCR. Human primer probe set RTS3642 (forward sequence ACCAAAGAG-TAGTTAATGGAGGTGTTC, designated herein as SEQ ID NO: 5; reverse sequence AGAAGGTGGGCGAGAGGAA, designated herein as SEQ ID NO: 6; probe sequence CTG-GCCATCGCCTTGCCCA, designated herein as SEQ ID NO: 7) was used to measure mRNA levels. Ataxin 2 mRNA levels were adjusted according to total RNA content, as measured by RIBOGREEN®. Results are presented as percent inhibition of ataxin 2, relative to untreated control cells.

The chimeric antisense oligonucleotides in the Tables below were designed as 5-10-5 MOE gapmers. The gapmers are 20 nucleosides in length, wherein the central gap segment is comprised of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human ataxin 2 mRNA, designated herein as SEQ ID NO: 1 (GENBANK Accession No. NM_002973.3) or the human ataxin 2 genomic sequence, designated herein as SEQ ID NO: 2 (the complement of GENBANK Accession No. NT_009775.17 truncated from nucleotides 2465000 to 2616000). Some oligonucleotides do not target either SEQ ID NO: 1 or SEQ ID NO: 2, but instead target a variant gene sequence, SEQ ID NO: 3 (GENBANK Accession No. BX410018.2). 'n/a' indicates that the antisense oligonucleotide does not target that particular gene sequence with 100% complementarity.

TABLE 1

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564118 | 606 | 625 | CCGGCTCGCACGCCGGGCGG | 57 | 2596 | 2615 | 11 |
| 564119 | 612 | 631 | CATACACCGGCTCGCACGCC | 63 | 2602 | 2621 | 12 |
| 564120 | 637 | 656 | GGCTTCAGCGACATGGTGAG | 78 | 2627 | 2646 | 13 |
| 564121 | 880 | 899 | CGACCTCTGCCCAGGCCGGG | 67 | n/a | n/a | 14 |
| 564122 | 935 | 954 | TGCATAGATTCCATCAAAAG | 90 | 47454 | 47473 | 15 |
| 564123 | 959 | 978 | AAGTATATGAACCATCCTCA | 67 | 47478 | 47497 | 16 |
| 564124 | 997 | 1016 | TTCACTTGTACTTCACATTT | 85 | 48696 | 48715 | 17 |
| 564125 | 1084 | 1103 | TCTGTACTTTTCTCATGTGC | 88 | 49258 | 49277 | 18 |
| 564126 | 1090 | 1109 | CTGGATTCTGTACTTTTCTC | 89 | 49264 | 49283 | 19 |
| 564127 | 1123 | 1142 | CTCTCCATTATTTCTTCACG | 92 | 49297 | 49316 | 20 |
| 564128 | 1168 | 1187 | TCTTTAAACTGTACCACAAC | 86 | 49342 | 49361 | 21 |
| 564129 | 1210 | 1229 | GAGTCAGTAAAAGCATCTCT | 84 | n/a | n/a | 22 |
| 564130 | 1264 | 1283 | CAGGGCTCCAGGTCCTTCTC | 83 | 76401 | 76420 | 23 |
| 564131 | 1270 | 1289 | GCATCCCAGGGCTCCAGGTC | 86 | 76407 | 76426 | 24 |
| 564132 | 1363 | 1382 | TCTTCATTATATCGAAACAT | 84 | 80718 | 80737 | 25 |
| 564133 | 1477 | 1496 | GCTAACTGGTTTGCCCTTGC | 98 | 81637 | 81656 | 26 |
| 564134 | 1556 | 1575 | GTATTTTCTTCCTCACTCC | 82 | 81716 | 81735 | 27 |
| 564135 | 1562 | 1581 | TGCTGTGTATTTTTCTTCCT | 89 | 81722 | 81741 | 28 |
| 564136 | 1748 | 1767 | GAAATCTGAAGTGTGAGAAG | 61 | 83359 | 83378 | 29 |
| 564137 | 1789 | 1808 | CCTCCATTAACTACTCTTTG | 90 | 83400 | 83419 | 30 |
| 564138 | 1795 | 1814 | GGAACACCTCCATTAACTAC | 66 | n/a | n/a | 31 |
| 564139 | 1807 | 1826 | GGCGATGGCCAGGGAACACC | 95 | 85303 | 85322 | 32 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564140 | 1844 | 1863 | GTAGCGAGAAGGTGGGCGAG | 88 | 85340 | 85359 | 33 |
| 564141 | 1862 | 1881 | AGAGTTGGGACCTGACTGGT | 84 | 85358 | 85377 | 34 |
| 564142 | 1868 | 1887 | TGGAAGAGAGTTGGGACCTG | 84 | 85364 | 85383 | 35 |
| 564143 | 1963 | 1982 | GGAGCTGGAGAACCATGAGC | 91 | 85459 | 85478 | 36 |
| 564144 | 1969 | 1988 | GAGACAGGAGCTGGAGAACC | 86 | 85465 | 85484 | 37 |
| 564145 | 2101 | 2120 | TTGTGGGATACAAATTCTAG | 56 | 88211 | 88230 | 38 |
| 564146 | 2185 | 2204 | GGAACCCCACTGACCACTGA | 70 | n/a | n/a | 39 |
| 564147 | 2401 | 2420 | TCTTGAAGCCTGGAATCTTT | 61 | 91671 | 91690 | 40 |
| 564148 | 2560 | 2579 | AACCTAAAATCATTCTTAAA | 21 | n/a | n/a | 41 |
| 564149 | 2596 | 2615 | AGTTGATCCATAGATTCAGA | 74 | 112905 | 112924 | 42 |
| 564150 | 2704 | 2723 | CTGGTACAGTTGCTGCTGCT | 91 | 113013 | 113032 | 43 |
| 564151 | 2710 | 2729 | CTGCCACTGGTACAGTTGCT | 85 | 113019 | 113038 | 44 |
| 564152 | 2899 | 2918 | TTTGCATTGGGATTCAATGT | 76 | 114859 | 114878 | 45 |
| 564153 | 2938 | 2957 | GAAGGCTTTGGCTGAGAGAA | 66 | n/a | n/a | 46 |
| 564154 | 2944 | 2963 | GTAGTAGAAGGCTTTGGCTG | 71 | n/a | n/a | 47 |
| 564155 | 2995 | 3014 | TGACCCACCATAGATGGGCT | 38 | 115850 | 115869 | 48 |
| 564156 | 3097 | 3116 | GGTATTGGGTATAAAGGTTG | 57 | n/a | n/a | 49 |
| 564157 | 3103 | 3122 | GTCATAGGTATTGGGTATAA | 76 | 116339 | 116358 | 50 |
| 564158 | 3331 | 3350 | GGATGCTGAGACTGATAATG | 54 | n/a | n/a | 51 |
| 564159 | 3337 | 3356 | ACATGAGGATGCTGAGACTG | 63 | n/a | n/a | 52 |
| 564160 | 3472 | 3491 | AATTTGGGACATGCATACAT | 23 | n/a | n/a | 53 |
| 564161 | 3490 | 3509 | GTCTCCTTGTTGTATGGTAA | 76 | 136963 | 136982 | 54 |
| 564162 | 3658 | 3677 | TGAACAGGACTGGGTGCAGG | 41 | 144433 | 144452 | 55 |
| 564163 | 3715 | 3734 | GACTGCTGCTGTGGACTGGC | 69 | 145447 | 145466 | 56 |
| 564164 | 3903 | 3922 | CTGACTGTACATGAGCCTGA | 50 | 147818 | 147837 | 57 |
| 564165 | 3909 | 3928 | CCATTCCTGACTGTACATGA | 69 | 147824 | 147843 | 58 |
| 564166 | 3927 | 3946 | CAGTTGGATGAGAAGGAACC | 58 | 147842 | 147861 | 59 |
| 564167 | 3933 | 3952 | CATGGGCAGTTGGATGAGAA | 29 | 147848 | 147867 | 60 |
| 564168 | 3971 | 3990 | ACCGCCGGGTGGCTGTGTCG | 40 | 147886 | 147905 | 61 |
| 564169 | 3993 | 4012 | TTTGAGCGAGGGCGGCCTGG | 19 | 147908 | 147927 | 62 |
| 564170 | 4005 | 4024 | GCTGTAGTGCACTTTGAGCG | 73 | 147920 | 147939 | 63 |
| 564171 | 4017 | 4036 | AGACTGGAATGGGCTGTAGT | 58 | 147932 | 147951 | 64 |
| 564172 | 4029 | 4048 | GCGCTGTTGTCGAGACTGGA | 74 | 147944 | 147963 | 65 |
| 564173 | 4035 | 4054 | GGAAATGCGCTGTTGTCGAG | 69 | 147950 | 147969 | 66 |
| 564174 | 4064 | 4083 | GGCTTGTACTGAAGGGTGCG | 23 | n/a | n/a | 67 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564175 | 4070 | 4089 | GTGGTGGGCTTGTACTGAAG | 35 | n/a | n/a | 68 |
| 564176 | 4076 | 4095 | CTGTTGGTGGTGGGCTTGTA | 22 | 148827 | 148846 | 69 |
| 564177 | 4082 | 4101 | CAACTGCTGTTGGTGGTGGG | 39 | 148833 | 148852 | 70 |
| 564178 | 4088 | 4107 | GCCTTACAACTGCTGTTGGT | 62 | 148839 | 148858 | 71 |
| 564179 | 4106 | 4125 | TTCGGTTCCTCCAGGGCAGC | 72 | 148857 | 148876 | 72 |
| 564180 | 4166 | 4185 | TTCTAGTTTTCTGTGCTTCC | 72 | 148917 | 148936 | 73 |
| 564181 | 4367 | 4386 | AATAAATAACTTCCAGTTTC | 59 | 149118 | 149137 | 74 |
| 564182 | 4429 | 4448 | GAATCACTCTTGTTACTTCT | 78 | 149180 | 149199 | 75 |
| 564183 | 4435 | 4454 | CAGCAAGAATCACTCTTGTT | 85 | 149186 | 149205 | 76 |
| 564184 | 4551 | 4570 | TTTATAAATAATAATCCGTC | 4 | 149302 | 149321 | 77 |
| 564185 | 4593 | 4612 | AAGTTGAACCACTGTAGACA | 60 | 149344 | 149363 | 78 |
| 564186 | n/a | n/a | ATCGGCCACCACCCGCGCGC | 55 | 3683 | 3702 | 79 |
| 564187 | n/a | n/a | CAAAGGGTTAATTAGGATCT | 66 | 85057 | 85076 | 80 |
| 564188 | n/a | n/a | CCCAAAGGGTTAATTAGGAT | 94 | 85059 | 85078 | 81 |
| 564189 | n/a | n/a | AGGACAGTCATTTGATTTGT | 72 | 85166 | 85185 | 82 |
| 564190 | n/a | n/a | CTTTGAGGACAGTCATTTGA | 70 | 85171 | 85190 | 83 |
| 564191 | n/a | n/a | CTGACAGAACAAATGATATG | 17 | 85284 | 85303 | 84 |
| 564192 | n/a | n/a | TATTGGGTATAAAGGCTTGA | 31 | 116331 | 116350 | 85 |
| 564193 | n/a | n/a | GGTATTGGGTATAAAGGCTT | 78 | 116333 | 116352 | 86 |
| 564194 | n/a | n/a | CTCTTTTACGCATACAGGCA | 74 | 147789 | 147808 | 87 |
| 564195 | n/a | n/a | AGGAAGGCCAACTGAGTCCT | 70 | 148258 | 148277 | 88 |

TABLE 2

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564158 | 3331 | 3350 | GGATGCTGAGACTGATAATG | 61 | n/a | n/a | 51 |
| 564196 | 70 | 89 | GGTCAGACGGAAGCAGAACG | 9 | 2060 | 2079 | 89 |
| 564197 | 218 | 237 | CCACCTGGCTGCGGCGAAGC | 12 | 2208 | 2227 | 90 |
| 564198 | 392 | 411 | GCCGTTGCCGTTGCTACCAA | 80 | 2382 | 2401 | 91 |
| 564199 | 616 | 635 | GGCCCATACACCGGCTCGCA | 79 | 2606 | 2625 | 92 |
| 564200 | 636 | 655 | GCTTCAGCGACATGGTGAGG | 81 | 2626 | 2645 | 93 |
| 564201 | 732 | 751 | GGACATTGGCAGCCGCGGGC | 83 | 2722 | 2741 | 94 |
| 564202 | 929 | 948 | GATTCCATCAAAAGAAATCG | 67 | n/a | n/a | 95 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564203 | 969 | 988 | CAACTGATGTAAGTATATGA | 45 | 47488 | 47507 | 96 |
| 564204 | 1053 | 1072 | CCAAATCACACTTCGGACTG | 74 | n/a | n/a | 97 |
| 564205 | 1073 | 1092 | CTCATGTGCGGCATCAAGTA | 79 | 49247 | 49266 | 98 |
| 564206 | 1138 | 1157 | CATTTGAACAAAATACTCTC | 71 | 49312 | 49331 | 99 |
| 564207 | 1219 | 1238 | CTGATAGCAGAGTCAGTAAA | 72 | 76356 | 76375 | 100 |
| 564208 | 1521 | 1540 | GGGCCACTCGAGCTTTGTAC | 88 | 81681 | 81700 | 101 |
| 564209 | 1628 | 1647 | AGGAATATATTTATTTTCCC | 52 | 83239 | 83258 | 102 |
| 564210 | 1693 | 1712 | CCCATACGCGGTGAATTCTG | 91 | 83304 | 83323 | 103 |
| 564211 | 1713 | 1732 | TGGAGCCCGATCCAGGCTGG | 77 | 83324 | 83343 | 104 |
| 564212 | 1733 | 1752 | AGAAGTGGATCTTGATGGCA | 54 | 83344 | 83363 | 105 |
| 564213 | 1957 | 1976 | GGAGAACCATGAGCAGAGGG | 83 | 85453 | 85472 | 106 |
| 564214 | 2002 | 2021 | GGCCCTTCTGAAGACATGCG | 85 | n/a | n/a | 107 |
| 564215 | 2079 | 2098 | CACTGGATATGGAACCCCTC | 84 | 88189 | 88208 | 108 |
| 564216 | 2099 | 2118 | GTGGGATACAAATTCTAGGC | 94 | 88209 | 88228 | 109 |
| 564217 | 2177 | 2196 | ACTGACCACTGATGACCACG | 67 | 88287 | 88306 | 110 |
| 564218 | 2215 | 2234 | CTGGGTCTATGAGTTTTAGG | 67 | 91099 | 91118 | 111 |
| 564219 | 2291 | 2310 | TGGAATAATACCAGCTTGGG | 84 | 91175 | 91194 | 112 |
| 564220 | 2311 | 2330 | GGCATGGCAACAGCTTCAGT | 81 | 91195 | 91214 | 113 |
| 564221 | 2331 | 2350 | TAGGAGATGCAGCTGGAATA | 71 | 91215 | 91234 | 114 |
| 564222 | 2397 | 2416 | GAAGCCTGGAATCTTTAGCC | 69 | n/a | n/a | 115 |
| 564223 | 2426 | 2445 | CCCTGCAGGAGAGTTCTGCC | 75 | 91696 | 91715 | 116 |
| 564224 | 2582 | 2601 | TTCAGAAGTAGAACTTGGCT | 76 | 112891 | 112910 | 117 |
| 564225 | 2652 | 2671 | CAATTTGTCTTTGATCAAA | 56 | 112961 | 112980 | 118 |
| 564226 | 2757 | 2776 | TGTTACTAAGTATTGAAGGG | 53 | 113066 | 113085 | 119 |
| 564227 | 2787 | 2806 | AAGTGACCTCAGGTCCCCTC | 83 | 113096 | 113115 | 120 |
| 564228 | 2883 | 2902 | ATGTTGATTTCCTAACTTGC | 53 | 114843 | 114862 | 121 |
| 564229 | 3019 | 3038 | GTATAAACTGGAGTTGGCTG | 75 | 115874 | 115893 | 122 |
| 564230 | 3039 | 3058 | GTGCAAAACAAACAGGCTGA | 79 | 115894 | 115913 | 123 |
| 564231 | 3059 | 3078 | GACTGGATACATCATATTTG | 18 | 115914 | 115933 | 124 |
| 564232 | 3082 | 3101 | GGTTGCACGCCTGGGCTCAC | 74 | n/a | n/a | 125 |
| 564233 | 3102 | 3121 | TCATAGGTATTGGGTATAAA | 50 | 116338 | 116357 | 126 |
| 564234 | 3122 | 3141 | TTGATTCACTGGCATGGGCG | 77 | 116358 | 116377 | 127 |
| 564235 | 3180 | 3199 | GATGATGCTGGTCTTGCCGC | 49 | 130944 | 130963 | 128 |
| 564236 | 3373 | 3392 | ATCATTCTAGCATTACCCTG | 61 | 131454 | 131473 | 129 |
| 564237 | 3408 | 3427 | ATACTAAACCAGGCTGGGCG | 71 | 131489 | 131508 | 130 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564238 | 3464 | 3483 | ACATGCATACATCGCATGCG | 32 | n/a | n/a | 131 |
| 564239 | 3505 | 3524 | TAGAAAGAAGGGCTTGTCTC | 67 | 136978 | 136997 | 132 |
| 564240 | 3545 | 3564 | CGCATACTGCTGAGCAAGGG | 79 | 144320 | 144339 | 133 |
| 564241 | 3597 | 3616 | TAGCTGAAGGCTGAGGGTGT | 43 | 144372 | 144391 | 134 |
| 564242 | 3630 | 3649 | CACCATGTTGGCTTTGCTGC | 81 | 144405 | 144424 | 135 |
| 564243 | 3650 | 3669 | ACTGGGTGCAGGATGACTTC | 36 | 144425 | 144444 | 136 |
| 564244 | 3729 | 3748 | CGTGGTAAATGGCTGACTGC | 50 | 145461 | 145480 | 137 |
| 564245 | 3772 | 3791 | TTGGAGGCAGGTGTCATGGA | 36 | 145504 | 145523 | 138 |
| 564246 | 3938 | 3957 | TGGCGCATGGGCAGTTGGAT | 67 | 147853 | 147872 | 139 |
| 564247 | 3994 | 4013 | CTTTGAGCGAGGGCGGCCTG | 29 | 147909 | 147928 | 140 |
| 564248 | 4021 | 4040 | GTCGAGACTGGAATGGGCTG | 54 | 147936 | 147955 | 141 |
| 564249 | 4225 | 4244 | ATTCCTATTGGATGTTACAA | 65 | 148976 | 148995 | 142 |
| 564250 | 4252 | 4271 | ATCTTCCACTGCAAGTGAAC | 77 | 149003 | 149022 | 143 |
| 564251 | 4306 | 4325 | TATGGAATTATGGAATAGCC | 65 | 149057 | 149076 | 144 |
| 564252 | 4433 | 4452 | GCAAGAATCACTCTTGTTAC | 77 | 149184 | 149203 | 145 |
| 564253 | 4581 | 4600 | TGTAGACAGTGATCACCTCA | 77 | 149332 | 149351 | 146 |
| 564254 | n/a | n/a | GGCCAAGGCCCACTTGTCTC | 54 | 3485 | 3504 | 147 |
| 564255 | n/a | n/a | CACTGCGGCCTCGAACAGCA | 81 | 3709 | 3728 | 148 |
| 564263 | n/a | n/a | AAATTCCTCATTTTCTTTTC | 68 | 26924 27239 | 26943 27258 | 149 |
| 564264 | n/a | n/a | GTTATAGTAATCTGTAATCA | 71 | 36133 36239 | 36152 36258 | 150 |
| 564265 | n/a | n/a | AGGATTGTAAAATGATACAG | 47 | 65107 65148 | 65126 65167 | 151 |
| 564266 | n/a | n/a | GTAGGATTGTAAAATGATAC | 64 | 65109 65150 | 65128 65169 | 152 |
| 564267 | n/a | n/a | TTATATATGTAAATTATATC | 9 | 95228 95288 | 95247 95307 | 153 |
| 564268 | n/a | n/a | AACCACTGATTTATACACTT | 88 | 95260 95320 | 95279 95339 | 154 |
| 564269 | n/a | n/a | TTAAAAACCACTGATTTATA | 17 | 95265 95325 | 95284 95344 | 155 |
| 564270 | n/a | n/a | ATATAGCACTCTGCTGTATT | 83 | 99282 99340 | 99301 99359 | 156 |
| 564271 | n/a | n/a | TACCAAGCTTGTGGCTTGGG | 32 | 137342 137420 | 137361 137439 | 157 |
| 564272 | n/a | n/a | TTATACCAAGCTTGTGGCTT | 52 | 137345 137423 | 137364 137442 | 158 |

TABLE 3

Inhibition of ataxin 2 mRNA by 5-10-5
MOE gapmers targeting SEQ ID NO: 3

| ISIS No | SEQ ID NO: 3 Start Site | SEQ ID NO: 3 Stop Site | Sequence | % inhibition | SEQ ID NO |
|---|---|---|---|---|---|
| 564256 | 311 | 330 | CCTCGATGTTCCACAGGCGC | 83 | 159 |
| 564257 | 715 | 734 | GAGTTCACCTGCATCCAGGG | 81 | 160 |
| 564258 | 736 | 755 | TCCAGTTCCCTCATTGGCTG | 27 | 161 |
| 564259 | 771 | 790 | GGTTCCATCCATTAGATACG | 52 | 162 |
| 564260 | 791 | 810 | TTAAACGAAACATATCTTTG | 10 | 163 |
| 564261 | 815 | 834 | GCCCCTGCGCCATAATTTTT | 3 | 164 |
| 564262 | 835 | 854 | ATAAACTGCTTTCAACGGTG | 2 | 165 |

Example 2: Dose-Dependent Antisense Inhibition of Human Ataxin 2 in HepG2 Cells by MOE Gapmers Gapmers from Example 1 exhibiting significant in vitro inhibition of ataxin 2 mRNA were selected and tested at various doses in HepG2 cells. Cells were plated at a density of 20,000 cells per well and transfected using electroporation with 0.625 µM, 1.250 µM, 2.500 µM, 5.000 µM and 10.000 µM concentrations of antisense oligonucleotide, as specified in the Table below. After a treatment period of approximately 16 hours, RNA was isolated from the cells and ataxin 2 mRNA levels were measured by quantitative real-time PCR. Human primer probe set RTS3642 was used to measure mRNA levels. Ataxin 2 mRNA levels were adjusted according to total RNA content, as measured by RIBOGREEN®. Results are presented as percent inhibition of ataxin 2, relative to untreated control cells.

The half maximal inhibitory concentration ($IC_{50}$) of each oligonucleotide is also presented. Ataxin 2 mRNA levels were significantly reduced in a dose-dependent manner in antisense oligonucleotide treated cells.

TABLE 4

Dose response assay

| ISIS No | 0.625 µM | 1.250 µM | 2.500 µM | 5.000 µM | 10.000 µM | $IC_{50}$ (µM) |
|---|---|---|---|---|---|---|
| 564133 | 89 | 95 | 98 | 98 | 97 | <0.6 |
| 564188 | 52 | 72 | 81 | 88 | 90 | <0.6 |
| 564127 | 42 | 62 | 65 | 85 | 91 | 0.8 |
| 564150 | 39 | 63 | 74 | 86 | 91 | 0.8 |
| 564143 | 37 | 60 | 76 | 84 | 94 | 0.9 |
| 564122 | 25 | 53 | 69 | 85 | 88 | 1.3 |
| 564126 | 23 | 48 | 61 | 78 | 89 | 1.7 |
| 564144 | 12 | 35 | 53 | 71 | 85 | 2.4 |
| 564135 | 22 | 35 | 53 | 73 | 86 | 2.1 |
| 564125 | 33 | 44 | 64 | 78 | 85 | 1.5 |
| 564129 | 31 | 42 | 54 | 71 | 77 | 1.9 |
| 564216 | 50 | 67 | 82 | 86 | 94 | <0.6 |
| 564210 | 33 | 48 | 72 | 80 | 94 | 1.3 |
| 564208 | 30 | 40 | 67 | 75 | 87 | 1.6 |
| 564268 | 35 | 52 | 69 | 81 | 85 | 1.2 |

Example 3: Antisense Inhibition of Human Ataxin 2 in a SCA2 BAC Mouse Model

Gapmers from Example 1 exhibiting significant in vitro inhibition of ataxin 2 mRNA were selected and tested in vivo in a SCA2[Q22]-BAC mouse model. This mouse model was created in the Pulst laboratory (University of Utah, Salt Lake City), using mice of FVB/B6 hybrid background, for the study of spinocerebella ataxia type 2 (SCA2). These mice possess the entire 176 kb human ATXN2 gene region, including the 16 kb upstream sequence and the 2.5 kb downstream sequence.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 µL mark with either normal saline (0.9%) or antisense oligonucleotide (250 µg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 µL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 µL consisting of 15 ng cDNA, 2 µL of each primer (0.3 µM final), and 10 µL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis.

The results from the RNA analysis for mouse and human ataxin 2 are presented in the Table below. As indicated, some of the ISIS oligonucleotides decreased human ataxin 2 mRNA in the brains of the mice.

TABLE 5

Percent inhibition of ataxin 2 mRNA compared to
the saline (0.9%) control in SCA[Q22]-BAC mice

| ISIS No | Human ataxin 2 | Mouse ataxin 2 |
|---|---|---|
| 564122 | 10 | 15 |
| 564127 | 46 | 65 |
| 564133 | 60 | 62 |
| 564150 | 21 | 53 |
| 564188 | 9 | 23 |
| 564216 | 21 | 55 |

Example 4: Antisense Inhibition of Human Ataxin 2 in an ATXN2-Q127 Mouse Model

Gapmers from Example 1 exhibiting significant in vitro inhibition of ataxin 2 mRNA were selected and tested in vivo in an ATXN2-Q127 mouse model. This mouse model (Hansen, S. T. et al., Human. Molecular Genetics 2012. 1-13) expresses the full-length-mutant ATXN2$^{Q127}$ complementary DNA under the regulation of the Purkinje cell protein-2 (Pcp2) promoter. This model shows an early-onset progressive motor impairment phenotype accompanied by the formation of diffuse cytoplasmic aggregates in cerebellar Purkinje cells.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 μL mark with either normal saline (0.9%) or antisense oligonucleotide (250 μg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 μL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 μl, consisting of 15 ng cDNA, 2 μL of each primer (0.3 μM final), and 10 μL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis. All mRNA levels were normalized to the housekeeping gene, actin.

The results from the RNA analysis for mouse and human ataxin 2 are presented in the Table below. As indicated, some of the ISIS oligonucleotides decreased human ataxin 2 mRNA in the brains of the mice.

qPCR analysis of the marker for microgliosis, AIF/Ibal, to measure inflammation, was also performed. The results are presented in the Table below.

TABLE 6

Percent inhibition of ataxin 2 mRNA compared to
the saline (0.9%) control in ATXN2-Q127 mice

| ISIS No | Human | Mouse |
|---|---|---|
| 564133 | 64 | 52 |
| 564127 | 62 | 49 |
| 564216 | 46 | 40 |
| 564210 | 39 | 48 |

TABLE 7

Percent Iba1 mRNA level increase compared to
the saline (0.9%) control in ATXN2-Q127 mice

| ISIS No | Iba1 |
|---|---|
| 564133 | 9 |
| 564127 | 49 |
| 564216 | 16 |
| 564210 | 96 |

Example 4: Dose-Dependent Antisense Inhibition of Human Ataxin 2 in an ATXN2-Q127 Mouse Model ISIS 564133 was tested in different doses in the ATXN2-Q127 mouse model.

Treatment

Groups of 3 mice each were administered normal saline (0.9%) or ISIS 564133 via intracerebroventricular injections dosed at 50 μg, 100 μg, 200 μg, 250 μg, or 300 μg. The mice were administered in the same manner as described in the studies above and monitored daily.

RNA Analysis

After 7 days, the mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for mouse and human ataxin 2 are presented in the Table below.

TABLE 8

Percent inhibition of ataxin 2 mRNA compared to the saline (0.9%) control in ATXN2-Q127 mice

| Dose (μg) | Human ataxin 2 | Mouse ataxin 2 |
|---|---|---|
| 50 | 60 | 47 |
| 100 | 84 | 35 |
| 200 | 85 | 67 |
| 250 | 79 | 62 |
| 300 | 73 | 41 |

Example 5: Time-Dependent Antisense Inhibition of Human Ataxin 2 in an ATXN2-Q127 Mouse Model ISIS 564133 was administered and mRNA level reduction was tested in different time points in the ATXN2-Q127 mouse model.

Treatment

Groups of 3 mice each were administered normal saline (0.9%) or ISIS 564133 via intracerebroventricular injections dosed at 200 μg. The mice were administered in the same manner as described in the studies above and monitored daily.

RNA Analysis

After 9 days, 18 days, 27 days, and 84 days, groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for human ataxin 2 are presented in the Table below. Western analysis of the corresponding protein samples was performed and confirmed the qPCR results.

TABLE 9

Ataxin 2 mRNA levels in ATXN2-Q127 mice

| Time Point | ATXN2 expression relative to actin |
|---|---|
| saline (0.9%) control | 8.4 |
| 9 days | 2.9 |
| 18 days | 0.9 |
| 27 days | 1.4 |
| 84 days | 2.7 |

Immunohistochemical staining of cerebellar Purkinje cells on day 7 was performed using rabbit anti-oligonucleotide antibody generated in-house. The results demonstrated that ISIS oligonucleotide localized in cerebellar Purkinje cells of ATXN-Q127 mice.

Example 6: Effect of Antisense Inhibition of Human Ataxin 2 in an ATXN2-Q127 Mouse Model ISIS oligonucleotide was administered in the ATXN2-Q127 mouse model and wild-type mice. On day 3, motor performance was evaluated using the rotarod test.

Groups of ATXN2-Q127 mice were administered normal saline (0.9%) or ISIS 564133 at 50 μg, 100 μg, or 200 μg via intracerebroventricular injections in the same manner as described in the studies above. Groups of wild-type mice were administered normal saline (0.9%) or ISIS oligonucleotide at 200 μg via intracerebroventricular injections dosed in the same manner as described in the studies above. Groups of ATXN2-Q127 mice were administered normal saline (0.9%) or ISIS 546127 or ISIS 564216 at 200 μg via intracerebroventricular injections dosed in the same manner as described in the studies above. After 6 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20%.

TABLE 10

Rotarod performance test in ATXN2-Q127 mice

| Strain of mice | Number of mice | Treatment | Latency to fall (seconds) |
|---|---|---|---|
| WT | 10 | saline (0.9%) control | 199 |
|  | 10 | ISIS 564133 (200 μg) | 189 |
| ATXN-Q127 | 8 | saline (0.9%) control | 127 |
|  | 15 | ISIS 564133 (50 μg) | 149 |
|  | 16 | ISIS 564133 (100 μg) | 141 |
|  | 9 | ISIS 564133 (200 μg) | 100 |
| ATXN-Q127 | 15 | saline (0.9%) control | 130 |
|  | 13 | ISIS 564127 (200 μg) | 150 |
|  | 15 | ISIS 564216 (200 μg) | 156 |

Example 7: Effect of Antisense Inhibition of Human Ataxin 2 in an ATXN2-Q127 Mouse Model ISIS oligonucleotide was administered in the ATXN2-Q127 mouse model and wild-type mice. Cerebellar expression of ataxin 2, as well as several Purkinje cell (PC) genes, was assessed.

Groups of ATXN2-Q127 mice were administered normal saline (0.9%) or ISIS 564133 at 200 μg via intracerebroventricular injections dosed in the same manner as described in the studies above. Groups of wild-type mice were administered normal saline (0.9%) or ISIS 564133 at 200 μg via intracerebroventricular injections dosed in the same manner as described in the studies above. After 5 weeks, the mice were euthanized and cerebellar expression of various gene mRNA levels was assessed.

RNA Analysis

Groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin. RNA levels of human ataxin 2, murine ataxin 2, Pcp2, Calb1, Rgs8, and Fam107b were measured. Transcription changes in several of these PC-specific genes have been demonstrated to progressively decrease in models of SCA2 (Hansen, S. T. et al., Hum. Mol. Genet. 2013. 22: 271-283).

The results from the RNA analysis are presented in the Table below and demonstrate that treatment with ISIS oligonucleotides targeting ataxin 2 increased the expression levels of all the PC-specific genes compared to the transgenic control group.

TABLE 11

PC-specific mRNA levels in ATXN2-Q127 mice

|  | WT | ATXN-Q127 | |
| --- | --- | --- | --- |
|  | saline (0.9%) control | saline (0.9%) control | ISIS 564133 (200 µg) |
| human ataxin 2 | 0.21 | 3.57 | 1.31 |
| murine ataxin 2 | 0.79 | 0.84 | 0.6 |
| Pcp2 | 0.77 | 0.36 | 0.48 |
| Rgs8 | 1.45 | 0.25 | 0.35 |
| Calb1 | 1.14 | 0.5 | 0.71 |
| Fam107b | 1.41 | 0.7 | 0.9 |

Example 8: Effect of Antisense Inhibition of Human Ataxin 2 in an ATXN2-Q127 Mouse Model ISIS oligonucleotide was administered in the ATXN2-Q127 mouse model and wild-type mice. Motor performance was evaluated using the rotarod test.

Groups of ATXN2-Q127 mice (7.5 weeks of age) were administered normal saline (0.9%) or ISIS 546127 or ISIS 564216 at 200 µg via intracerebroventricular injections dosed in the same manner as described in the studies above. After 5 weeks and 9 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20% on week 5 and about 27% on week 9.

TABLE 12

Rotarod performance test in ATXN2-Q127 mice. (mean latency to fall, in seconds)

| Weeks after injection | | ISIS 564127 | ISIS 564216 | Saline control |
| --- | --- | --- | --- | --- |
| Week 5 | DAY 3 | 137 | 145 | 123 |
|  | DAY 4 | 140 | 141 | 119 |
|  | DAY 5 | 155 | 154 | 131 |
| Week 9 | DAY 3 | 131 | 149 | 104 |
|  | DAY 4 | 125 | 139 | 104 |
|  | DAY 5 | 134 | 139 | 112 |

Example 9: Effect of Antisense Inhibition of Human Ataxin 2 in an ATXN2-Q127 Mouse Model ISIS oligonucleotide was administered in the ATXN2-Q127 mouse model. Motor performance was evaluated using the rotarod test.

Seven week old ATXN2-Q127 mice were subjected to the rotarod test, then divided into two groups of 30 mice each, such that average rotarod performance, average weights, and sex composition were equal across both groups. At 8 weeks of age, one group of mice received normal saline via intracerebroventricular (ICV) injection and one group received ISIS 564216 at 210 µg via ICV injection, dosed in the same manner as described in the studies above. Five weeks later (13 weeks of age), the mice were again subjected to the rotarod test. Six weeks post injection (14 weeks of age), the mice received a second ICV injection, identical to the injection received at 8 weeks of age. Five weeks later (19 weeks of age, 11 weeks after the first ICV injection), the mice were subjected to a third rotarod test.

Rotarod Test

The accelerating rotarod test was performed on the Rotamex rotarod. Rotarod testing was conducted over five days. On the first day, mice were acclimated to the technician by being handled by the technician three times, 5 minutes each time. On the second day, mice were introduced to the rotarod three times, 10 minutes each time at a speed ranging from 0 to 10 RPM. On each of days 3-5, mice were placed on the rotarod at a speed of 0 RPM, then the rotarod was accelerated to 40 RPM over 6 minutes, and this was done for each mouse three times. The three total trials per day were used to calculate a mean value of "latency to fall" per day, in seconds. Latency to fall is defined as the amount of time before the animal falls from the rotarod. It was recorded automatically, when the mouse no longer interrupted infrared beams directed above the rotarod. The time to first passive rotation (when mice stop walking and hold on and revolve with the rod) is also automatically recorded, and generally reflects the latency to fall time.

The results from the rotarod test are presented as the average for each treatment group in the Table below. As shown in the Table below, treatment with ASO improved rotarod performance.

TABLE 13

Rotarod performance test in ATXN2-Q127 mice

| Treatment | Weeks after 1st injection | Weeks after 2nd injection | Testing day | Latency to fall (s) |
|---|---|---|---|---|
| Saline | 5 | n/a | 3 | 218.5 |
|  |  |  | 4 | 240.9 |
|  |  |  | 5 | 236.5 |
| Isis No. 564216 | 5 | n/a | 3 | 240.6 |
|  |  |  | 4 | 257.9 |
|  |  |  | 5 | 259.6 |
| Saline | 11 | 5 | 3 | 216.2 |
|  |  |  | 4 | 198.7 |
|  |  |  | 5 | 212.1 |
| Isis No. 564216 | 11 | 5 | 3 | 194.4 |
|  |  |  | 4 | 226.0 |
|  |  |  | 5 | 242.8 |

What is claimed is:

1. A method comprising administering a single-stranded modified oligonucleotide consisting of 12 to 30 linked nucleosides, wherein the modified oligonucleotide is at least 90% complementary to an Ataxin 2 nucleic acid to an animal for treating an Ataxin 2 associated disease, wherein the modified oligonucleotide is not complementary to a CAG repeat expansion in the Ataxin 2 nucleic acid.

2. A method comprising:
identifying an animal having an Ataxin 2 associated disease; and
administering a single-stranded modified oligonucleotide consisting of 12 to 30 linked nucleosides, wherein the modified oligonucleotide is at least 90% complementary to an Ataxin 2 nucleic acid, wherein the modified oligonucleotide is not complementary to a CAG repeat expansion in the Ataxin 2 nucleic acid.

3. The method of claim 1, wherein the Ataxin 2 associated disease is a neurodegenerative disease.

4. The method of claim 3, wherein the neurodegenerative disease is spinocerebellar ataxia type 2 (SCA2), amyotrophic lateral sclerosis (ALS), or parkinsonism.

5. The method of claim 1, wherein the animal is a human.

6. The method of claim 5, wherein the administering is parenteral administration.

7. The method of claim 6, wherein the parenteral administration is any of intrathecal administration or intracerebroventricular administration.

8. The method of claim 6, wherein the administering distributes the antisense compound to the Purkinje cells.

9. The method of claim 6, wherein the administering improves rotarod performance.

10. The method of claim 9, wherein rotarod performance is improved by 10 percent, 15 percent, or 20 percent.

11. The method of claim 6, wherein the administering improves motor function.

12. The method of claim 11, wherein motor function is improved by 10 percent, 15 percent, or 20 percent.

13. The method of claim 5, wherein at least one symptom of an Ataxin 2 associated disease is ameliorated, treated, prevented, or slowed.

14. The method of claim 1, wherein the Ataxin 2 nucleic acid has the sequence of any of SEQ ID NO: 1, SEQ ID NO: 2, or SEQ ID NO: 3.

15. The method of claim 14, wherein at least one internucleoside linkage of the modified oligonucleotide is a modified internucleoside linkage.

16. The method of claim 15, wherein at least one modified internucleoside linkage is a phosphorothioate internucleoside linkage.

17. The method of claim 16, wherein each modified internucleoside linkage is a phosphorothioate internucleoside linkage.

18. The method of claim 14, wherein at least one nucleoside of the modified oligonucleotide comprises a modified nucleobase.

19. The method of claim 18, wherein the modified nucleobase is a 5-methylcytosine.

20. The method of claim 14, wherein at least one nucleoside of the modified oligonucleotide comprises a modified sugar.

21. The method of claim 20, wherein the at least one modified sugar is a bicyclic sugar.

22. The method of claim 21, wherein the bicyclic sugar comprises a chemical bridge between the 2' and 4' position of the sugar, wherein the chemical bridge is selected from: 4'-$CH_2$-O-2'; 4'-$CH(CH_3)$-O-2'; 4'-$(CH_2)_2$-O-2'; and 4'-$CH_2$-N(R)-O-2' wherein R is, independently, H, $C_1$-$C_{12}$ alkyl, or a protecting group.

23. The method of claim 20, wherein at least one modified sugar comprises a 2'-O-methoxyethyl group.

24. The method of claim 14, wherein the modified oligonucleotide is a gapmer.

25. The method of claim 1, wherein the modified oligonucleotide is at least 95% complementary to an Ataxin 2 nucleic acid.

26. The method of claim 1, wherein the modified oligonucleotide is at least 97% complementary to an Ataxin 2 nucleic acid.

27. The method of claim 1, wherein the modified oligonucleotide is 100% complementary to an Ataxin 2 nucleic acid.

28. The method of claim 2, wherein the modified oligonucleotide is at least 95% complementary to an Ataxin 2 nucleic acid.

29. The method of claim 2, wherein the modified oligonucleotide is at least 97% complementary to an Ataxin 2 nucleic acid.

30. The method of claim 2, wherein the modified oligonucleotide is 100% complementary to an Ataxin 2 nucleic acid.

* * * * *

SEQUENCE LISTING

<160> NUMBER OF SEQ ID NOS: 165

<210> SEQ ID NO 1
<211> LENGTH: 4712
<212> TYPE: DNA
<213> ORGANISM: Homo sapiens

<400> SEQUENCE: 1

```
accccgaga aagcaaccca gcgcgccgcc cgctcctcac gtgtccctcc cggccccggg      60
gccacctcac gttctgcttc cgtctgaccc ctccgacttc cggtaaagag tccctatccg     120
cacctccgct cccacccggc gcctcggcgc gcccgccctc cgatgcgctc agcggccgca    180
gctcctcgga gtcccgcgt ggccaccgag tctcgccgct tcgccgcagc caggtggccc     240
gggtggcgct cgctccagcg gccggcgcgg cggagcgggc ggggcggcgg tggcgcggcc     300
ccgggaccgt atccctccgc cgcccctccc ccgcccggcc ccgccccc tccctcccgg      360
cagagctcgc ctccctccgc ctcagactgt tttggtagca acggcaacgg cggcggcgcg    420
tttcggcccg gctcccggcg gctccttggt ctcggcgggc ctcccccgccc cttcgtcgtc    480
ctccttctcc ccctcgccag cccgggcgcc cctccggccg cgccaacccg cgcctccccg    540
ctcggcgccc gcgcgtcccc gccgcgttcc ggcgtctcct ggcgcgcgcc ggctcccggc     600
tgtccccgcc cggcgtgcga gccggtgtat gggcccctca ccatgtcgct gaagccccag    660
cagcagcagc agcagcagca gcagcagcag cagcagcaac agcagcagca gcagcagcag    720
cagcagccgc cgcccgcggc tgccaatgtc cgcaagcccg gcggcagcgg ccttctagcg    780
tcgccgccc cgcgccttc gccgtcctcg tcctcggtct cctcgtcctc ggccacggct    840
ccctcctcgg tggtcgcggc gacctccggc ggcgggaggc ccggcctggg cagaggtcga    900
aacagtaaca aaggactgcc tcagtctacg atttcttttg atggaatcta tgcaaatatg    960
aggatggttc atatacttac atcagttgtt ggctccaaat gtgaagtaca agtgaaaaat   1020
ggaggtatat atgaaggagt ttttaaaact tacagtccga agtgtgattt ggtacttgat   1080
gccgcacatg agaaaagtac agaatccagt tcggggccga acgtgaaga aataatggag    1140
agtattttgt tcaaatgttc agactttgtt gtggtacagt ttaaagatat ggactccagt   1200
tatgcaaaaa gagatgcttt tactgactct gctatcagtg ctaaagtgaa tggcgaacac   1260
aaagagaagg acctggagcc ctgggatgca ggtgaactca cagccaatga ggaacttgag   1320
gctttggaaa atgacgtatc taatgatggg atcccaatg atatgtttcg atataatgaa    1380
gaaaattatg gtgtagtgtc tacgtatgat agcagtttat cttcgtatac agtgcccta    1440
gaaagagata actcagaaga attttaaaaa cgggaagcaa gggcaaacca gttagcagaa   1500
gaaattgagt caagtgccca gtacaaagct cgagtggccc tggaaaatga tgataggagt   1560
```

-continued

```
gaggaagaaa aatacacagc agttcagaga aattccagtg aacgtgaggg gcacagcata    1620
aacactaggg aaaataaata tattcctcct ggacaaagaa atagagaagt catatcctgg    1680
ggaagtggga gacagaattc accgcgtatg ggccagcctg gatcgggctc catgccatca    1740
agatccactt ctcacacttc agatttcaac ccgaattctg gttcagacca aagagtagtt    1800
aatggaggtg ttccctggcc atcgccttgc ccatctcctt cctctcgccc accttctcgc    1860
taccagtcag gtcccaactc tcttccacct cgggcagcca cccctacacg gccgccctcc    1920
aggcccccct cgcggccatc cagacccccg tctcacccct ctgctcatgg ttctccagct    1980
cctgtctcta ctatgcctaa acgcatgtct tcagaagggc ctccaaggat gtccccaaag    2040
gcccagcgac atcctcgaaa tcacagagtt tctgctggga ggggttccat atccagtggc    2100
ctagaatttg tatcccacaa cccacccagt gaagcagcta ctcctccagt agcaaggacc    2160
agtccctcgg ggggaacgtg gtcatcagtg gtcagtgggg ttccaagatt atcccctaaa    2220
actcatagac ccaggtctcc cagacagaac agtattggaa ataccccag tgggccagtt    2280
cttgcttctc cccaagctgg tattattcca actgaagctg ttgccatgcc tattccagct    2340
gcatctccta cgcctgctag tcctgcatcg aacagagctg ttaccccttc tagtgaggct    2400
aaagattcca ggcttcaaga tcagaggcag aactctcctg cagggaataa agaaaatatt    2460
aaacccaatg aaacatcacc tagcttctca aaagctgaaa acaaaggtat atcaccagtt    2520
gtttctgaac atagaaaaca gattgatgat ttaaagaaat ttaagaatga ttttaggtta    2580
cagccaagtt ctacttctga atctatggat caactactaa acaaaaatag agagggagaa    2640
aaatcaagag atttgatcaa agacaaaatt gaaccaagtg ctaaggattc tttcattgaa    2700
aatagcagca gcaactgtac cagtggcagc agcaagccga atagccccag catttcccct    2760
tcaatactta gtaacacgga gcacaagagg ggacctgagg tcacttccca aggggttcag    2820
acttccagcc cagcatgtaa acaagagaaa gacgataagg aagagaagaa agacgcagct    2880
gagcaagtta ggaaatcaac attgaatccc aatgcaaagg agttcaaccc acgttccttc    2940
tctcagccaa agccttctac taccccaact tcacctcggc ctcaagcaca acctagccca    3000
tctatggtgg gtcatcaaca gccaactcca gtttatactc agcctgtttg ttttgcacca    3060
aatatgatgt atccagtccc agtgagccca ggcgtgcaac ctttatcccc aataccatg    3120
acgcccatgc cagtgaatca agccaagaca tatagagcag taccaaatat gccccaacag    3180
cggcaagacc agcatcatca gagtgccatg atgcacccag cgtcagcagc gggcccaccg    3240
attgcagcca ccccaccagc ttactccacg caatatgttg cctacagtcc tcagcagttc    3300
ccaaatcagc cccttgttca gcatgtgcca cattatcagt ctcagcatcc tcatgtctat    3360
agtcctgtaa tacagggtaa tgctagaatg atggcaccac caacacacgc ccagcctggt    3420
ttagtatctt cttcagcaac tcagtacggg gctcatgagc agacgcatgc gatgtatgca    3480
tgtcccaaat taccatacaa caaggagaca agcccttctt tctactttgc catttccacg    3540
ggctcccttg ctcagcagta tgcgcaccct aacgctaccc tgcacccaca tactccacac    3600
cctcagcctt cagctacccc cactggacag cagcaaagcc aacatggtgg aagtcatcct    3660
gcacccagtc ctgttcagca ccatcagcac caggccgccc aggctctcca tctgccagt    3720
ccacagcagc agtcagccat ttaccacgcg gggcttgcgc caactccacc ctccatgaca    3780
cctgcctcca acacgcagtc gccacagaat agtttcccag cagcacaaca gactgtcttt    3840
acgatccatc cttctcacgt tcagccgcg tataccaacc caccccacat ggcccacgta    3900
cctcaggctc atgtacagtc aggaatggtt ccttctcatc caactgccca tgcgccaatg    3960
```

| | | | | |
|---|---|---|---|---|
| atgctaatga | cgacacagcc | acccggcggt | ccccaggccg | ccctcgctca aagtgcacta | 4020 |
| cagcccattc | cagtctcgac | aacagcgcat | tccccctata | tgacgcaccc ttcagtacaa | 4080 |
| gcccaccacc | aacagcagtt | gtaaggctgc | cctggaggaa | ccgaaaggcc aaattccctc | 4140 |
| ctcccttcta | ctgcttctac | caactggaag | cacagaaaac | tagaatttca tttatttgt | 4200 |
| ttttaaaata | tatatgttga | tttcttgtaa | catccaatag | gaatgctaac agttcacttg | 4260 |
| cagtggaaga | tacttggacc | gagtagaggc | atttaggaac | ttgggggcta ttccataatt | 4320 |
| ccatatgctg | tttcagagtc | ccgcaggtac | ccagctctg | cttgccgaaa ctggaagtta | 4380 |
| tttatttttt | aataacccctt | gaaagtcatg | aacacatcag | ctagcaaaag aagtaacaag | 4440 |
| agtgattctt | gctgctatta | ctgctaaaaa | aaaaaaaaa | aaaaaatcaa gacttggaac | 4500 |
| gccccttttac | taaacttgac | aaagtttcag | taaattctta | ccgtcaaact gacgattat | 4560 |
| tatttataaa | tcaagtttga | tgaggtgatc | actgtctaca | gtggttcaac ttttaagtta | 4620 |
| agggaaaaac | ttttacttg | tagataatat | aaaataaaaa | cttaaaaaaa atttaaaaaa | 4680 |
| taaaaaaagt | tttaaaaact | gaaaaaaaaa | aa | | 4712 |

<210> SEQ ID NO 2
<211> LENGTH: 151001
<212> TYPE: DNA
<213> ORGANISM: Homo sapiens

<400> SEQUENCE: 2

| | | | | |
|---|---|---|---|---|
| tcccaaagtg | ctgggattac | aggcgtgagc | caccacactg | gccaaaactt gttcttaaga | 60 |
| ttgtattctg | ggaccttgat | tccaatcaga | gaaaagtgat | tgtatttttt tattttttatt | 120 |
| tttttttagat | aaagtttcgc | tcttgttgcc | caggctggag | tgcagtggtg ccctcttttgg | 180 |
| tcactgtaac | ctccgcctcc | tgggttcaag | cgattctcct | gcctcagcat cctgcgtagc | 240 |
| tgagatcaca | gatgcccacc | accacgccca | gctaatttttt | tcgtattttt agtagcgatg | 300 |
| gggtttcacc | atgttggcca | cgctggtctt | gaactcctga | cctcaggtga tccatccgcc | 360 |
| tcggcctccc | agagtgctgg | gattacaggt | gtgagccacc | gcgccaggcc aagtgttttgt | 420 |
| atttctatta | agaaagaat | ataacgggac | accattgacg | acctgctcca ttgcaggcct | 480 |
| ccttgctgtt | cctcagactc | ccccctcaga | gcctttgccc | tcgctgtgcc ctccacctgg | 540 |
| agcgtttctc | cccaggatcc | tcatgcccat | gctcatttgg | gtccctgccc catgtcaccc | 600 |
| tctccaggag | cttcccctca | cagcagccct | ggcctgtacc | acagccgggt acaggtattt | 660 |
| ttttgtttca | actggttttt | tagttccagt | ttcctttagg | ttactttatt tatttatttta | 720 |
| tttatttatt | ttttgagacg | gagtctcgct | ctgtcgccca | ggctggagtg catgatctcg | 780 |
| gctgactgca | acctccacct | cccggattca | agcaattctc | ctgtatcagc ctcccgagta | 840 |
| gctgggatta | caggcgccca | ccaccacacc | cggctaattt | ttatatttttt ggtagagacg | 900 |
| gggtttcacc | atgttggcta | ggctaggtta | ttttttaaag | gttttgcaa tggtcccttg | 960 |
| atctactttt | taccttagat | gggaaataaa | actgatttcc | tacattggca gaatacaatg | 1020 |
| atcattttttg | cctggactat | ctaggaggtt | aatttcagtt | ggactactga aaactgctgg | 1080 |
| ttcaatcatt | ctccacgttt | atctaagtct | ttaccttttat | ctggacagtt ctaggacatt | 1140 |
| gaggggaatt | ttggtgtttc | ttccccctatt | atttcctgaa | gtcatttcac tttaaaaaac | 1200 |
| aatagattca | ctgctcaaaa | aaaaaaaaaa | aagttaccta | cttttctactt gcttccagtt | 1260 |
| taactgcaac | acattttaaa | aagagtctac | tgtgctggct | gggtaagtta aattaaaact | 1320 |

```
tctaaagggt ccaaggtcta aagttcgcac attgttttga ggtcggctct gtctctaccg    1380
agggagatcc cattatccgt agttctacca gtcccaatcc catatatttc ctttagaatc    1440
tcatgaatga ggaaaaagaa gttcaagtga gggaacatag gttcaaatga aggtcagata    1500 cctaaaaagag ttttctggtg actgtgcgcg gctggggtgg aaaaagtggg gaaaaggtac    1560
ccagatgtgg gtggccccgg agggttgctc cactccagcc ccggcagggc aggacagcgc    1620
ggcctgcctg gtagatgccc cgagccactg gagcgcctac tgtgtggcgg gcggggacg    1680 gcaggaaaac ggcaggatgc tgtgtcccct gaatctggca gggttctagg tgctttacac    1740
gtagcaagac acattctccg ccccaaggca ctcgcagtca gtccattttc tgggttgcat    1800 caggtgggggg caaactaggt ccccgcagaa gtgaagatgc tgaaggaata cagtaggaga    1860
agaaatgctt ctctcctgtc ctccacacca ggcaggcccc agaggctgag accgacacgc    1920
cctccccgaa gggcagaccc gccttgagga aggcggatcc gggtagggac cgccgcctgg    1980
ccctcacccg accccgaga aagcaaccca gcgcgccgcc cgctcctcac gtgtccctcc    2040
cggcccgggg gccacctcac gttctgcttc cgtctgaccc ctccgacttc cggtaaagag    2100
tccctatccg cacctccgct cccacccggc gcctcggcgc gcccgccctc cgatgcgctc    2160
agcggccgca gctcctcgga gtcccgcggt ggccaccgag tctcgccgct cgccgcagc    2220 caggtggccc gggtggcgct cgctccagcg gccggcgcgg cggagcgggc ggggcggcgg    2280
tggcgcggcc ccgggaccgt atccctccgc cgccctccc ccgccggcc ccggcccccc    2340 tccctccccgg cagagctcgc ctccctccgc ctcagactgt tttggtagca acggcaacgg    2400
cggcggcgcg tttcggcccg gctcccgcg gctccttggt tcggcgggc ctccccgccc    2460 cttcgtcgtc ctccttctcc ccctcgccag cccgggcgcc cctccggccg cgccaacccg    2520
cgcctccccg ctcggcgccc gcgcgtcccc ccgcgttcc ggcgtctcct tggcgcgcc    2580 ggctcccggc tgtccccgcc cggcgtgcga ccggtgtat gggcccctca ccatgtcgct    2640 gaagcccag cagcagcagc agcagcagca gcagcagcag cagcagcaac agcagcagca    2700
gcagcagcag cagcagccgc cgcccgcggc tgccaatgtc cgcaagcccg cggcagcgg    2760 ccttctagcg tcgcccgccg ccgcgccctt gccgtcctcg tcctcggtct cctcgtcctc    2820
ggccacggct ccctcctcgg tggtcgcggc gacctccggc ggcgggaggc ccggcctggg    2880
caggtgggtg tcggcacccc agccccctcc gctccgggcc cggcgtcccc tccccgcgg    2940 cccgcgccgc cgtccccgcc ccgtgacccg ccgggctacc cggggtgggc tgggggccgg    3000
cagcgcgggg gagactcgct cgggcctgag ccccgaggct cggccggtgg gcgcagccgg    3060
ggtcctctgg gattgtcagg cctgtccagc ctcccgcagc atcccgcccc cctccccggg    3120
cggtcaagat ggagggagcg gcggcctcc cctccccacg cgtgttggga ggggttctcg    3180
ggtagcggcg atggtcagcc ccggctcccc cttccgcacg atcctccgcc cgcagcgtgg    3240
ggatgctcgg gcagctcctc cactcccggt ttaggtgtga acgttggagg ggtctggagg    3300
ctgtggtggc gttttccgga acatgtcccc ctccatgggg gacatctctg gaggggagaa    3360
gttagggccg cgtccccgt gccggttaaa ggggtaggca ccgggctcct ccggaatcat    3420
cagggtctgt cggggctctc tccccgcccc tccgagtcc tgggaaagat cggaggacgg    3480
ggtggagaca agtgggcctt ggcccccgca cccctctgcg ttcgtgtccg aggcggcggc    3540
gggggctccc gaactcccct gaaatcgtgg ggctccatgt ggcctccggc agcgttccac    3600
cctcccccac ctggggaagg gaaggggtgg ggagtgcccg gccccgtccc ggccttcctc    3660
cttcccccgc cagacctctc cggcgcgcgg gtggtggccg atccgcattg ctgttcgagg    3720
```

```
ccgcagtgga gaaggcgcct gtggaacatc ggtgggtgag ggctggaccc aggctggacc    3780
ctggagatcc ggggtggcgg tgctggtggc aggggggcggg caccctgcgc acttatccca   3840 accccccgccc caatttcgga aatgctagga gagagagatt gcagcagggg acgtggtcgg   3900
gttcctgaag gcagaaaggc gggtgtttac tagcgtcttt ttccctccta agccggggtt   3960
gtagtagggg ctgggggctc agtgttgtcc cggctaactg ggtttgactc gagggtgtgt   4020
ttgtgcagga gggcctgttg ggggtggcgg gcggttgtca gttcgtattt cacgaactaa   4080
gaaaatgctt agtgttcaaa gggagaagga aacgtcaata gactccattc cattgtggcc   4140
ggtgtcctta acttcgggag tgccgccaga gcttaccaag ggcacgcaag tccatttccc   4200
ttgtgcctca agtccatccg tgttgtaggc actactgtgc cttctttagg cctaggccgc   4260
cggcttgacg gcgggtgacc ggcgtcctcc ttaaataggc atcttgggct ttggaaggtg   4320
gaataagagg attttcatt cacccgagtt ttctttttga aaacacattt tcagcaaccc    4380
atttccaaag aattttatt tacagcagaa attccccatc aagaggaatc agctggtttt    4440
taaggaattc tgctgccttc aaaggggcg gaaacagtcg gttatttgac tttacacgcc    4500 ccgcccccc ttcccttct ctgagtctga agcatcccaa acactactta gccaaactag     4560
ttcagatgaa gtgatcgttt ccccaagtag ggtaacttca gtttcccttt ttcgttggca   4620
tctagcgaaa aatgaaaaaa tttaaaatac aactttata gaaaggatg tattctgttt     4680 ttactttctt aggtattagg aagagatttg gcagataatt caacatgttc aaatatataa   4740
acattaaaac taaggttatt aagttgcatt gactactagg cttaaaaatt agattataag   4800
agaatttgct cctgagtagt ttgagtgatc aaagatattt ggaatgtttt agtaccacaa   4860
ggtctttttt ctgttccttg aggctttaca acaatttaag gttaatttag attttcctt    4920 gctttaagtt cttttacttg agacctaaat ggcagcccct attctttctg atgaataggt   4980
gaaattttgt ttactgtgtt ggatttgtgt aatgtgaagt tttattcttg aacagatcgt   5040
taatgtactt gtagaattac tttgaatttg aatcactttc ctgcattcct tgtaaataag   5100
tttcagcttc tagaatctcc tcacttaggt ttgtgcgtat caacagtgaa aataagtctc   5160
tgagagcaag ggtgaaaaaa aatgcagcat tcggtttgac aagtttcgag atagcaaaat   5220
atgcttgaaa gtctggaaat tcacatctgc tttaagaaac atttcataat ttgactttgt   5280
gtgtgtgtgt gtgaatagtt tttcatgact ttcagaagtg atttatttg ttctttgtta    5340 tatatatttt tgaaggtggc tgttttagga aagataatgt aatcacaata ttagaacata   5400 atttactgt aatctaattt tgtgtgtgtg tgtgtgtgtg tgtgtgtgtg tgtgtgtgtg    5460
ttttggatgg aatctcactc tgtcgcccag gctggagtgc agtggcctga tctcagctta   5520
ctgcagtctc tgtctcctgg gttcatttaa gtgattctcc agcctcagcc tccccagtag   5580
ctgggattac aggttcgtgc taccacacct ggctaatttt tttgtatttt tagtgaggac   5640
gggattttgc catgttggcc aggctggtct cgaactcctg acctcaagtg atccgcctgc   5700
cttggcctcc caaagtgctg ggattacagg cgtgagctac tgcccctggc caattttgt    5760 attttagta gagatggggt ttcaccatgt tggccaggct ggtctcgaac tcctcctgac    5820
ctcaagtgat tcgccagcct cggcctccca agtgccagg attacaggca ggaatgagcc    5880
actgccccca accatcagtc taattcttat ttttgctttt tacctttttca tttttatgta  5940 gtagaggtga ttgtgtatgt tatttgtag ttagcttttt tccctgaac gttgtattgt     6000 aaatgtaaat tttttttttt tttttgaga cagagtctcg gtgtttgccc agtctgaagt    6060
```

```
gcagtggtac gatctcagct cactgcagcc tctgactcct gggttcaagc gattctccca    6120
cctcagcctc ttgagtagct ggggctacag gaatgttcca ccacgcttgg ctaattttg     6180
tattttggt  agagacaagg tttcaccatg ttggccagtt tggtctcgta ctaccgacct    6240
caggtgatgc gcccgcctcg gcctcccaaa gtgctgggat tgcaggcgtg agccactgcg    6300
cccggctgta aggttttac  ttaaccattc tattgttggg aattgggttt ccactttttt    6360
gttatagata gtggtgcagt gaacattttt aaatagcttt ttgcttcagt gtaattattt    6420
ccttagagaa agttaccaag agtggtttta ctagttcaga gggcttcagg attttttatgg   6480
ctcttgctag cggtgctcta ttattcttta gaagacttgt attacttcca gtgtcaagaa    6540
ggttgctctt ccatggaatg gtttctttgt agtttgtcaa atattgtggg gaattttttaa   6600
aggaaaaatt gcattttac  tgtcaagtgc atatattatt aagtgctttt gttagttact    6660
ggattattga tatttgagtt taatttggtt cctctgagga tttaataagg taatatatgt    6720
gaagatgttt tgaaacctgt aaccattatt attaatgagg gtacttggtt tatctgtcgt    6780
gctgatagta ctgagtaaag tgcaggaatg aaattcctga ggaactgttc taaagctttg    6840
ttgttgttgt taacctttct ttttcatctg aaagtgtttt ttattagctg ctagcctatg    6900
accaagttat ttttggtaac ttttttgtaa tttcatggca ctattgggaa ttttcgctgg    6960
ttgactcttc ttcttctaca ttcccttccc cattaaaaat aaaaatatgg atttacaatt    7020
gttactctat tcctaaacct aaataatatg acattagaat tgcttgggat acaggattca    7080
gtctgaataa aatattttc  ttttagtgat tttcagctta gtattttac  tgcttctttc    7140
tcttgaggca ttgcaactta aaaattgtgc tgtttagcca ggcgcctgta atcccagcta    7200
cttgggaggc tgaggcagga gcatcacttg agcccaggag gcggaggttg cagtcagctg    7260
agattgtgcc actgcactcc agcctgggag acagagtgag actctatctc aaaaaaaaaa    7320
aaaatgtgct gtgatttaat gtagttgttc atcatgcttc catttaaatt tcagtgagac    7380
tgttcatctt ttgcagttaa atatcttgta gaagggccta aaatatctac gttgaataca    7440
gctttattga agcatctatg tacatggggt ttttgggatg aatcagtgaa taaagcaaac    7500
atattgtcct tttggagttt acattctaat gtgactaggc agacaatgag acattaaatt    7560
accagcctat gtataatagt gtataagagc tatggaatta aagaaagca  gattaaaggt    7620
atagggagtg tggggagggg aatgagttac aattttaaat ggattggggg aacttaattg    7680
aggagctaac atttgagcaa agatttgaag gttgggtatt tagccgtttg cttttatct    7740
aggtaaatta gtcatgtggc ttcattagta atttataagg tttaaatggc atcatccttt    7800
gttattcttt tatgtgcaca ttgatactaa ccatctctga agttagacca aaaaagttaa    7860
ttgacattga gggtcattag aggtaaattg tagatggcta ttactaacca agagacatg     7920
ttttgttttt cttttgggct tacgtatttt acctaattag tttagttttt gtttcaagta    7980
tgtggagaaa ataaactttt taagtttggg ccaaaacttg ctttggtttt cttttctttt    8040
ttctttttt  tttttaaga gaaaaatgta agcctgtagt tgcttaaaga ttccacattc     8100
tgaaacagtg aaaacatggg atcagtcatg gtgttccttt ttttggttaa atgtaaactt    8160
gtattttcag tgttactcta attagcaatg gtttatactt ctacataagg gatgttaact    8220
catattgtag ctatttaata gccatatatt ttgacttaaa ggaggatctc aaggccaggc    8280
gcggtggctc atacctgtaa tcccagcact ttaggaggct gaggcgggtg gatcacctgg    8340
ggtcaggagt ttgagactag tctggccaac atggtgaaac ccccatctct actaaaaata    8400
caaaaattag ccgggcatgg tggtgggcgc ctgtaatccc agcttcttgg gaggctgagg    8460
```

-continued

```
gaagagaatt gcttgatccc ggaggttgca atgagtgcgg aggttgcagt gagctgagat   8520
catgccatta cactccagcc tgggcaacag agcgagactc tgtctcaaaa caaacaaaca   8580
aacaaaaaaa ggaggatctc atttttttgt cctaaatagc tacagccgtg ttagaactgt   8640
caccttagca aagtattgtt ttttactttt gaaacgaatt ttaaggtttt agaagattgt   8700
tctctagaat tacaattttc tgttttgact agtgatagta ttttgatgtt gtgtaaatag   8760
ttgagcatga acaaaaccct atttttttt ttagctattt caagtgattg tgacaacttc   8820
aacggagatg taaacagttt attaacagtc acacctatta tcttttttt tttttttttt   8880 ttttgagacg gagtcttgct ctgtcgccca ggctggagtg cagtggcacg atctctgctt   8940
actgcaacct ttgcctcccg ggttcaagtg attctcctgc ctcagcctcc tgagtagctg   9000
ggtctacatg cgcacaccac cacgcctggc taattttgt attttagta gagacagggt   9060 ttcaccatgt tggctagaat ggtctcaaac tcctgacctc aggtgatcca cctgcctcag   9120
cctcccaaag ttctgggatt acaggcatga gccaccgtgc ttggccgctg ccgtatcttt   9180
ttaaatgaaa gtacttgtgt ttttttgtt ttttccaaa ggatatctgg gtcatctatg   9240
atgttactgt taccatctaa gggttttttt gtttgttttt gagacagagt ctctgtcgcc   9300
caggctggag tgcagtggcg tgatcttggc tcactgcaac ctccgcctcc caggttcaag   9360
caattctcct gccttagccc tcccgaatag ctgggattac aggcacccgc caccatgcct   9420
ggctaagttt tgcattttta gtagatatgg agtttcacca tgttggccag gctgctcttg   9480
aactcctgac ctcaggtgat tcgcttgcct cggcctccca aagtgctggg attacaggcg   9540
tgagccaccc ccgcccagcc tcatgagcta aggtgttttt ttttttttg agacagtttt   9600 gctctttccc aggctggagt gcagtggtgc aatctcagct cactgcaacc tctgtttccc   9660
gggttcaagc gattctcctg cctcagcctt ctgagtagct gagattacag gtgcctgcta   9720
ccccactcag ctaattttg tattttagc agagacaggg tttcaccatg ttggttaggc   9780
tcatctcgaa ctcctgacct taagcgatcc acctgccttg gcctcccaaa gtgctgggat   9840
tataggcatg agccaccgtg cgcagcctac cctgtctctt aaaaacagt aacaacaaca   9900 acaacaacaa aaaatcctaa atcttaaaaa tggaaggcaa aaactctaag ctttgagaga   9960
ttaggggact tgcccaaagc aatatttgta ggatttatt acacctctcc ctttatttat  10020 tttttttagag tcaaggtctc cctctgtcac ccaggctgga gtgcagcctc aatctatggg  10080
gccaagcatt tctcctgtct tagcctcctg agtagctgga actacaggtg tacaccagct  10140
ggctaacatt taaattttt gtagagacag gtcctgcca tgttgcccag attggtctca  10200
aactcctggg ctcaagtgat cctcctgcct cagcttccca aagtgctgag attacaggtg  10260
tgagccactg caccgagccc cctcccttta ttttatttt taaatttaa gttctggggc  10320 ccctcccttg aaataaatag aaacgtaata tatacacaag atcatgctgt gtattttaag  10380
gcaatggtcc tcaaccttt taacactagg accggttt tgtggaagatg gttttccat  10440 aggggcaggg gatgattttg agatgaaact gttccaccgg ccgggcacgg tggctcacgc  10500
ctgtaatccc agcactttgg gaggccgagg cgggcagatc acgaggtcag gagatcgaga  10560
ccatcctggc taacatggtg aaacccccct ctactaaaaa tacaaaaaaa ttagctgggc  10620
gcggtggagg gcgcctgtag tcacagctac tccggaggcc gaggcaagag aatggcatga  10680
aacccgggag gcagagcttg cagtgagctg agatagcacc actgtacttc agcctggggg  10740
acaaagtgag actccgtcta aaaaaaaaa aattgttcca cctcagatca ttatgcattt  10800
```

```
gttagattct cataaagagc atacaaccta catctcttgc tatatgcagt tcccagtagg    10860
gtttgtgctt ctataagaac ctaatgctgc acctgatcta acaggtgggg ctcaggtgct    10920
aatgctcaca cagctcctgt tgtgcagtct ggttcctaac aggcctgttt ttttttttt     10980 aattagatgg agtctcgctc tgtcaccagg ctggagtgca gtggcacgat ctcagctcac    11040
tgcaacctct gcctcccggg ttcaagcgat tctcctgcct tagcctccca tgtagttggt    11100
actacaggcg cacactgtga tgcccagcta attttttgtat ttttagtaga cggggtttt    11160 caccatgttg gccaggatgg tgtcgatctc ctgaccttgt gatccgccca acagcctccc    11220
aaagtgctgg aattacaggc gtgagctgct gcgtccggcc ccctaacagg cttgttttat    11280
ggaatacagt cacggacagt acttgccctt caggatatct ttttgtaacc ttgattttgg    11340
cttgctaaaa taggaggtct attttctttt ctttgttttt aatgtatgtg gttctgtact    11400
tacgtggtgt gaaatctaca taaatgttaa atccttggtt atttatttat tttgagacag    11460
agtctcactc tgtcacccag tctggaaagc agtggcataa tctcggctca ctgtaacctc    11520
cacttcccag gttccagtga ttctcctgcc tcagcctcct gagtagctgg gattacaggc    11580
atgcaccact acacctggca aattttttgta tttttttttta gtagagatgg ggtttcacca    11640
tgttggccag gctcgtcttg aactcctgac cttaggtgat ctgcctgtct ggcctccca    11700 aagtttggg attacagcat gagccactgc gcctcgcctt atttttttga cacaggttct    11760
agctctgtca cccaggcggg agtgcagtgg tgccatcatg gctcattgca acctcgagtt    11820
ctcaggccca agtgatcctc ctatctcagc ctcctgagta gctgggacca caggcatgcg    11880
ccactatgcc cagcaaaatt tttgtttcac tctgttgcct agggtggggt gcagtggcag    11940
gatatcggct cagtgcaacc tctgcctctt gcgttcaaat gattctcatg cctcagcctc    12000
ccgagtagct gggattatag gcatgcgcca ctacacctgg ctaattttttg tattattggt    12060 agagatgggg ttttatcatg ttggccaggc tggtctcgaa ctcccgacct caggtgatcc    12120
atataccttg gcctcctgaa gtgctggaat acaggcata agccactgcg cctagctttt    12180
ttgtttgttt ttattttgta gggacagaga ttttacctgt tgcccaggat ggccttgaat    12240
tcctgacctc aaacaatttg ccctccttgg cctcccaagg tgctgggatt acaggtgtga    12300
gccactatgc ctggctggtt ttttaaatta ttattattgt ttgtgtgtgt gtgttgcagg    12360
atcttaccct gtcacccagg ctggaatgca gtgatgtgat ctcggcttac tgcaacctcc    12420
gcctcctagg ttcaagtgat tgtcctgcct cagcctcctg agtagctggg ataacagctg    12480
tgtgccacca tgcctggcta attttttgtat ttttagtaga gatgggggttt catcatgttg    12540 gccaggctgg tctcgaactc ctgaccttag atgatccacc cgcctcgtcc tcccaaagtg    12600
ctgggattac aggtgtgagc caccgtgacc agtttggttt agttttttttt ttttttttt     12660 ttttttttt ttttttgagaa atctcgctct gtcgcccagg ctagagtgcg gtgacacaat    12720
ctcagctcac tgcaagctcc acctcccagg ttcatgccat tctcctgcct cagcctcccg    12780
agtagctggg actacatgcg cccgccacca tgcccggcta attttttttta tgcattttaa    12840 gtagagatgg ggtttcactg tgttagccag gattgtctca atctcccgac ctcttgatct    12900
gcccgcctcg gcttcccaaa gtgctgggat tataggcatg agccaccgcg tccggcctgg    12960 tttggtatt tttttatgag tctgggttgt ttatgaaaac ttgtcacagc tgttaacctt    13020
aacttttttt ttttctttt tttccgagac ggagtctcgc tctgtcacct aggctggagt    13080
gcagtggtgc gatctcggct cattgcaacc tctgcctccc aggttaaagc gattttttctg    13140 cctcagcctc ctgagtagct gggactgcag gcacgcacca tctcgcctgg ctaattttg     13200
```

```
tattttagta gagatggggt ttcaccatat tggccaggct ggtctggaac ttctggcctc    13260
aagtgatcca cctgccttgg cctcccatgc ctggcaacct taacttttta tttgctggta    13320
attatttgtg tttgcattca tgtgaaaatt tgaaattctc attaacattt aaagattctt    13380
acatagattg cttgtaattt taaccctgaa gttgtgtcaa gtgactttac aatgtcaatt    13440
tgttttattt atttatttat ttatttattt atttattttt gtgataggat ctggctctgt    13500
tgctaaggct ggagtgcagt gttgcaaata cggctcactg caacctctgt ctcccgggtt    13560
caagccatcc tcccacctca gcctcccaag tagttggaac tactggtgcg ccccacagtg    13620
cctgcctagt tttttgtat tttcagtaga tgtggagttt tgccatgttg atcttgaact    13680
catggcctcg agtgatccac cccacttagg cctcctaaca tgctggtgtt acaggtgtga    13740
gccactgtgt ccagcccgaa aatgtcagtt tcgtgccatg attaatagct aactacattt    13800
tgggaatgta ataaaatttc attctataat gaagtctttg taaaactcat tagttgtggt    13860
atgaggcttg tcggcaatat aagtgaacgt ggtttatttt tattaactgt atcagaactt    13920
tagaatgttg gtctcctgaa accattgcct tgagaggctt tattgaacag tgttgccaat    13980
gatcagtttt tttttaaatt tcctttttt tgagactgag tcttaccctg ttggccaggt    14040
tggagtatag tggtatggtc atggctcact gcagcctcaa catcctgggc tcaagcagtc    14100
ctcctacctc agtctcccga gtagctggaa ctacaggtgt atgccaccat gcctggcttt    14160
tgtatatttt gtagagacag ggtttagcca tgttgcccag gctggtctca aactcttaaa    14220
ttcaaatgat ccacccacct agttttccca aagtgcttta attacatgtg tgaggcaccg    14280
tggctggcca ggtcaaatat ttttcattga cgttttcat attgcttttt aaagtcatgt    14340
taaaatattc ttaataattt ttctaagtgg aattaatctt gattataatt ttagttttt     14400 ataaagggcg ggttttgaaa caagtactgc attttctttt tcgggtttat aaacatttgc    14460
tgtggacttt gtgcagttaa ctattttcat tcctgaaaca catttcgaaa tcaggaattg    14520
aagactaaat gtcttttcac tgaagcttga gcagatttta gaaaggggag ttctttttt     14580 tttttttttt tttggtagaa atgggggtct tgttatgttg cccaggctgg cctccaactt    14640
ctgggcttaa actgtcctcc tgctttagcc tctggtctgg agagttcttt atggcctctt    14700
tgagaacttt tacttacac atgattctat ctagctttct tttctgatgt acatattggc     14760
agcaagtaga aaagcaatgt tttcagaggc agatatatta acagcaatga gaaataacag    14820
tagcgtgata gaaagttgaa agacttagct gggtgcggtg gctcacgctt gtaatcccag    14880
cactttggga ggccaaggag ggtggatcac ttgaggtcag gagttcgaga ccagtctggc    14940
caacatggtg aaaccctgtc tctactgaaa aacagaaaaa gggccgggcg tggtggctca    15000
cccctgtaat cccagcactt tgggaggttg aggaggcgg attacaaggt caagagattg     15060
agaccattct ggccaacagg gtgaaacccc atctctacta aaaatacaaa aaattaaat     15120 gggcgtggtg atgtgtgcct gtagtcccag ctactcggga ggctgaggca ggagaattgc    15180
ttgaacccgg gaggcagagg ttgcagtgag ccgagatcgg gccactgcac tgacgacaga    15240
gggagactcc gtctaaaaaa aaaaaaaaa aaaaaaacc agacttgggg ctgggcgggc     15300
gcctgtaatc ccagctactt gggaggctga ggcaggagaa tcgcttgaac ccgggaggtg    15360
aaggttgcag tgagctcaga ttgtgccact gtcccagc ctgggccaca gagcagagtg      15420
agactctgtc tcaaaaaaaa aaaaaaagtt tggaagactg gtggctgggc atggtggctc    15480
acacctgtaa tcccaacact tgggaggct gaagcaggca gattacctga gcccaggagt     15540
```

```
tcaagtccag cctgggcaac acagggaaac cccatctcaa caaaaaatat taatacaaaa   15600
aatttagcca gtcatggtcg tgcacttctg tagtctcagc tacttgggag gctgaggcag   15660
gtggttcact taagtctgga tgtcgaggtg agccatgatt gcaccactgc actccagcct   15720
gggcgttaaa atgagacctt atctcaaaaa aacaaagcaa agagcctggg aactactaaa   15780
atgggaacta ctaaaaaaca gacacaagag ctcaacaagt ataccattct gggaggtttt   15840
tttttttttt tttttttttt tttttgagat ggagttttgc tcttgtcacc caggctggag   15900
tgcaatggcg ccatctctgc tcactgtagt tccgcctccc aggttcaagc agttctcctg   15960
cctgactcct gagtagctgg gagtacagat attggtcaca caccgggtta attttttgtat  16020 ttttagtaga cacggggttt ccccattttg gccaggctgg tctcgaactc ctgacctcag   16080
gtgatccgcc tgcttcagcc tcccaaagtg ccgggaccac aggcgtgagc caccgcacct   16140
ggcttttttt ttttgacata gaatcttgtt ctgttgccca ggctggagtg caatggtaca   16200
atcttggccc actgcaacct ctgcctccca gcttctagcg attttcctgc ctctgactcc   16260
tgagtagctg ggattacggg tgcccgccac cacacccgga taattttttgt attttttagta  16320 gagatggggt tttgccatat tggccaggcc ggtcttgaac tcctgacctc agatgatcca   16380
cctgcctagg cctcccaaag tgccgggatt acaggcgtga ccaccactc ccggcctggg    16440 agttttgact gtaagtttat agctgtatat cttaggccct aagggcatta ctgttttata   16500
gcacagtgta gttagttaat gtgctcataa tggtgactca taacaccagg ttaaatgatt   16560
ttttatatct cccaaagaag tattttttcaa tctgcagatc atgacccctt agtagattgt   16620
gaaacacatt agtggattat gacaagcatt tttagaaaaa tgaaaagaa taagaagtgt     16680 taggatgcat tgcattattg aaataattgt ttttgagatg gagtttcgct cttagttgcc    16740
gaggctggag tgcaatggcc cgatctgcct cccgggttca agtgattctc ctacctcagc    16800
ctcctgagta gctgggatta cagacatgct ccaccatgcc tggctaattt tgtatttagt    16860
tttagtagag atggggtttc tccatgttgg tcaggctggt cttgaactcc tgacctcagg    16920
tgatccactt gcctcggcct cccaaagtgc tggggataca ggcatgaacc cctgtgcccg    16980
gcctaatttt tgtatttttta gtagagatgg ggtttcacca tgttggccag gatagtcttg   17040
atctcttgac ctcgtaatct gcccacctcg actcccaaag tgctgggatt acaggtgtga    17100
gccactgcac ccagctgcca agaattgttt taagctttgg tttgagttaa tgtatatata    17160
ccgcattgta attcaaaatg taattttttgg ccaactctgg gcacattgcc tatggactag    17220
tcctgctctg ccacgagcag caacagttca atgaattttt tttttttttt tttttttttt    17280 ttttttttttg agacagggtc tctgtcacca aggctagaat gtagtggtgc agtctcggct    17340
cactgcaacc tctgtttcct gggctcaagc gatcctccca cctcagcctc ctgagtagct    17400
gggagtacag gagcacgcta ccatgcctgg ctaattttttg tatttttgga agagatgagg    17460
ttttgccatg ttgttcaggc tagtcttgaa ctctggagct cagatgatcc acccaccttg    17520
gtgtccagaa atgctgggat tacagggatg agccaccgtg cctagccaaa aatttttttt    17580
taagtaattt tttattgata tagtcaaaaa agttactgct ttagagccag agaaacgcag    17640
taaaaggatt gagaaagagt tttgaggtta tatctaagct agggttgtca gatttggcaa    17700
atagaaatac aggacactca gttaaatttg aattttttgat gaacattgac cagttttttta   17760 gtataattgt gtattaaatt gcatagaaaa aagttattta tctaaagttg aaatttaact    17820
gagcatcttg tattttatct ggcaactcca gtctaagctg gaatcatggt tcactgtttt    17880
tttttttttt tttttttttt gagtcggagt cttgctgtgt tgcccaggct ggagtgcaat    17940
```

```
ggtgcgatct tggctcactg caacctccac ctcctgtgtt caagtgattc tcctgcctca    18000
gcctcctgaa tagttgggat tacaggcacc caccaccatg cccagctaat ttttatattt    18060
ttagtagaga cggggttttc gccatgttgt tcaggctggt cttgaactcc tgacctcagg    18120
tggtccgccc acctgggcct cccaacgtgc tgggattaca ggcatgatct accgtgcctg    18180
gccatggttc actcttcagt aactaaaatt taagctctat gaaagcagga actttgtttt    18240
gttcactatt gattgtatcc ctatttcttg aatggttggc acttaactgc ttggtcacat    18300
gtttgaatgg gcaagttact cagccactct caggcttagt ttatttacct attaaaagag    18360
aaagaatatc ttccttggct gggcgcggtg gctcacgcct ataatcccag cactttggga    18420
ggctgaggcg ggtggatcac gaggtcagga gatcgagacc aacctgggca acattgtgaa    18480
acctcatctc tactaaaata gaaaaaatta gctgggcatg gtggtgcgca tctgtagtcc    18540
cagctactcg agaggctgag gcaggggaat cgcttgaacc caggaggtgg aggttgcagt    18600
gagccaagat tgtgccactg cactccagcc tgggcgacag aacgagactc tgtctccaaa    18660
aaaaaaaaaa aaacaaacaa aaaaaaaaac tgagatactg gccgggcgcg gtggctcgtg    18720
cctgtaatcc cagcactttg gaaggccgag gcggtggat cacgaggtca ggagatcgag    18780
accgtcctgc ctaacatggg gaaaccctgt ctctactaaa aatacaaaaa attagccagg    18840
cgtggtggcg ggcgcctgta atcccagcta cttgggaggc tgaggcagga gaatggcgtg    18900
aacccgggag gcagagcttg cagtgagcgg agatggtgcc actgcactcc agcctgctgg    18960
gcgacagagc gagactccgt ctcaaacaaa caaacaaaca aacaaaaaaa ctgagatact    19020
aaagtcttaa tattttctgt ttttatgtat ttatttttg agatgggatc ttgctgtatt    19080
gcccaggttg gagtacagta ttgtgatcat ggcttattgc agcctttaac tcctgggttc    19140
aagtgatcct cccacctcag cctcctgagt agctgggacc acaggcacat gcaacatcac    19200
accctgcagt tctttttttt tttttgagac accgtctcgc tttgtcaccc aggctgcagt    19260
gcgtggtgca atttctgctc actctaacct ccacctcccg agttcaagca gttctgcctc    19320
agcctcctga gtagcttggg accacatgtg tgtgccatca tgcctggtta attttttgta    19380
tttttagtag tgacagggtc ttaccatgtt gcccaggttg gtctcaaact cctgagctca    19440
agtgatctgc ccgccttcgc ctcccaaagt gtctgcgccc tacaatttaa aaaattttt    19500
gtagagacag tctcactgtt acccgggctg gttttgaact tctgccctca agtactcctc    19560
ttgccttggc ctcccaaagt attgaaatta aggccatgag gcagcacacc cagcctaaat    19620
tcttcttatg ttctgttctt ggcacatagt agatgttcaa caatgtagag tcaaacgcat    19680
ttggagttgg aatggctctg gtgttttttt tttttttta aaccagaaac acgtgcagtt    19740
tattgaatgc cattgtagaa aagtgtgtga ggataaacgg ctgatagaga acttggctct    19800
gggggcaggg cgaggaatgg agggtggatg gagtacatgg gaatcagatc acgggcagag    19860
ctcctggcct agataatgcc tcctgatctg ttgatagact tgaaagatca cactgggat    19920
gatgctgagc agaatggtcg taatgatgcg cacaatcagg gcccagatgt tcaggcactt    19980
ggcggtaaag gcataggcct gggccctgat caggtcgcca accatcttct tgtccctaga    20040
cttcacggag taggccaatg ctatgaagcc caggcagcag gagttcatga agtgggtgtt    20100
gaacagggac cagacgacat ggtcgggcac ggagttctcg ctgtggatgg ggatcacggt    20160
ggacattggg ggagcagggt tgtgggtgc cccagcaca gccacctctt gctcctcctt    20220
gagcatctca tagttagggg gatggccgat gttggcagga gtgaagaggt ttggacattg    20280
```

```
tggttcatgg tgtccaggga agaccagctg tggtcgggtt gctggggtgg ttctcagtgg      20340
gcccctccct ttccctggta gtttggattt ctctggctct ggtggttttt tagtactcat      20400
tctatttacg ggtgaagaaa ttgagaccaa gagggttatt taccagagta tctcatcatt      20460
ggctgcataa ctggcattag aatctgatgt acttttattt ctaatacatt tcttttttt      20520 tttttttttt tgagatggag tctcgctctg ttgccgagcc tagagtgcag tggggcaatc      20580
ttggctcctt gcaacctcca cctcctgggt tcaagctatt cctgtctcag cctcccaagt      20640
agctgggact acaggcacct gccaccacag ccggctaggt tttgtatttt agtagagatg      20700
gggtagcacc atgttggcca ggctggtctc gaactcatga cctcaggtga tccacctgcc      20760
tcggcctccc agtgctggga ttataggcat gagccaccat gcctggcctt tctttgtcgt      20820
ttcctttctt tctcttcatc cctcctctcc tttttccc tccccgctgc ctcctcctgt      20880
cttcccttct ttccttcctt tctctccttt ttattttttc ctttcttttt ctttctctgt      20940
ctctcccaac ccttcctctc tccctcccte cctccccttc tctctccccc cctccctccc      21000
cttctctctc cccctccct ttgttccta agagacaggg tctccttatg ttgctgaggc      21060
tgaccttgaa ctcctgagcc cagatgattc tgcctcctta gtagctggga ctacacccac      21120
ctcccgttcc gttgtcatct tttttttttt ttctttttt ggagacagaa tcttcctctg      21180
ttgctcaggg tggagtgtag tggcacgatc atagcttact gtaactgtgt aacctcgaat      21240
tcttgggctc aagcaatcat cccatcatcc cacctcagct tgctgagtac ctggggctac      21300
aggtgtgtac caccatgtcc ggctaattac ttttcttatt tttaattttt cggagatagg      21360
atcttgctct gttgcccagg ctggtgtcaa actcctgggc tcaagtgaaa ctcttgcctt      21420
ggcctcccaa agtgttggga gggattacag gcatgagcca ctgcacccag cctcctcttt      21480
cttcccattt aactcctaac cacaccgaac tttctgtctg cagagaggag cattggtcag      21540
cagttcacaa aatggctagg tgtgatggcg tgcacccata gtcccagcta cttggggagc      21600
tgaggtggga ggatcgctgg agcccaggag ttcaaggccc tgggcaacac agcaagacct      21660
tatctctggc tgggcccagt ggctcacgcc tgtaatccca gcactttggg aggctgaggt      21720
gggtggatca cctgaggtca ggagttcgag accagcctgg ccaacatggt gagaccctgt      21780
gtctactaaa agtacaaaaa ttagccaggc acggtggcgc gctcctgtaa tcccagctac      21840 tcggggggc tgagacagga gaatcacttg aacccaggag gaggaggttg cagtgaacca      21900
agaacacgcc actgcactcc agcctgggtg acatagtgag actcttatct caaaaaaaaa      21960 aaaaaaggt cgtctgtact attgcatgtt agtagtttct ttctgcttat tgttgagtag      22020
tagtctattg tatgcatgta ccagtttgtt catctagtgg tggacattga gttagcaggt      22080
tttggctatt aaaataaag ctggaggccg ggtgcgatgt ctcacgcctg taatcccagc      22140
attttggaag gccgaggcag gcggatcacc taaggttggg agtttgagac cagcctgacc      22200
aacatggaga acccccatct ctactaaaaa tacaaaatta gccaggcgtg gtggcgcatg      22260
cctgtaatcc tagctactca ggaggctgag gcaggagaat cgcttgaacc cgggaggcag      22320
aggttgtggt gagccaagat tgcaccattg cactccagcc tgggcatcaa gagtgaaact      22380
ccgtctcaaa aaaataaata aataaagctg gtatgaatat ttatgtacag gttttgtgtg      22440
aacatatgat tttatttctc ttggttggaa tgcatagaaa tgagattgct gggttttgtg      22500
gcaagtgttt attttttccag ggtacatata atcctgtgag tgtttattta atttaaaag      22560 taattgctaa actgtttgct aaagtgactg ctatattttc tttccctagc agtgtatgaa      22620
tttttttttg aggcagggtc ttgctctgtc acccagggtg gagtgcagtg gtgcgatatt      22680
```

```
gtctgactgc aacattgacc tcctgggctc aagtgatcct cctgcctcag cctcctggct    22740
gggaccacag gcatgtacca ccacacctgg tagtttgctt tgattttag tagagaagag    22800 gtctcactat gttgccctgg gtggtgttga actcctgggc tcaagtgatt catctacctc    22860
agcctcccaa agtgctggga ttatagatat gagcccctgt gcctggcctc attgtggttt    22920
taatttgcat ttccctaatg cccagtgata ttgagcattt tttcatgtgt ttatttgaca    22980
ttcataccat ctttggtgat gagaaactat gtttatgcat tgcttaatga tggggatgtg    23040
ttttgagaaa ttttttcggt gatcttatca ttgtacaaat atagagttta cttacacaag    23100
cctagatggt atacctacta gacacatagg ctgtcgtaca gagtattact cttaggctac    23160
aaatctgtat agcatgttgc ggtactgaac actgttggca gatgtaacat aatgttaagt    23220
atttgtgaat ctaaacatat ctaaacatag aaaaggtgag taaaaataca gcgtaaaaga    23280
taaaagtggt atatctgaat aggtcactta ccatgaatgg agcttgcagg acaggaagtt    23340
gcttgggatg agtcatttat cagtggtgtg tgaatgtgca ggcctaggac attactgtat    23400
gctactgtag acaaacactg aacagttagg atacactaaa ttgataaata tctttcttat    23460
tttgtttttt gagatggagt ctcgctctat cgcccaggct ggagtgtagt ggcgtgatgt    23520
tggctcactg cagtctctgc cttctgggtt caagcgattc tcctgcctca acctcctgaa    23580
tagctgggat tacaggtgcg tgccaccaca cctggctaat ttttgtattt ttagtagaga    23640
cgggggtttc accatgttgg ccaggctggt ctcgaactcc tgacctcagg tgatccaccc    23700
gccgtggcct cccaaagtgc tgggattaca gatgtgagcc accgcacctg gccagagatg    23760
aggtcttgct gtattgccca gggcgttgaa ctcctgggct ccagcaatcc tcccacctca    23820
gcttcccacg tagctgggac tgtgggtgca cgccatcatg cctagccgtt ttgtgaactg    23880
ttgaccaatg ctcttttctg cagacagaaa gttcactgtg gttaggagtt aagactttta    23940
acctctgacc tcaagtgatc tgcccacctt gacctcccaa agtgctggga ttacaggtgt    24000
gagccatcac gcctggtcaa aaatatcttt ctttaagagt aaatttacct taacttactg    24060
gttgatcatt gtatataggt ctgttgttaa ttgaaacatg cgggccgggc ccggtggctc    24120
atgcctgtaa tcccagcact tgggaggcc gaggcgggtg gatcacaagg tcaggagatc    24180
gagaccatcc tggctaacac ggtgaaaccc cgtctctact aaaaatacta aaaattaacc    24240
gggtgtggtg gcgggcgcct gtaatcccag ctactcggga ggctgaggca ggagaatggc    24300
gtgaacccgg gaggcggagc ttgcagtgag ccgagatcgt gccactgcac tccagcctgg    24360
gcaacagagc gagactctgt ctcaaaataa ataaataaat aaataaataa ttgaaacatg    24420
cggtgcatgt gtttatttgc gatctgactt gtttggaaat atttgcatta tcttccttct    24480
agatttagag catcttgaca gtaggaacaa gtgttttgta caactttgta tgcttagtaa    24540
gttatcaatt aacttgtcgt ggccaggcgc agtggctcac gactgtaatc ccagcacttt    24600
gggaggccga ggcgggcaga tcacctgagg tcaggagttc gagaccagcg tggccaacgt    24660
ggtgaaaccc tgggtttgtt tgtttgttta tttatttatt tattttttgg agacggagtc    24720
tcgctctgtc gcccaggctg gagtgcagtg gcgtgatctc ggctcactgc aacctccgac    24780
tcccaggttc atgccattct cctgcctcag cctcccaagt agctgggact acaggagccc    24840
gccaccatgc ctggctaatt ttttattt tagtagagat ggggtttcgc cgtgttatct    24900
gggatggtct cgaactcctg actttgtgat ccgcccgcct cggcctccca agttctgggg    24960
attacaggcg tgagccacca cacctggcct accctgtgtt tattacaaat acacaaattg    25020
```

```
gccatttgtg cgtggctcat ctacagtctc agtgactcag aaggctgagg caggagaatc    25080
tcttgaaccc gggaggcaga ggttgcagtg agcagagatc gtgccactgt acttcagcct    25140
gggtgacaga gtgagactgt gtctcaaaat aataataata atttgttgaa tatgtgactg    25200
ttggtttaat ttttattttt atgagatgga gtctcactct gttgcccagg ttggagtaca    25260
gtggcgtgca gtggcgcaat cttagctcac tgcaacctcc gcctcctgtg ttcaggtgat    25320
tcagcctccc aagtacctga gactacagac gtgcactacc gtgcctgact aattttgta    25380 tttttagtag aaatggggtt tcaccatgtt ggtcagcctg gtctcaaact cctattctca    25440
agtgatccgc ctacctcgac cttccaaagt ggcggaatta taggtgtgag ccgtggtgcc    25500
cggccagact attggtttgg tttggtgtga tgttatgtta tgttatgtta tgttatgtta    25560
tgttatgtta tgttatgtta ttttaagaca gagtttgtct cttgtcgccc aggctggagt    25620
gcagcggcat gatctcggct tactgcaacc tccgcctccc aggttcaagt gattctcctg    25680
tcttagcctc ccaagtagct gggattacag gcgcccacca ccgtgcctgg ctaattttg    25740 tatttttagt agagacaggg tttcaccatc ttggccaggc tgttctggaa ctcctgacct    25800
catgatccac ccgccttggc ctcccaaagt gctgggatta caggcgtgag ccactgcgcc    25860
tggctgacta ttggttttat tattaagcag tagtagttga ccctgtcatg tagaaagcat    25920
ggcatttata ggcataccac gtttaatttc ctccctttt tttattttg gagtacctcc    25980 tgcttgtgag gcttgggaat acagtagtga ataagccaga tgaggtctct ctcttttgg    26040 agcttatgtg gtagtataga ctaggcagaa agttctcatt gcccctgcca ccttatggca    26100
ttgaggtgtt tgagatgctg atgtttactt ctgtctcata aaatcttgaa aggagttctt    26160
ttagatgaag aggaaaacaa atcagaaga atgggcctgg gtcatgtctg taaacctccc    26220
cacgtcatgg ggaggctgaa atgggaaggg ccaggagttc aagaccaggc tgagaaacat    26280
aacaagaccc catctctaca aaaaatattt tttaattaat gggggatggc agcacacacc    26340
tgtagtcgca gctactacga ggctgaagcg agaggattgc ttgagctcag gagttaaaga    26400
ttgcaggagc tatgatcaca gcactgcgct ccagccctc ttatcagcag tctggtatgt    26460
tgctaagggt cttgttcttt ttagtgcttc agggacagcc actggctatg cccagaaata    26520
agtatgtttg agaagctttc tgacctcagc ttgaaaaatt gattagggtc ataattaaaa    26580
agggagggaa acaggattga gtgaaccgga cgctaccgtg agtttattct cccagggcat    26640
acataatctc atgtgattac cacatagccc tgttagataa tctgttatcc tgtcctcatt    26700
ttacccatga ggaaatgaag gcccagagag gttaaatgac ctattcaaat tcactcagaa    26760
ggtggcagag atgagttact atcattgtat tttggatctc tggaaagaaa gaaaactagt    26820
gatggtatta aaaaatgtta ttaatagttt cttttaatca accaggaact tgagtcacta    26880
gcttctctgg gtgaaggact atacttcaac agtatgaaaa acggaaaaga aaatgaggaa    26940
ttttggctgg gcacagtggc tcacacctgt aattctagca ctttgggaag ccaagggagg    27000
agggtcgctt gagctcagga attcaagatc agcctaggca acatagtgag gccccatctc    27060
tacaaaaata aattagctgg gcatggtggt gcatgcgtat agtctcagct acttgggagg    27120
ctgactcagg agggtcactt aaacccagga attggaggtt gcagtgagct atgattgcgc    27180
cactgtatac catcccaggc gacagagtga gaccctatcc cccaccgcc aaaaaaaga    27240 aaagaaaatg aggaatttac atttgtgaca gatacggaat tcaggaatt tagttgttca    27300 tagtctataa atgctataag aagtctccat acctttttt tttttttt tttttttgg    27360 agacagagtc ttgctctgtc gcccaggctg gagtgcagtg gtgcgatctt ggctcactac    27420
```

```
aagctctgcc tctcgggttc acgccattct cctgcctcca cctcccgagt agctgggact   27480
acaggtgccc gccaccacgc ccggctaatt tttttgtatt tttggtagag atgaggtttc   27540
actgtgttag ccacagatcc cgacctcatg atctgtctgc ctcagcctcc caaagtgctg   27600
ggattgcagg cttgaatcac cgcacccggc cggaagtctc catactttt aacccaatct   27660
aaaatggtaa ggaaatatat aagaatgtct atttattatt aaattttttc tatataaaac   27720
atttcagaaa ataagactag cattctga gccaagtggt agtagtggcc atttttctg   27780
gaaaaaaaa aaaaagaaa gaaaaaacac atttagctat ctatgatgtg aaagatgaa   27840
catttattt aggtaataaa tgttatgtca taaaatacca tttattgtgt gcctattagg   27900
tttcaggaga gctgtgccaa gagcattact tgtatatctt ttaagcctta caacagccca   27960
gcctgtcagg ctggtagtgc catatctgtt ttacagatga ggaagtgatg gattggagaa   28020
attaaggaaa ttgcctttag gtcaaagaga taggaagtga caaagctgag attttaacc   28080
ttgtgagatt tcaaagtctt tgcttttaa taactgttcc attgcttcta atatagagat   28140
atgacaaaaa caagtaaaaa tcagtgaaga aggctgggag cagtcgctta tgcctgtaat   28200
cccagcagtt tgggaggccg aggcgtgtgg atcgcctgag gtcaggaatt tgagaccagc   28260
ctggccaaca tgacaaaact ccgtctctac taaaaataca aaaagttag ccaggcgtgg   28320
tgacaagcac ctgtaatccc agctactcag taggctgagg caaggagaat cgcttgaacc   28380
tgggaggtgg aggttgcagt gagctgagat cgctccattg cactccagcg taggcaacaa   28440
agcaagactc cgtctcaaaa aataaataaa taaataaata aaaataataa caataatgaa   28500
gaaaacaatc cggtgattat tgtcagcaat aaaatttctt caatcaacca tgctttagtc   28560
ctggcagttc tctatcagtg agtttcaatc aaaaagtttg tttataattt ttttttttt   28620
aaaattttga aatttggaaa caacatcata aatgatggtt agttttctgc agctccctat   28680
tttggcagat agtctgttgt tactcataat taatttgaac taaaaagtag tgttgtacga   28740
tatcatgggc tgtgaatgtg tttgtgactt gatctgagaa cccacacacc acttaggatg   28800
cttctgtagg aaaattagag tatgaactc acttgcccac gctttccctg tctcagtcca   28860
tgttggtagg ctgcaaagtc tggggctaga aggacactga acaagacttc agcagtacat   28920
gttagtcttc cagagggaag gaatataata gttgagagaa taattccttt cctctgtgac   28980
tttaggcaaa ttcttggcta tgctgttatt tatttgggcc aaacaatatc aggaggttgt   29040
acatttattt cttaattact gcgatacatt aattttatcc atgggtttaa cctagcctac   29100
cttttgctgt tagacttcaa ctctacttgt gttgggttac ccctctgctt aaaaatcacc   29160
ctattcccaa gcctgaggga gtctaccttc aaagctttct atgacctaat ccaaggcctg   29220
tcaaacttcg taagggcca gatagtaaat ttgttttttt tttttgagat ggagttttgc   29280
tcttgtcacc caggctggag tgcaatggtg ccatcttggc tcactgcaac ctctgcctcc   29340
caggttcaag tgattctcct gcctcagcct ctcaagtagc tggggttata ggcatgtgcc   29400
accacgctcg gctaatttct ttgtatttag tagagatggg ggtttcacca ttttggtcag   29460
gctggtctcg aactcctgac ctcaggtgat ccacctgctg cggcctccca aagtgctggg   29520
attaccagtg tgaaccaccg tgcccagccc gatagtaaat attttaggct ttgcagtcca   29580
tatacagtcc cattttttg tgtatgtttg cacgttttct ttacatattt taaaagcccc   29640
tttttttttt tttttgagac agagtcttgc tgtgttgctc aggctggagt gcagtggtgc   29700
aatcttggct cactgcaacc tctgcctcct gggttcaggc gattctcctg tctcagcttc   29760
```

```
ccgagtaact gggattacag gcacatgctg ccacgcccag ctaattttg tattttagt    29820
aaagatgggg tttcgccaca ttggccaggc tggtctcctg atctcaggtg atctgcccac  29880
ctctgcctcc caaagtgctg ggattacagg tgtgagccac cgtgcctgac ctaaaagctc  29940
tttacagtgt aaaaaatatt ctgagcttta agccatgtga aataggcca tgggcatttg    30000
ctgaccccta atagaactcc attttacctt tctgatcatg tttcccatta actcttcaaa  30060
aatatgacct ccatttaaat caagatggtc tccttcctca ctgcttgtgg aggtccagtg  30120
cccagtgtct gcctcttgct tgctcctcca tcattgttct gccattcgag atcctcatac  30180
ttacccttta agatctagcc caaattttcc atgaaactaa ttctaataat taaaaacttc  30240
ctgtagaact taactttgtc tagtacaagt tagctttctt attcagtagt agcttactat  30300
aaattacaag aataaaaaga ttaccatttt ccctcacact gttttgtgga gaatgcctaa  30360
agttacttt tctttttaca ggtcagtatt cctatttggc atcctaatcc cctttcccaa    30420
atctgaattt tgggatttga agcttgcatt tgagattatg atttgtcttc cttgttgtac  30480
acaggagcag ggactttaca attagtattc gcatccctgc tccttcatac ttcgtgatgt  30540
aaggcaagtt attttcactt atgcttaagt ttcttcccct gtaaaaaggg gatggaagag  30600
gattaaatga attaaacatg taacacgctt aaagcaatgc ctggcaagta ataagtgctc  30660
agtaactttt agctgttctt attagcatgt ttggaaacca gtagaaacta caccagcaag  30720
ttaaggttga aaagtggtat tgatgggctt ggggtagtac agtatgaatg ctacagtttt   30780
agcgtttcat taagtttgta tattcattaa ttcattacac atttgatgct gtcagactag   30840
gacagagaca aagatgaatg aaacattatc tctgcttcca ggttacccag tgtagtagag   30900
aaggcaggca tgcagatagt ttaaattggt agcactggga ggggactgcc atgggtgggc  30960
agtgaagaaa aagggcttca aaataatgag agttgagatg gatcttcaag gaagataagc  31020
agttttcagt aaggccatga agagaggagg aagttccagg cgggaagagt ttgtgctaaa   31080
gtacagggat tgctatacac atggtgtatg tagaaaaaat ttggttcaca gtgtgataga   31140
agaattggag ggggtcctca ctgaaagtaa ggaaacacat ttggaagaat atgtttcagt   31200
tagaaaatga aatgagctta aagtaaacgc taataaggtt tttaaaatgt aaaatttcaa   31260
cgtatttaga aagagaacag ctggatgaat cttatgtacc tgtcactcag ctttagcagt   31320
tatcagtaaa tggccaacgt tgtttcagct atactcccct ctcctccact gatagtcttt    31380
tgaaggggaa tacaattgtt ttgtggcctc cagaaaggga taagtttatg agcaacgggt  31440
agatcgttgg gagagacttg agtttcctgt caggaagcat tcttggtgca taagtcagag   31500
gtgatatgaa tgccgtggaa gggggtggct tactgtctgg agaactcgag aagatgggaa   31560
tgggcactgt ccagtattgt ggctacttcc acacatggtt cttttaaattt aaaattatgt 31620
tgattaaaat ttaaatattt cagttcctca gccatactaa tcgtatttca agtgcttagc  31680
tgccacatgt gcctaatggc tgcaatattg gacagcatga cataggacat cttcatcatt   31740
gtacaaagtt ctcttggaca gcatgggact agagccctaa gatccttttc tacctgagtt  31800
gtttggattt tttggtgtgt ctaggttgga tctagttgtt catggcttca tgaccaagcc  31860
ttttatccct ttctctagag ggactcaagg ggtaaaggca ctgaaggggt aaaacttcat  31920
atgaagagtg tggtggtggt ggtggtgttt taagacaggg tctcgctctg tcactcaggc   31980
tggagtccag tggcatgatc ctggctcact gcagcctcga cttcctgggc ttaagtgatc   32040
ctcccacctc agctcccaag taactggaac tgtaggcatg agccaccaca cctgcctaat   32100
ttttaaaact ttctgtagag acgagatttc gccatgttgt ccaggctggt ctcaaattcc  32160
```

```
tggactcacc ttggcctccc agagtgctgg gattgcaggt gtgggccact gcgactggcc    32220 tttttttct  cctttactac tctagtgtat gctggaatat gaggaaataa ttatattagc    32280
tagcagttat taaacactta ataacatacc aggcactgtt ttaagctatg cgatctgtat    32340
ggaatattac ttaatttcca caaccttatg aaaagatact attttttttc ttttgagaag    32400
gtactatttt catcttcatt tcatagatgt tgaaattgaa acacagagag ctgaagtcac    32460
aggattaagg ccacagagct gagaagtgat ggagccggaa tttgaaccca agcaattaat    32520
gctgatatta gttcttgtgt gaatggtaat tgttttgaaa caatgatcct agatgattat    32580
atgaccggat taatctggca gttgttctgt gtgaatttag agttgccttc ccacctcagt    32640
ttcctaaaaa caaacaaaa  caaaacaaaa caaaaaaaac tctagcttca ctgtgtttgg    32700
gttgtcatgg cctacccct  cttgccacct catttgactc aacttttttag ggagaaaata   32760 ttcaatacgt ggtataggat ttcccttttct aataataatg taaacaacaa caagaagtct   32820
gaaattggaa gaacaaaatg actcacctaa gtgagttaac cttaagaggt ggaacttgat    32880
ttctagattt tagttaattg tctaactgat gtactaaata ttagttactt aagtattaaa    32940
acgggtagac ataatagttg gggagctgct gtagaggggg tagtttgaga aggcttcttt    33000
caggaggtga catttaagtt ggtaactaac aagaaagggg cagccatgtg aatagctgga    33060
gggaagagca ttcttacagt tttactggaa ggggttaga  ggtatgtggt accttatgc     33120 caaagaaaat tagttacttc tatacaacca gtctgattct agaaacctgg atcaatgaaa    33180
tattttgatt atataaaaaa atctgttacc caggtcttgt tgaaatagca ttagaaacta    33240
ctgaaggaca tatagaggag gagtgttgaa aaatggtgat ggatgagcag aatggtgaaa    33300
aataaaaaga catgaagctc tataattata ttgtatggtg acagtaccaa tagagattgc    33360 atgtttttc  tccccagttt tttttttgt  tttgttttt  gttttgaga cagagtctca     33420 ctgtgtcact caggctggag tgcattgtcg tgatattggc ttactgcaac ctctgcttcc    33480
tgggttcaag cgattctcct gcctcagcct cctgagtagc tgggattaca ggcatgtgcc    33540
accacgcccg gctaattttt gtattttat  ttgagagggg atttcaccat gttggcaagg    33600
ctggtcttga gttcctgacc tcagataatc cacctgcctc agcctcccaa agtgccggga    33660
ttacaggtgt gagccactgc gcccggcctc ccccagttgt tgaaacaata atggaaggta    33720
attttattct tagattattt aatgttttc  agttatcagg atgtgttaga ttgtttgtgt    33780
atattgtttt gcttgttaat taagtaacac agtgaataag acagacaaac atacgaaaat    33840
gtacatttat tttattttt  tgagacagtc tgttgcccag gctggagtgc agtggcccaa    33900
tctcggccca ctgcaacctc tgcctcctga gttgaagcga ttctcttgtg tcagcctcat    33960
gagtagctgg ggccatgggt gcacgccacc atacccggct aattttttata ttttttagtag  34020 agatggggtt tcaccatatt ggccaggctg gtctcgaatt cctgacctca ggtgatctgc    34080
ccgccttggt ctcccaaagt gctgggacta caggcatgag ccactgtgcc aggccatttc    34140 attttttggaa cgttcttttt tttttttgaa atggggtctc gctctgtctc ccaggctgga   34200
gtgcagtggc tcaatctcag cttactgcaa cctctgcctt ccgggttcaa gtgattctcc    34260
tgcctcagcc tcctgagtat ctgggactac aggtgcatgc caccacgcca ggctaatttt    34320
tgtattttta gtagagacgg ggtttcacca tattggtgag gctggtcttg aactcctggc    34380
ttcgtgatct gcccgcctca acttcgcaaa gtgctgggat tacaagtgtg agccaccacg    34440
cccggcctgt ttctggaata ttcataatct tttgttgtca tttcaacagt gctcacagca    34500
```

```
gcttcaccag gtgtagattc catcttaaga aaccactttc tttgcttatc catgagaagc   34560
aacacctcat ctattcaagt tttatcatga gattgcagca attcagttac atcttctgac   34620
cccacttcta attttagttc tcttgctttt ttaccacatc tgcagttact tgctctactg   34680
aagtcctgaa cccctcaaaa tcattcatga gtattagaag caatttcctg gttgggcacg   34740
gtggctcatg cctgtaatcc cagtactttg ggaggccaag gagggcggat cacctgaagt   34800
caggagttca agaccagtct ggcaaacgtg gtgaaacccc gtttctacta aaaatacaaa   34860
aattagccgg gatgtggtgg cgggcgccta atcccagc tacttgggag actgaggcag   34920
gagaatcgct tgaacctggg aggtggaggt tgcagtgagt tgagattgtg cccttgcact   34980
ccagcctggg caacaggagc gaaactctat cttaaaaaaa aaaaaaaga aaagcaattt   35040
cctctaaaac tcctgttaat gttgatgttt taacctcctc ccatgctcat ggatggcatt   35100
ctcagtggca tctagaatgg tgaatacttt ttagaaagtt ttcaatttat tttgccatca   35160
gagaatggct atgaatgcca gtagtagcct tacagaatgt atttctttt tttttttct    35220
tttttttga gatggagttt tttttgctct tgtcacccag gctggagtgc agtggcatgc   35280
tatctcggct caccgcaacc tccgcctccc gggttcaagc aattctcctg cctcagcctc   35340
ctgagtagct gggattacag gcatgcacca ccatgcccac ctaattttgt attttagta    35400
gaggcggggt ttctccatgt tggtcaggct ggtcttgaac tcccgatctc aggtgatctg   35460
cctgcctcgg ccttccgaag tgttgagatt acaggcgtga gccaccgcgc ccggccgtat   35520
ttcttaaata aaatggctta aacgtcaaaa ttatcccttg atccctgggc tatggactga   35580
ttcttgtgtt agcagttatg aaaacattta tgtccttgta cattcccatc atagcttttt   35640
gtcaatgaga agtaatttt tttttttttt tgagacagaa tctcactctg tttcccagcg   35700
tggagtgcag tggcatgatc tcagctcagt gcatcctaca actctgaggt tcaagcaatt   35760
ctcgtgcctc agcttactga gtagctggga ttacaggcgc ccaccaccac gtctggctaa   35820
tttttgtatt tttagtagag atggggtttc acgatgttgg ccaggctggg ctcgaactcc   35880
tggcttcaag tgatccacct gccttggcct cccaaagtgc tgggattgta ggtgtgagcc   35940
actatgcctg gcctaattgg cctaatttca atattgttat atctcaggga atagagaggc   36000
acgaggagaa agagagacaa gctgactgct ggttcgtgga gtagtcataa cacacaacat   36060
ttattaagat tgctgtctta tatggaccgt ttgtggtgcc ttaaaagaaa tcagggtaac   36120
atcaacgatt actgattaca gattactata acagatacaa taataattgt aaattattat   36180
ttacaattgt aaaatacaat cttttcttta ttatttacaa ttattgtaaa atacaatctg   36240
attacagatt actataacgt atacaataat agtggaaaag tttgaaaata ttgtgagatt   36300
tatgagaatg tgacacaggc gcaaagagag cacatgttac tggaaatacg gcactaatgg   36360
acttgcccga ctcggggttt ccacagacgg tcagcttgtc aaaaatgcag catctgtgaa   36420
tttcaataaa gcaaagcaga ataaaatgag gtatgcatgt attgccatca catgtacact   36480
agtaaaatac gttttttttt tcagtaggtg gatcaacctc aaatttaat ataaagcatt    36540
acttaaagga gaatatgggg acattcatga catttcttat atgtacataa aacttcatga   36600
aaataattta atgctatcca gcagtttatt ttagaagtac tggaggctag catggtgtc    36660
ttatgcctgt aatcccagca ctttgggagg ctgaggtagg aggatcactt gagttcagga   36720
gctggagacc agcttgggca atatagtgcg acccccatctc tacaaaagag aaaagaagta   36780
ctggagtgtt gcagctctta cagaatttgt ctagcaggtt ttccagtctt taccagaaat   36840
gccccccatgc agaagtagta aatactgatt catgtaaaat aataaacaac tttatctttc   36900
```

```
agtttttaaa agacagggtc ttgtaacgtt gcccagactg gcctttaatt cctgggctca   36960
agcgatcctc tcacctgagc cttttgagta gctgagacta caggctgcac ctctgcacct   37020
ggctctgctt gattttaat  tgttgtattg ctgttgcagc tatgttttt  ttttctcttca  37080 gtgtgaggat gggcaaactt tttatgtaaa gtctcaggta ataagtattt taggctctag   37140
ggccatatag cttctctgtt gcatatcctt ttttttttt  tccatttccc ctcaaattcc   37200
ttttaccata agcaactctt gaggaacata aaaatcattc ttagcccaga agccagacca   37260
aaacaggttg tgggctgtag tgtcctgacc cctgatttaa agattgatag ctttgaaatg   37320
gaaagtttta actttctttt tttttcttc  ccttgttctg attgggctgt taattcatta   37380
ggtatttact cagtgtgtat catatgaggc atgattcctc tgctaatttt ggtagtggta   37440
gaaagatact tttgccaagc ttggttgtta ggttttcatt tgtccaagag ttcctgacca   37500
agtgtgaatg gatgttgaaa tcaaggtgtt tctttggcca cacaatgtgc ctttgggggc   37560
tatatctatg tgcttctggt accttctttt aattttcaca aagacactgc ttgccgacca   37620
cactgttttg tctaatgtgg ggctatgacc ccctggaaga ggcatcattt tctgattttc   37680
acagaagcat aatatggtca ggtgatggtc ctgagtagtg ggtatatgac agatacacta   37740
gtaattataa tacagatcta aactggagag ttgaaaacag catcgtatat ttgattgaga   37800
taatcgaagg aagacttcct gaaaagatgg catttgagtt tcaaggctga gtaggattaa   37860
gtattattat ttaaaaaatg ccttggacaa tgcattaaat agagttaaca aatcacatca   37920
cttatagtct ccaattaaaa acattttact taaacataat tttagacttt tagaaaaatt   37980
gcaaagatat tataaagaat tctcctatat atctcacctg tattcttcaa gtaacatttt   38040
accatattca ccttaacatt ttctctgtat tggtaattgt atatgtaaga tttaatataa   38100
aataaaaatt cttattaaac atatgagaga catgatgcct ctttagccct aaatacttca   38160
acttgtatgt actaataaca agggcattct atttcaaaac cacagtacag ttgtcaaaat   38220
aaggaaatta ataattgtgt caaactgtta ttctgtttat agaccttcta atgtccttta   38280
aaacaatcaa caaatcaaca tttttctggt caagaaccag taaatatgta tattctacat   38340
atatatatac acatatatat acacacatat attctacata tatatgtgga atatacgtat   38400
ttactccctc tgtccaagaa ccaatccagg attgttacct tcggttatca tgtatctttg   38460
gtctccttta atccaaagca gtttctttgt cttttatgac ttgacacttt tgaagattac   38520
aggttatttt gtagactgtc cctcaactag ggtttatctg aggtttcctt atgattagat   38580
tcagatattt atttttggca ggaatacaac agaaatgatt tgtgtgtttt tctcattgca   38640
tgatatcaga aagtgcattg tatatattta tcccattact ggggttgtta actttgatca   38700
cttggttaga gttgtgtcta ctaagtttct tcactataaa gttattttc  acttggtcat   38760 ttcatcagta tcttgtgggg agttactttg tggttatata aatactctgt ttctactttc   38820
ccttactata tttagcttct gtggacactt ttgcctgaaa cagttattta ctatggtgtt   38880
accaagtagt gatgcccttt tcttccatca ttctgtctac atttttttt  ttttttttt   38940 tttttgaga tggagtttcg ctcttattgc ccaggctgga gtgcggtggc ctgatcttgg   39000
ctcactgcaa cctctgcctc ccgggttcaa gcagttctcc tgcgtcagcc tcccgagtag   39060
ctgggattac agacatgcgc caccactcct ggctaatttt gtatgttcag tagagacagg   39120 attttttccat gttggtcagg ctggtctcca actcccgacc tcaggtgatc cacccacctc   39180
agcctcccag agtgctagga ttacaggcgt gagctgccac accaggcctt cttttctct    39240
```

```
tttaagagat agagtcctgc tttgtcacca aggctggagt gcagtggcat gatgatagtt    39300
cactgcagcc tcaaactcct gggctcaagt gaacctccca tctgtagctg ggactacagg    39360
cacctgcata acacctgact gttttttaaa actatttttag atgggggtc ttgcgaagtt    39420
gctcaggatg gtcttgaact ccgggtctta agtggtcctt ctgcctcagc ctctggatta    39480
gttggcatta caggcatgag ccattgtacc tggcaagtgc atattttctt tttttttttt    39540
taaggtggag tctcgaggcc gggcgcagtg gctcacacct gtaatcccag cactttggaa    39600
ggccgaggtg ggtggatcaa gaggtcagga gatcgagacc atcctggcta acatggtgaa    39660
accctgtctc tactaaaaat acaaaaaatt aactgggcat ggtggcacac gcctgtagtc    39720
ccagctactc gggaggctga ggcaggagaa ttgcttgaac ccaggaggtg gaggttgcag    39780
tgagtcaaga tcatgccact gcactccagc ctgagcgaca gaggtagact ctgtctcaaa    39840
aaaaacagaa agacggagtc ttgctctgtc acccaggctg cattgcagtg catgaactc    39900
cgcctcctga gttcaagcaa ttcttgtgcc tcagcctccc aagtagctgg gattacagac    39960
atgtgccacc acacgtggct aattttttata gttttagtag aggtggagtt tcaccatgtt    40020
ggctaggctg gtcttgaact cctgacttca ggtgatccac ccgccttggc ctcttgaagt    40080
ggtgggatta tgagtgtgag ccactgtgcc cagccaagtg agtatttgct tatgtagtat    40140
tttaattta tgattttttt ttcttttgaga cggaggtttg ctcttgttgc ccaagctgga    40200
gtacagtggt gccatctcgg ctcactgcag cctccacctc ctgggttcaa gccgttctcc    40260
tccctcagcc acctcctcct gaatagttgg gattataggc gcctgccacc atgcctggct    40320
aatttttgt atatctagta gtgatggagt ttgagcatgt tgccaggctg gtcttgaacc    40380
tctgacctca ggtgatccac ctgccttggc ctcccaaagt gctgggatta aggcatgagc    40440
caccatgccc ggccagagac tgttcattta ttttttttt ttgaggcgga gtctcgctgt    40500
attgcccagg ctggagtgca gtggcacaat ctcggctcac tgcaagctcc gcctcccaag    40560
ttcacaccat tgtcctgcct tagcctcctg agtagctggg actacaggtg cctgccacca    40620
cgcctggcta atttttgttt tgtattttta gtagagatgg ggtttcagcc cgccttggcc    40680
tcctggagtg ctgggattac aggcgtgagt cagggcgcct ggccaatcat accttctttt    40740
actgcattaa ttatggtttt ctttcgttct taaaacatgt ttatagtgac cacttttgaa    40800
attcttatta agtcagacat ctggttatac aagcaatttc tattgcctac ttcttttcc    40860
agtgggtggg gttatacttt cctgtgtctt agcttgtcgt tttttttttt gttgttgaaa    40920
actggacatt ttaagtaatg tagtaactct ggatacctca ttagcctatg gttggggtg    40980
gtggttgtta ctgttatttg cttatttgtc taatgactgg ctgaatgatt ttagtgttct    41040
atccttcttc cctccctgta cagtgtgaca cgtctgatgc tagtttctt gggatgcagc    41100
cttgggtatg cctaccatca ctctagaatc acagtgattt tggcatggct ttgtctcttt    41160
tcctgactgt acccagctgt taagctacac taattactag gtgatgctgt gtagtcattt    41220
cttggtgtcc ttgggggatt ggtcccagga ccccccgtt ggatataaaa atttatggat    41280
gctctagtcc ctcataaaat ggcacagtat ttgcatatac cggtgcacat cctcctgtat    41340
gctttgtcat ttctagatta cttataatac ctaatatggt gtaaacacta ggtaaatagt    41400
tgttatatat ttttttatttg tcttatttttt attgtatttta ttttaagtg ttttaatct    41460
cgagtgattg aatctgagga tgtgaaatct gcagatatgg agggcctgca ttgttttccg    41520
tggagctttg ggcctaaact gctccacaga ctgatctgat caaatttgcg cttctttgaa    41580
gggatagttt ctgagatcag tgtttgaaat ttgttccaat ccacagagga gtcctcccag    41640
```

```
ctctctttcc ctagttctgg ccaccaaact agacaactac aatttagcac ttatctccaa   41700
tgattctcct cctaccaagt gcctttgaaa gcatcattaa ctctttcata ccttgttgca   41760
aatgaaattt ctttgggaag agattgtgag ttttttttct cctaaattat ggtgcaatat   41820
aagtaatata ccatttttaac aattttaagt gtattaagtg ttttttttt ttgtagtttt   41880 tttttttttg tttttttgaga tagtcttgct ctgtcgccca ggctggagtg cagtggcacg   41940
atctcggctc actggaacct ccacttcccg ggttcaagtg attctctggt ctcagcctcc   42000
ccaaatatct gggattacag gtgtgcacca ccacgcctgg ctaatttttc tattttagt   42060 agaaacgggg tttcaccata ttggtcaggc tggtcttgaa cttctgagct cgtgatccac   42120
ccacctcggc ctcccaaagt gctgggatta caggccttag ccaccacacc tggcctatgc   42180 attgcttta tatgtatttt aaaattcata agttctcctc ctatgatgtt tttgtcccat   42240
gtgatttatt tgttaaaccg tcatctttgg ccgggcgtgg tagctcacgc ctgtaatccc   42300
agcactttgg gaggctgagg tgggtggatc acaaggttaa gagatcaaga ccatcctggc   42360
caacatggtg aaacccccgtc tctactaaga atacaaaaat tatctgggca tggtgacgcg   42420
tacctgtagt cctagctacc tgggaggcgg aggttgcagt gagccaagat cgtgccactg   42480
cactccagcc tggcgacaga gtgagactct gtctcagaaa aaaaaaaaa caaaaaactg   42540 tcatttttta tgttgcattt actgcattct ggatttaaac tgtgaggaac ctcatggtat   42600
cagttaatat attcttccat cttaatgttt ctcgtaaact ggtagatctg taaacttgat   42660
taggtctatc ctattgtatc acatcagaag cagaaggtgc tttttttttt ttttaaggga   42720
aattgtgtga aagtagacag aatggtaaag tgaaccctg cacacctatc acccagcttt   42780
aatagttatc agctcatacc attcttgttt gatttacaac cccattcatt tctcccttct   42840
gtattattat tatttagtta attattttt gagacagggt tttgctctgt caccaatgct   42900
ggagtgcagt ggcataatca cagctcactg ctgtcttgac ctcctgggct caagtgatcc   42960
tcccacctca ccctaccaag tagcggggac cacaggcgtg tgccaccatg cctggctagt   43020 ttttttatttt ttgtagaaac agggttttgc tttgttgccc agactgatct caaactccgg   43080
cactcaagtg atcctcctgc ctcagcctcc taaagtgctg ggattacaag catgagctac   43140
cacattcagc atgtaaattt ctttatatta atttgactgg cattttaagt cacacttgaa   43200
tttcatattt ggcaactatt aaaagcatag agtcctggat attagtgttt tgttaaacct   43260
gatctatcta atcataaata tacttaggtc taaaatatgc tcttggcctt tgtttattgc   43320
ggttcagtat ttgttactat attaaatagt aaaaatattg gtttgagata ctaatgaaaa   43380
gattaaaagt aaagcataac ttgaatggat acaaaaagaa acaagaattt agacttcagt   43440
ggatttcaga gaatactgct tcgatatgct aacattcctg ttgggtgtcc aaccgtgtca   43500
tagatcagtg gaaattagtg gtttctgcac tttactgtac tgttttttta tatgataata   43560
ttttcctggt tgaatgattc gttcttttga gtaaactcca tggtcaaaca attacttttt   43620
attagtcaaa gatgtaacca cataatcact aaaaagaaca gtgtgactta tttaaagggg   43680
attatgtttt taagtctttt atatagcttt gtagggaggc catatgagtt taaggacagt   43740
tcgtggcatt tgttcaaggt tttgtaactt ggcatctcag cagccaccag gataccgat   43800 catcgttcta agtaagattt aggcatttta gccttcatgt acagactata agtacacccc   43860
cccacacccc taccaaaact gtaaattcaa atgatgtttg aaaaagcata gaattttgt   43920 taggcgaggt agtttattcc ttgtgataca gttccagaga ggcagcataa cctaggaatg   43980
```

```
aaaaacttag acgtggaatc agatacacct ggtttaaata ccagctctac tgctcatgaa    44040
ctggatgatt ttggtcaaga tacttgactg ctgaggttca gtttcctcac ctgtaaagta    44100
gaggtgatag attagacatg ttgcatgtga agtacttagt atggtgtctg gttttgtagt    44160
aagatctata aaagataaat tattagtcat attccttaga cttcaggaat ttatctctgt    44220
gccatgtttg aggcaaacag ttacagaatt agaatgttag aaatgaaagg aatcctagat    44280
gtcatttaat tcaagtccat tgttttctgg atgagagaag aaagtgagga aaagtgacag    44340
agttggagac caagctagga ctggcctcag aatgttaaga gtactcttct agggatcgac    44400
cagtcgtgtt actagacttt ttggatctga attgtgcttt tccttgaatg ttttgaattt    44460
tggcttgagt gttgtgatta ttttattaaa atgagattcc agtcctattg tcatgactaa    44520
tgtttatgag aaatataaca tttcacttta atgatgtttt ttaattattc taaggggcct    44580
aatcttttc agtggaataa gctttaggtt gtattatatt ctataattca cttgaaaata    44640
gaattcatct ttacttgaca gccaaatttt gtgtactgca tcttttctga gggagagagt    44700
tggcaaggaa aggcacttgt tacaacgatc cacacatata gacgcatatt atttagaaat    44760
gaaagtgctt tgaatgattt agcttatttt cagttttttt ttttctgcag ttgtaatcat    44820
atgacctgtt tttcttcttt ttttttttt tgagacagag tcttgctctg tcaccccggc    44880
tggagtacaa tggggcggtc tcagctcact gcaacctcca cctcccaggt tcaggcgatt    44940
cttctgcctc agcctcccta gtagctggga ctacaggcgc atgccaccac acctggctaa    45000
tttttttatt cttagtagag atggggtttc actgtgttag ccaggatggt ctcgaactcc    45060
tgaccttgtg atctgcccac ctctgcctcc caaagtgctg ggattacagg catgagccac    45120
tgcgcccggc ccatatgacc tgttttcctt ttatagatgg gggagaaata tgggaagtga    45180
cttggtgtca gtcatctgtg ttggttaaat caagaatata atccgtgttt tgcttctgaa    45240
tagctcttta taacagtgat tggttacttt gggagtaaag attattattt agagacagag    45300
tcttgctttg tcgcccaggc tagactgcag tggaatgatc gtagcctact gcagcctcag    45360
actcctggac tctggtgatc ctgcctcagc ctcctgagta gctaggacta gaggtgcatg    45420
ccacatgcct ggctataatt attattaatt tacgtttagc attagttttt ttcttccagt    45480
aggctatttt actttatttta tttgattttg atgaagtttg attatttcta gtttgcttcc    45540
ttctatgacc cctacctgtt gtgggtctcc aggcaagcag tgcataggta gagccatcct    45600
taggtagcct ttagacttaa tattaggtga gctctcccca cagatagcct ctcctttatt    45660
tgaatggaat tatattttaa gtttggaaat atttttcagc ttatttagcc tgttgaattt    45720
aataaaaata atatttaatc ttttcagagg tcgaaacagt aacaaaggac tgcctcagtc    45780
tacggtgagt aactttaatg ttacttattg gggaaaatta gtagctaaaa catgatctct    45840
aaccacagac caaatgccaa ggcaaaagat tcccttcttt tgaattttgt catagataac    45900
ttgactgttt aagtatgtta ttagcctata tgtgtttttt taatgactct gtataaaatg    45960
tacaattact tgttgtatta gtccattctt acactgctaa taaagatata cctaagactg    46020
ggtaatttat aaaggaaaga ggtttaattg actcatgctc tgcattgctg ggaggcctc    46080
aggaaactta caatcatggt ggaagggga gcaaacacat ccttcttcac atagcgcag    46140
gagagagaag tgctgagcaa agcagggaaa gcccttata aaaccatcag atctcctgag    46200
aactcactca ctatcatgag agcagcgtag gggaaactgc ccccatgatt cagttatctc    46260
cacctggtct tgcccttgac acacgagaat tattataatt aaagataaga tttgggtggg    46320
gacacagaac caaaccatat catttgtaaa tagtattttt gtcacgtgta ataacaagaa    46380
```

```
caagtcgctt gttctttcct aaatgactaa gtgcaaatct aagtgaaaaa cctccaaaag    46440
atacgtagaa caccaagagt ggagtctgca gagttcttta tgcttttat  tttgaattaa    46500 tgtgctttt  ttctgctgct ttcattttc  tcctttggct ttctggtctt aaattttgga    46560
atgttatcaa tgaaattgaa ccggacatga agggcagaaa ctataagtcc cacatgatgg    46620
aagaaataaa tgagaagcta tcacaaattt ttgagacttt gcctttatta gattgtttta    46680
caagaatcag gaagatatac acgtatatgg tagtaatatg gagtagtgtg gttgatcaga    46740
cttaagcact gtcactgatg ctgatatgct gggagaacct agtcagggtt cttctatgaa    46800
ggtatgacct ggcttcctac cccatttatt tatacttcac ccttcttagg gtacatttct    46860
gtgagtttta acaattgcat acaatcagtg taactaccac cacaatcaag ttaatagaac    46920
agtttcattg cccaccaaaa tccctcaaat cacttttcag tgaaccctcc tctctctcca    46980
accattgatt tgtcttccat ccttacggtt tgtgtccttc ctcctctatg aagtttact    47040 cttgctttt  tatgtcatgt ttagtcaaaa caccattagt tggtttgact gataacactt    47100
gaaaacctga ccttctgttc cttctgttct ctatggaagc aaaatattaa ataaacaaaa    47160 tcttcccta  atacatgtaa gatatcataa acctaactaa acattttgca acaaataata    47220
aacgttagct ttatatgcaa atgtaaatac aggctgagca tccctaatcg gaaatgctcc    47280
aaaatttcat attttgaatt agggatgttc aagcactaag tataatgcaa atatccccaa    47340
atccgaaaaa aatccgcagt ctaaaatact tctggtccca agcatttag  atgaggaaga    47400 ttcagtttgt actaatttct aatagttttt ttttttttta atattccaga tttcttttga    47460
tggaatctat gcaaatatga ggatggttca tatacttaca tcagttgttg taagttatta    47520
gattattggg gataaactgc cttggggta  gaataaagta attccatgaa gttaaaatgt    47580
ggataaatga ttgtcaaagt aacattgctt agatcatgtt tagtcaggat gatttagaga    47640
aatagattag aactccttt  atccagtcta atataattca ttgtaaaagt acagttggtc    47700
ctctgcatct gtgggttcca tattcatgga ttcagccaac cttggatcaa aaatatttgt    47760
taaaaaggcc aggcacagtg actcacgcct gtaatcccag cactttggga gtttgaggtg    47820
ggcagatggc ttgagctcac aagtttaaga ccagcctggg caacatggca gaactccgtc    47880
tctacaaaaa gtaaaaaaac tagccgaacg tggtggtacg tgcctgtagt cctagtgact    47940
tgggaggctg acgtgggagg attgtttgag cctgggaggt ggaggtttca ctgagctgag    48000
ataatgcccc tgcactcagc ctggtcaaca gtgccagaca gacccttct  caaaaaaaaa    48060 aatttttttt tttttttttt tttttttttt ttttgagaaa aaagaggcat ggttgcgtct    48120
gaaccaaaga tgtacggacg tttttcttgt cattattcct aaaacaatac agtatgacaa    48180
tttacatagc atttacatta tattaggtat tacaagtaat ttagggatag tttaaagtat    48240
ttgggagaat gtgcttagtt atatgcaaat actattacat tttatgtaag tgacttaagt    48300
attatgtaat tcggtatctg aaggaggtcc tggaaccagt ccctaccaa  taacaacaga    48360 tagctgtatt cttgttaacc ctgctgtgtg tgtaaaataa tgttagtagt tgattgtctt    48420
ttgtacatta ttttgtcact taaaatagct ggggtcagaa atgtttgact tcagtattaa    48480
aattcgtact gcaaactctg agtagagcct cctgaagaat ttcaagagtt cagtgtattg    48540
ttaatgtttt gaattttttt tattgttttg ttagtgaata cctaatattg aatgaagcct    48600
gatgaggtat aaaagtaaa  atgaaaacaa atatccctgg tgaccgggta gtatactgtt    48660
tctttgataa ataaattata tgttttagg  gctccaaatg tgaagtacaa gtgaaaaatg    48720
```

```
gaggtatata tgaaggagtt tttaaaactt acagtccgaa ggtaatttt  acttttttc    48780 ttttcttac  aaagtaaaag aacattttca tagtcagtgt tttacctagt ttttaaagcc   48840
actttgaatg atttacttc  tcagtttcaa atactgatta ttttatagac tggttgtgt    48900 aatcagagag gcttcttgat gtgtgtgctt attaaaatat ttcaaccatt tttaagcatt   48960
gtgagctaat agagggatgt ggtggtttgt ttttcctct  taaaaattat tattaatgta   49020
cttaagacaa accatagaaa caaaaaacat ttagatatga ggattttaa  atgatggaat   49080 ggataataga tcatatgcct gggaaaaagg gtatgattct cttgagatta tttttgtcaa   49140
aggcatataa gaactggtac cttgatgagc taaagaattc ctaacaaatt ttattttgta   49200
aaggtttgga gtacttactt gtgttttca  ttttagtgtg atttggtact tgatgccgca   49260
catgagaaaa gtacagaatc cagttcgggg ccgaaacgtg aagaaataat ggagagtatt   49320
ttgttcaaat gttcagactt tgttgtggta cagtttaaag atatggactc cagttatgca   49380 aaagaggtg  ggttttgatt tcctaaatat gcctcatggt ttattagatt tattcaagca   49440
aagattttca cagtgatctt acaaacttt  tttaaagaaa tatctgggct gggtatggcg   49500
gctcattcct gtaatcttag cacttaggga ggctgaggcg ggtggatcac ctgaggtcag   49560
gagttcgaga ccagcctggc caacatggcg aaacccgtc  tctactaaaa atacaaaaat   49620
ttatttttgt gtgtggtggc gtgcgcctat agtcctagct actagggagg ctgagacaga   49680
attgcttgaa cccaggaggc agaggttgca gtgagctgat accgcaccac tgcactccag   49740
cctgggtgac agagcaagac tccgtttcaa aaaaaaaag  aaagaaaaaa gaaatatcta   49800
ctttctagaa tagcccaagt aaggtaattt tttagaaaaa tgagaatgtt aatgcatttt   49860
tgttggaaaa caattagaac tttagagaaa aattaaatag agtttttgtg atctcttaaa   49920
aaattagttt gtaaagcatt ttctacagtt ttgtggtcaa gaatgctact gattatattc   49980
aactgaaaat ttcttgtccc atttggccta caatgcttta gtttataagt gggcatgtgg   50040
caaatctgga aagaaatcaa agtataaggc taaggaagaa aggtagagaa cggttggtag   50100
aaaacaattg tctaatgaaa atgaaaaagg gtgaagaagt agaacatacg tattttaaaa   50160
atattcagag tatgagacaa ggtttgaga  atttaaaagc gattatgtag ttatattaaa   50220
aatttagtct cttttaagt  gtccattgat gaacaaagtg ggaattcctg ttactcattt   50280
gcaaggcatt attgagtgtt cagtaacacg ttgcaaggca cttctgggca atcctgaact   50340
tggttctcaa attctttttt ttttttttt  tgagacggag tcttgttctg tccctgggt    50400 ggagtgcagt ggcacgatct cggctcactg cagcctctgc ctcccaggtt caagcgattc   50460
tcctgcctca gcctcctgag tagctggac  tacaggcgtg tgccaccaca ccaagctaat   50520
ttttgtattt tttgtagaga cagggtttca ccatgttggc caggatggtc tcgattgttt   50580
gacctcgtga tccgcccgcc tcggcctccc aaagtgctgg aattacaggc atgagccact   50640
gcacccagcc ggttctaaaa ttctttat   tatttgtata tgccaaattc tgtagtgaaa   50700
tacgtaattc tgttgtaaat tgtagttcag tacaatttga ttttcactat tcaaatctat   50760
accaaaagct gttttattg  ttgggctgat tcttctacac tgttacttgg aaataataat   50820
ataccaggat tctttctctt agacttagga gtctttctct ttgcttgctt ttcagaggc    50880 taacagtact gggtattctt taactgtctt gatatgctga tgaaagcaca gtgttctgtt   50940
tttgaatctt ctcaaatgtc cttgtctttg attcacaact ttttgtctta agaggccttc   51000
agcatcccat acaaggaaac aagtcttttt ttagctgcta cctttggagt tgattttgtt   51060
tatgtctagg agcactaaat tatttatact tatactattg aaatattcct ctgttataaa   51120
```

```
ttcaaaaatt gactttggaa gataaaattt tagttgaatt taatacatag cactctggaa    51180
agagtattgg ccacaacaaa aaaaaaggtt ccctactcta ttggatacca ggtcatttaa    51240
cagccattta cggtatgcat tgtctttttg ttttatgat gaattgatat ttcccaaatg     51300
tggaagagtg aatattactt tgagatgttt gtgatagtcc attccttgct cctcttcaaa    51360
attaatgtca ttaaatttt attactttat tagatcttca tttctcagat aattttagtt    51420
cattatagaa aggcaagaaa atacagatca gagtgacaac tttgaaaatc tcactctact    51480
cataagggga tgggtgtatt ttgctatata ttacaaaatt agttttcttg atgaggacat    51540
ccactattgg agtaatttca ggtatcttat tttttcttt ctctctcttt ttttttttt     51600 ttttggagac ggagtttcgc tctgttgccc aggctggagt gcagtggcct gatctcggct    51660
caccgcaacc tctgcctcct gggttcaagc gattctcttg cctcagcctc ccgagtagct    51720
ggttactgag gcatgtgcca ccatgcccgg ctaattttg tattttagt agagacgggg      51780 tttcactatg ttggccaggc tggtcttgaa ctcctgacct tgtgatcctc ctgccttggc    51840
ctcccagagt gctgggatta taggcgtgag ccaccacgcc tgggcaggta tcttatttca    51900
aaacttacag tggtttagtg aattataaa ttgcgtccag tgcgtagtat cctgaaaata     51960
gtattaagtc atgtgtttag gacatcaggt ctcttaagct aagactatcc aggcagaaat    52020
tgccctcttc tataaaagaa gaaaagtatt aattaggaag tactatcagt atggagaaaa    52080
ccattttaga attattaatt ggcatggttt ccttcttttt tttttattt cgagatggag     52140 tctcactcta tttcccaggc tggagtgcag tggtgcgatc tcggctcact gcaacctctg    52200
cctcctgggt ttaagcgatt ctcctgcctc agcctcccga gtagctggga ttataggcac    52260
ataccaccat gccctgctaa tttttttttt tgtttgtatt cttagtacag actgggtttc    52320
accatgttgg ccaggccgca tggttttcct taataacaaa attaaggcat ttattactgc    52380
atctagattt ttttatttt ttattagaga cttactcaga ttactcccaa agtaaaggaa     52440
ggtatggttt aatcaatgct tcttaatgct gggttcacgt ttagtcacct ggggagtttt    52500
taaaaatgtt ctcacttcta gggatcctgg tttaattata attagcctgg gtgaggctct    52560
ggacagtcag ggtgtgagct atgggtttca tgtgatgaga tcccaggagt ggctctgttc    52620
tgtggccttg agaatttgtg ctttctaggc caggtgcggt ggctcactcc tgtaatctca    52680
ctttgggaga ccaaggtggg cagatcattt gaggtcagga gttcgagacc agcctggcca    52740
acatgttgaa accccgtctt tactaaaaaa gtaaaaaatt agcgggacgt gatggcacat    52800
gtctataatc ccagctactt ggggagaggc tgaggcagaa gaatcgcttg aacccgggag    52860
gcagagattg cgagatcatg ccactgcact ccagcctggg caacagaata aaaaagaat     52920 ttgtgcttta ttttcttgcc tcacagtccc cttctgtct cagaattggc aactgcctga    52980
aatagtctct gctgttatca tttgatagta cttttccaca tcttgaatgg atagatagag    53040
tgttttttat aatagaagtg gatgaatgat tagagtatac taatatgaca ttgtattttc    53100
ctaaaagata tgaattgatt tcatttctga gcttttataa ttctcttctg taatagtctg    53160
tcaaattatt aaggttgata atattaacta aaatttgagt gcatattcta tgtgccagac    53220
tctgtgctaa cagatttacc tacatttgtt cacataatca tcacaagttg tttctgtagt    53280
agatacagct attatccacg tcatagatga ggaaacaggc atatttagga aacttgctaa    53340
agtgaggaca caaatctagc ttttctactc taactcatgt tcttaacatt atactgcagt    53400
gacataaatt atgtggtttg gtttgttgtt tatctcagtt gtcataagtc gaattaatgt    53460
```

```
ttgtttgttt gttttgagac agagtcttgc tctgtcgccc aggctgggta cagtggcgtg    53520
atcttggcgc actgcaacct ccacctcctg ggttcaagca gttatcttgc ttcagcctcc    53580
ctaataactg ggattacagg cacgtaccac cacacccggg taattttgt attttagta     53640 gagatggggt tttaccatgt tggccaggct gatttcaagc tcctgacctt aggtgatcca    53700
cccacctggg cctcccaaat tgctgggatt gtaggcatga accactgtgc ccagccagta    53760
agttccatgg ttgttaaagg atttctccac aaataaagct aaaagtaaaa aaaaaaaaa     53820 aaaaaaaaa ttctcaagca atataagatg cagactatta tgttgttcaa gttttttttt     53880 tttttttta atctttggct ttattttgg ggaaacctt ttttctttt ttgttttcct       53940 tgggacggag ttttgctctt gtcgcccagg ctggagtgca atggtgcaat cttcgctcac    54000
tgcaacctcc gccttctggg ttcaagcgat tctcctatct cagcctcccg agtagctggg    54060
attacaggca tgtgccacca tgcccggcta actttgtatt tttagtagag actgggtttc    54120
tccacgttgg tcaggctggt cttgaactcc tgacctcagg tgatccacct gcctaggcct    54180
cccaaagtgc tgggatcaca agcgtgagcc accgcgccca gccagggaaa cctttatttt    54240
gaggcggagt ctcgctctgt cacccaggct ggagtgcagt ggcgtgatct cagctcactg    54300
caacctctgt ttcctaggtt caagcaattc ttctgcctaa gcctcccgag gagctgggat    54360
tataggcgtc tgccaccatg cccagctaat ttttatattt ttagtagaga cggggtttca    54420
ccatattggc caggctcttc tcaaattcct gacctcatga tccacccacc ttggcctccc    54480
aaagtgctag gattacaggc gtgagccacc acactcggct gctggggaaa cctttaaca     54540 tgagtaaggt cagtgtgact tttaagttct tgatgctaac atcattgatt tcaataaagt    54600 ttaaagtta tattcatgca tatatgcaaa tgaataaaag ctttgaaat agtgacttct      54660 tacggtacag tgaataagtt tcctttggtc tcttgaatgt tatacatgtt ccagtttgat    54720
ttactgagaa actgaaagta cctttacgtc atatgagctg tgagtcacct tggcacattc    54780
ataattagaa gagaccatca gattatcatt ggaaaatcag tttgtattta cctttatttt    54840
gaattccagt gcagacagat ctgaggttct cttcattttg ctaaaacttc ttagggcctt    54900
cagtcgcttt tggctctgta ttcgtgtatc tttggaattg tcctgttatc tctgcttgtt    54960
ttttacttga ttttccatcc atttccagta ttcctttctc ctctattttt ttccttcatt    55020
ttctttctgc tcttcctgtt gcgccattat tcatgttttc ctctttactc caactcaact    55080
atggctttac ttctgttttcc ttattccatt gttcctcata cttttttccta ctgcttcatt    55140 ttctttgcag tattctcagc ctagatgata ggggtcagca atctgctca tcagtaaata    55200 aattttattg tagcatagct atgcccatgc gtttgtgcat tgtctatggc tgttttgatg    55260
gctgtagcca tagagttgag tagttgtagc tgactgtagg acttgcaaag ccagaaaatt    55320
tgactgtctc tttacagaaa agtttgccag ctcttggcct aaatcatatt ttccgctgca    55380
tttagggctt tttaggactg atcaaaaata catgctatac tggctttggt gaagtaacag    55440
aatgtgctct gtcctttaaa cttacaacta attgcatgct ttgattctaa tactgtataa    55500
tatcctgcga ttcttattca tgaccattct aattggattt agtctgaaga attacttttg    55560
cttaacagat tctttgtcac atttagtgaa aaatcataaa aggggaaggt tggttaatgg    55620
aaaagatctc catcaactaa ccactacctt cctatctac aaatttatct tcttcctccg     55680
tgccatcttt ttttttttt ttttcagatg atcttgctct gttgcccagg ctggagtgca    55740
gtgatgcaat cacagctcac tgcagcctcg acttcccagg ctcaggtgat cctctcacct    55800
caacctccta cataactggg actgtatgtg cacatcacta tgcctgacta atttttata     55860
```

-continued

```
tttatatttt ttgtagagat ggggtttccc tgtattgcac aggctggtct caaactgctg   55920
ggcctaagag tcttcccacc ttggcctccc aaagtcctgg gattacatga gtcaccgcac   55980
ccggcctcat tattatttttt cctctggttt tagtagagag gatttttaag ccaacttcaa   56040
tcatgccctt gactctctcc cttctactta cctccttgtt ctcttttttct tttcttttt   56100 ttttagatgg agtctcggtc tgtcacccag gctgaagtgc agtggcgtga tttcagctca   56160
ctgcagcctc agcctcctga gtagctgggg ctataggtgc ctgccaccac gcccggctaa   56220 ttttttgtatt tttagtagag atggggtttc accatgttgg ccaggctggt ctcgaactcc   56280
tgacctcaag tgatcacctg cctcagcctc ccaaagtgct gggattacag gcgtgagcca   56340
ccacgcctgg ccatctttttt ttttctcctt gctcttttat accacttctc tgtttctggg   56400
ctcttcaaca tctgcctttc tagttaatct ttccctttag catgaaaacc tattcacttc   56460
ctgctcatcc taaaaaggat tctttttttgt tttgtttttgt ttttgtttttt gagacagagt   56520 ctcgctcttg cccaggctgg agtgcagtgg cactatcttg gctcactgca agctccgcct   56580
cccgggttca cgccattctc ctgcctcagc ctcccgagta gctgggacta caggcacctg   56640
ccaccacgcc cagctaaatt tttgtattttt tagtagagat ggggtttcac cgtgttagct   56700
aggatggtct cgatctcctg accttgtgat ccatctgcct cggcctccca aagtgctggg   56760
attacaggca tgagccaccg cactgggccc aaaaggattc ttttttaatcc tgaattcttc   56820 tagccattat cctgcctaag gctacgatta acctctaact gccaggtcct ttggaatctt   56880
tttctgtctt tattgctgca cttgaatgtt ggtttcaccc tccttcagaa tttcctcttc   56940
tgtatttttt atgtttattg atcattcctt ccctgcctca ttcctgggct tcttttcctt   57000
cacacacccc ttagatgtgt gtccccagtg tttgtttctt tgcctgctgc tcttgccaca   57060
tgacacacac tgccagctac cacacacaag ttccctccta tcatgtgtgt atcattgccc   57120
ttataccatg ttgtattaaa attatatgct tgtctcccct gttacagttt gagctctttg   57180
tgctccaagt aaagacagtg atactgtctt tattatttat tctcatggtc tagtatagtg   57240
ctttggcaca tagtacaggc tcaatataaa tgtgtttgaa taaatgaaat tcagtgcctt   57300
aatacacttt tgtagaagca ttatttttatg gaaagaatga aaaagctgta agtggtctta   57360
catatatagt catccagcag atacttagag agctctggga tgtgttcctt gctgtgcttg   57420
ttgctatgga cagtacggag aaatacaaga atctattttg ggtcccttttt gagaacctag   57480 tgaaactgtg tacctagtga aactgtatac cctcacccta gaaaaattta cacacatgta   57540
gattttacat gtaattcttt taaaaattaa ttttttttct ttttttttaaa gaaacagggt   57600 catgctctgt cactcaggct ggaatgcagt ggtgtgatca tggcttactg tagcctcgac   57660
ctcctggctc aagcgactct cccacctcag cctcccaagt agctggggct acaggtcac   57720 gccgctatgc ccggctaatt tttaaaaata ttttatagac actggttctc actatgtttc   57780
ccaggctggc ctttacctcc tgggttcaag caatcctcta ccttggcctt caaaagtgat   57840
gggattatag gtgcaagcca ctgtgcccac gctaatgtaa tttcatggtg ttcacagttt   57900
cttcagggag ttcatatacg ccatgtactc tattctaagc attttagag ttagagatag   57960 caaagcacgt gaataaattc aagaaaaatg gaatgttgta ctgcatgaca ttgaatatca   58020
aatggagtca gcgatgcaaa taattgtcta gattttacaa aaaaaattag cctggtgtgc   58080
tggtgtgcgc ctctaatccc agctactcgg gaggctgaga caggagaatc atttgaaccc   58140
agaaggtgga ggttgcaatg agctgagatc gtaccactgc actccagcct gagtgacaga   58200
```

```
gcgagactcc atctcaaaaa taaaaaataa aagaattgtg tagattttag tagttggaag    58260
aagttggagt gttaatgtgt aattagagaa cagtgagaaa taaaattcta cagattgttt    58320
tattctggtg tgctgttgtg ttctcatatg gttgtctttt tggtcttgat agtgtatcag    58380
taacagagta cgagtaacaa acagggatct cttctgaacg gcgtgacatt agaaaagctg    58440
tttacggcct caactttgct gtggtttatt aagacacaga tatgtgttca ttctggggcc    58500
aagcagtaac tggagagtgg cacttattga ggccagtatg gaggcagtac agagattatt    58560
gagattaaaa gaaagaaaca ggtggaacgg atctatgtaa tggaaagcta aacagaatag    58620
ttcgtggtac acagtagaaa agcattacat gtttattaag atatggtcat cttccattta    58680
ttaaagttac atgttttata atttttagag tatatagaaa ttctctaccc tatcatgttt    58740
gccaaagtca gaacaataac ttcatttatt aaatatAaaa aaaataaaaa cctctagcat    58800
aaaatagaat tttatttgga caaacgataa aaaaatactg tgtggtacta gtaagagtaa    58860
ggttgattca agatacatgg gagcagaatc caaagtgtag aaataggcca ggtgcagtgg    58920
ctcatgcctg taatttcaac acttttggag gctgaggcgg gaggatgagt tcaggagttc    58980
aagactcgcc ttggcaactt ggcaaaccc catctctaca aaaagtacaa aaattagccg    59040
ggtgtggtgg tgtactcctg taaacccagc tacttggtgg gctgaggtga gaggttcact    59100
tgcagccagt aagtcaaggc tgcagtgagc tgtggttatg ccacggcact ccagctgggt    59160
gacaagcaag accttgtctc aaaaacaaac cagccaggcg tggcggatca cctgaggtaa    59220
ggagttggag accagcctgg ccgacatggc tctactaaaa atacaaaaat tagctgggcg    59280
aggtgacggg cacctgtaat cccagctact tgggaggctg aggcaggaga tcgcttgaa    59340 tccaggagac ggagtttgca atgagccgag atggtggtgc tgcactccag cctgggtgac    59400
agagccagac tctgtctcaa aaacaaaaat aagcatagga catggggata aattgaagat    59460
ttatgaagac acagctgaag gagacataaa agtagatttg gctaaatgga acatgccat    59520 actttgaatg gaattattta atactacaac gttgtcaatt ttcctcaaat aaatctctaa    59580
agataatata ttcagttttg gccgggcacg ttggctcacg cctgtaatcc cagcactttg    59640
gaaggctgag gtgggccgat cacttgagga cgggagtttg agaccagcct ggccaacatg    59700
gtgaaaccct gtctctacta aaaatacaaa aatcatctgg acatggtggc aggtaccagc    59760
tacttgggaa gctgaggcag gagaattact cgaaccccgt aggtggaggt tgcagtgagc    59820
tgagattgca ctccagccgg gtgactccat ctcaaaaaaa aaaaattt tataatatat    59880 atatatatat ccgttttgt agaaattgac aaaatgattc taaagcttat tagattatgt    59940
gtattaacag aagaactttg gaatttttt tccacaagag tcataaagga ggacttgccc    60000
tacaaaatat gtcagaatta aaacataact tgtcagctgg gtgcggtggc tcacgcctat    60060
aattccagca ctttgggagg ctgaggcagg cagatcatga ccagcctgac caacatggag    60120
aaaccccgtc tctactaaaa atacaaaatt agccggtcat ggtggcgcat acctgtagtc    60180
ccagctactc ggaggctga ggcaggagaa tcgcttgaac tcgggaggtg gaggttcag    60240 tgagccgaga tcgcgccatt gcactccagc ctgggcaaca gagtaaaac tctgtttcaa    60300 aaaaaaaaa aaaaaaaaa gaattataac tgtcacagtg gctacgtatg gagcatccaa    60360
aactgaattt atgtgggtat tttattaata tgcaatatag cactttaatt ctggaggaaa    60420
ggtggattat tcagtaaatg attctggac attggggaca aattagatac ctacttcaca    60480
ctgataaata aaaccaaata gattaatgag aaaactgtga ttaaacaaaa caacacccag    60540
actacactgg agcaaatctg tgaatttgtt taattttgag tggagaagga ctttataagc    60600
```

```
atgactacca gagcaaaaaa atcatgaagt aaaagatcga tacctttgat tataaagaga   60660
ttaaagattt aggccgggtg tggtgctcac gcttgtaatc ccagcacttt gggaggccaa   60720
agcgggtgga tcacttgagg tcaggagttt gagaccaacc tggtcaacct ggtgaaaccc   60780
catctctact aaaaatacaa aaaattagt caggcatggt agcacatgcc tgtaatccca   60840
gctactcagg aggctaaggc aggagaattg cttgaatttg ggaagtggag gttgcagtga   60900
gccgagattg tgccacatca ctccagcttg ggcgacagag tgactccatc tcaaaaaaaa   60960
aaaaaaaaaa gacttagacg tgtccaaaag taccatacat ttaaaaagac atgccacaaa   61020
ctgggaaaag tagaaaaata gttttaaaaa tgaccagtga atgtatgaaa aggtggccct   61080
cctcacttgt aatgatttaa gaaatgcagt ttatttttat tttattgtat ttttaaagaa   61140 attcagttttt aaagcagtgg aatatgattg tctatcagct tgcgctgaat ggtaaatgtg   61200
agaaagatta ctactactta gtggtactga gggagttgca aaacacttaa cactgctagt   61260
gggatggtta aagtaaaaca gtagcattc ttaaactctc tattaggtaa agaataggta   61320
agtaatgcat atgtttccag gacatttttca gtaagactgt ttactgatag ggttgtgtaa   61380
tgctaatata cttactatct agttttagta ttattttttt ctcttgtctt ggatggtttc   61440
aatggagtct tatgcatgca gatatattaa aactagtaat aaagcaagag aaggaatgtg   61500
gataaattat ctctaatttc tattttgttc tatttctatt tcatactcct gggaaagaat   61560
attaagtggg catgtgtact tgaacagttg ttctgttttt tattagaaaa gaatccgaat   61620
ctataaaatg ttttacatat ttgccaggga aacagaaaag atatttgtac agctgtaaga   61680
attggaatta atttcatttt actgactttt ccttaaccta attctgaaca cttttgccat   61740
aggtttgaga ataagttgtt ataaaatgac tactattctt cactaatagt attggcattt   61800
caattcctaa attctgtttt tgattcttg aacatttctg aatttacttt ttttgtctta   61860
gttcttctac agaatcattt tcttcttttt tcttttttta ttttattttt ttattttga   61920 gacagagtct tgctctgttg cccaggctgg agtgcagtag cgcgatctcg gctcactgca   61980
agctccgcct cccgggttca tgccatttttc tcctgcctca gcctcccggg tagctgggac   62040
tagaggtacc cgccacagcg cccggctaat tttttgtatt tttagtagag acggggtttc   62100
accgtgttag ccaaggtggt ctcaatctcc tgacctcgtg atccatccgc ctcggcctcc   62160
caaagtgctg ggattacagg catgagccat cgcacccggc cttctttttt tctttctctt   62220
taacttctga gctgaaaata gtaccttttta taaagaagtg ctcaaacgat gattggactg   62280
atttctcctt atttctctct ttctctctgt ctctttcact ctcttttag aatttttctt   62340 ttttaagtag agacgaggtc ccactatgtt gcccaggctg tcttgaactc ctgagcccaa   62400
gcaatcctct ttgcctcagc ctcccaaagt gctcggatta caggcttaag ctatcacacc   62460
aggcctaggc taatttcata ttttgagatg gcacaaattt ctttcaggta gctagctttt   62520
cctcctcctc cccacttaaa atagatcctg atccagaagc ctaatggaga aaatgaaaac   62580
agaatgttca cccataaaca gtatctttgt attggaatct tttctaaaac ttcttttgat   62640 cttttttagga gatagtgtgg gaatcagcaa tctagtatta cgtacgtgga atctgtcacc   62700 ttgtttttttt aaatacagca aacctcatga agtgaatttc catattttttt cttgttcttg   62760 ttagttttgc accactcagg ctttgctgta gaatttgatg tatatttgat tctgtagagc   62820
atgggctatt gatcttcact cagctttcag aggaatctga ttagtaagtt tgagttttttt   62880 attatttttt agttgatttt gaagtaaaat acagcaccat tttaactgat accatttcta   62940
```

```
aacaattttc agttcaaatt ttaagttagc taatttagag cttaagaaaa ttgctttaaa    63000
aacataaaat tactggctgg gtacagtggc tcattcctgt aatctcagca ctttgggagg    63060
ccaaggcaga tgaattgctt gagcccagta gttcaagacc agcctgggca atatggtgga    63120
accccgtttc tacaaaaaaa atacaaaaag tagccagaca cggtggtatg tacctgtagt    63180
cccagctatt cgggtggcag aggtgagagg atcatctgag cgcagggaga ttgaggctgc    63240
agtgagccaa gtgagaccct ggtttcaaaa aaaaaaggt tactaattgc agtgcctttt    63300
atcttattta atgggcttag tcaaactaag atgatgtatt ttatcttata aatgttttcc    63360
cttgaatttt aactgaagaa tccaatttgt acctctcaca aacagaatgt attagtaagg    63420
aaaataaata ctgcttttta ttacttaaat aggatatatt tttctcttag gattttttt    63480 tctattttat ctcactttat cgtagtgcta gaaaatttaa tcattcattt gagatagggg    63540
gaaaattagg tttttttttt tcttctattt tgagacaggg tctcattttg ttgtccaggc    63600
tggagtgcag tggcgccatc gtagctcacc ataacctcaa actcatgggt tcaggtgatt    63660
caccttagcc tcctgattaa gctgggactg cagatgtgta tcaccactcc tggctaattt    63720
ttgttgttat ttttttgtttg atgaggtctc attatgttgc ccaggctggt ctcaaactct    63780
gggcctcaaa tgatcctcct gccccagcct cccaaagtgc tgggattaca ggcatgaacc    63840
tctgctccca gcccattttt taaaatatat tcacagcatt gtgcaaccat cactacaatc    63900
aatttacatt ttcatcaccc tgaaagaaa ctctgaaccc cttagcagtt cctctctgtt    63960
tgtttcaatt ttccccagct ccaggcaact attgatttat tgtcttcata ggtttgccca    64020
ttctggacat tgcgtattaa tggaatcata taatatatag cctttttttt tctttttttt    64080
ttttgaaaca gagtctcact gtgtcgccca ggctggagcg cagtggcatg attgcagctc    64140
actgcatcct ctgcctccca ggttgaagcg attctcctgc ctcagcctct tgagtagctg    64200
ggactatagg cgcctgccac cacacctact aattttatat ttttagtaaa gacggggttg    64260
caccatgttg gccaggctgg tctcgaattc ctgacctcaa gtgatctgcc cacctcggac    64320
tcccaaagtg ctgggattgc agccatgagc caccgcatct ggccatatat attatgatag    64380
gcttgtttca cttagtatgt ttcttccatg ctgtagcatg tattagtact tctttcttt    64440 tcatggccaa atattccatt atacagttac acaggtacac tacattttgt ttattcatca    64500
gttggtggac attttcattg tttccacctt ttgattata cataatcctg ctgcgaacag    64560 tgactttaa agttttgtg tgggccgggt gtggtggctc atgcctctgt aatcccagca    64620
ctttgggagg ctggggctgg cagatcattt gaggccggga gttcgagacc agcctgccca    64680
acatggtgaa accctgtctc tactaaaat acaaaaatga gctgggtgtg gtggcgtgca    64740
cctgtaatct cagctactag ggaggctgag gcagagaatc acttgaagct gggaagccga    64800
ggctacagtg agccgagatc acgccactgc actccagcct gggtgacaga gtgaaacttc    64860
atctcaaaaa aaaaaaaaa aaaaaaaac tgcgtgtgga cataggtttt caattctcat    64920
gggggtgtgt gtgtatgcat actcatacat acatacacat acctgcaaga taattgctgg    64980
ctcgtatgct aaatctatgt tgaaccttt acataactgt tgggctgttt tgttttcttt    65040
ttattatttt ttgaaaatag agttgggtc tcactgttgc acaggctgat ttcctgggca    65100
tagtggctgt atcattttac aatcctacat agctgtttcc aacgtagctg tatcatttta    65160
caatcctact agcagtgtct gaggtttctt atgttttca catcctcacc agcatttgtt    65220
attgtctgtc tctttgatta tacccatcct agtgggagag taagaagtag tatctcactg    65280
tagatttttt ttttctgttt acaactttac tttaaaaatt atatatgcac acatggtaaa    65340
```

```
aagttcaaaa cgtgtgtacc aaaagattta acagtgaaaa tagaaaataa gtgtggtcct    65400
tgttttcttc caccaaggca aatattgtta taatctccta aacaacttgt cttccagatt    65460
tctcattttc agtcaatctt gggcattgac ataaagaaat tcttagacat tgcttttatt    65520
agatcatctc atcccttgct caaaatcttc agtggccact gttgtttaca gaataaagtt    65580
gggatgctat acagggccct tcccagtgga acttctcttt ttcaaccttta tctctcatta    65640 tttcccaatg tttttttttt ttttttgag acggagtctc gctctgtcgc ccaggctgga    65700
gtgcagtggc gggatctcgg ctcactgcaa gctccgcctc ctgggttcac gccattctcc    65760
tgcctcagcc tcccaagtag ctgggactac aggcgcccgc cactacgccc ggctaatttt    65820 ttgtatttttt agtagagacg gggtttcacc gttttagccg gatggtctc gatctcctga    65880 cctcgtgatc cgcccacctc ggcctcccaa agtgctggga ttacaggcgt gagccaccgc    65940
gcccggccta tttcccaatg ttaatctact tattgaccta ctaagctggc atgttctgtg    66000
tgttagacat caccaacttt gtgccttctt ttttgtttg tttttgagtt ggagtctcac    66060
tctgttgccc aggttggagt gcagtggcgc gatcttggct caccacaacc tctgcctccc    66120
gggttccagt gattctcctg cctgagcctc ccgagaagct gagacgacag gcgcgcgcca    66180
ccatgccctg ctaacttttg tattttttagt agagatgggt ttcactgtgt ttcccaggct    66240
ggtctcgaac tcctgacctt gtgatccacc tgccttgggc tcccaaattg ctgggattac    66300
aggcgtgagc caccgcggcc ccctgtgcct tcttctttta ctcctggatt taatcccaac    66360
gtgaagaatc taccttacta actagagttt tagatacttt ttcaaaacca agcccacatc    66420
tgtccttttt agagtcttct ctgaccttcc ctgctcattg tggtttgttt ttattgcctg    66480
taacaatggc tgttaaactt tacattttaa attaatttat gtttgtatgt atttatttgt    66540
tgagaaaggg tctctctctg tcaccctac tagaatgcag tggcgccatc atggcttact    66600
gcttcctggg ctcaagctgt tctcccattt cagcctcccc atgcaccacc ctacctggct    66660 aattttttg tttgttttt ttagtttagt ttttgtagag acagatgtct cactgtgttg    66720
cacaggctga tcttgaactc ctgggctcac ttgatcctcc catctcagcc tcccaagtg    66780 ctgggattac aggtgtgagt caccatgccc agactttaac attttcttttt tagtatagaa    66840 taggtcagtt tttttccctc tgatgagatc ccatgctgac tcttagttaa aacaaggctt    66900
tggttggaag aagagctagt gatgtcctag ctccctactt actccacttt cccttgcctt    66960
ctggggtgtc ctgaagacat catagggtgt catgaagtac agttggagaa ccagtggtct    67020
ccatcatgta ccaaacactc atcttcacga agcagtatgt agtgtctttt ttaccggtat    67080
attttctctc tcccaatgca ttaaactttt ctggagttca gaaaacaaat ttatagaatt    67140
aaggaaatgc gtccccccca accatggtgt ctagtatata tacagtgact tacagataac    67200
aggtgttcaa catatatata ttcctttgat tgatttttga aaagtttaca tgtatatatt    67260
ttttatatac ggggtctcac tctatcactg aggttggagt gtggtgatgc agatcttggc    67320
tcaccgcaac ctcctcctcc caggctcaag tgattctccc acctcagcct cccgagtacc    67380
tgggaccaca ggtgcgcatc accatgcctg gctaattttt tatatttttg gtagagacag    67440
gattttgccg tgttgcccag gttggtttcg aactcctgag ctcaggcagt ccacctgcct    67500
tggcttccca agtgtgagcc accactgaaa tacttatatt tttaaactta atttatttat    67560
atttattata tttttatgtt tttatatttt aaaaatatt tttatactca ctagacccaa    67620
ttttatactc ctaaaccagg gaataactgt ttttttttct cttacatagg catgatacca    67680
```

```
tagacaatga ttaaaattgt aattaccatt catttcttag ttttgtggct gggacactga    67740
tgtcttcaaa tgttagtttg caaatacagt cagccctctc tatccatggg ttacacagct    67800
gtgaattcaa ccaaccatgg atccaaaata tatgggaaat acgctggggc tgtgggtcac    67860
acctgtaatt ccagcactta gggaggctga ggcagatgga tcacctgagg tcaggagttc    67920
aagaccagcc tggccaacat ggcaaaaccc tagctctact ataagtacaa aaaattagct    67980
ggccatggta gtgcacatgt gtaatcccag ctactcgaga ggttgagaca agcaatttgc    68040
ttgaacctga gaagtagagg tttccatgag ctgagattgt gtcactgcac tccagcctgc    68100
gcaacagagt gtgagaagaa aagaaaaaaa actgtctgaa aagaaaaaaa aaaattatat    68160
gggaaatcaa aagcatctat actgaacatg tacagacttt ttttcttgtc attattcctt    68220
aagcagtacc acaactattt ccgtagcatt tactttgtat taggtattat aggtaaccta    68280
gaggtttaaa gtatgcgaga gtatgcaaat actacaccac tttgtatcag ggacttaagc    68340
atccctggat tttggtatcc ctaggggta ttagaaccaa tccccatag atgctgaagg    68400 acaactgtag tgtgtgttgg aataatttat tttcaaatgg atcatttgga gaacactatt    68460
ctttaggaaa catagcctcc taagttctgt tccatacatc cctttcacct ccacggcgtt    68520
gtagcatcct gctttcatga ctgtgtcatc actcggaagg aactgcttct cttccagaat    68580
gcttttcaag atctactctg accacagcta taaactttac acttctattc tcttcttgcc    68640
cctcacagtg ttctctgttc ctctaagatc ttaaactctg tctactccta atccagcctg    68700
ctgggtgtgg ctggagaaag tcccactggg gggctgatta gttaggaatg tagggtttcc    68760
agctcttgct ggagcctcag aagagttcag cagactttt tttttttttt tttccttaaa    68820
cctatttctg cagccttgat gaccactcct tccagtccct cacctatttg ctttattcat    68880
ggcagaggct ctttcttcct gcttgtcagt acaaagaggc aggattcttc acctggatct    68940
gtggattctc aaagaatttg tggagagaat tcagggcatt gatgaccttg gatgaagaga    69000
aatttacatc tttatttaca ctaaccttca agtgaaattt agcatttttt gccatttaaa    69060
aatatgggca acaaacaact agtagtatta gcagtatta tgacttaagc acctatagaa    69120
ctcagttaat ttcatatcgc ttgatgttat gggtatctca aattattatt ttatgtatat    69180
atatttttga gatggagtct cgctctgtct cccaggctga gtgcagtggt gcagtctcag    69240
cccattgcaa cctctgcctc ctgggttcaa acgattctcc tgcctcagcc tcctgagtag    69300
ctgggattac aggcgcacac caccacgcct agctaatgtt tgtattttca gtagagaagg    69360
ggtttcacca tattggccag gctggtcacc aactcctgac ctcaagtgat ccgcctgcct    69420
tggcttccaa agtgctggga ttacaggtgt gagccaccgc acccggcctc aaattatttt    69480
tagaaacaga atcttgatat ggtatccgct ctggccttga acttgtgggc tcaggcagtc    69540
ctcccacctc agcctcctga gtagctggga ttataggcat gtgccactgc accaggcttc    69600
aaattattat gtatgttcat cacctcttta aatttataat agttattaaa cctgttactg    69660
gatcttaata tttaatgctt taattaagaa catgtatgtt actatgccaa cagattttt    69720 tagttttttga taactgcatt tcattgttac ttgttctcat ttgatttcct gtgtattta    69780 cgaatttaag tacattctga atacggtttc ataggcttcc ctaaaatatt gaaggggccc    69840
atggattaag aaaaaggcta agaatcccta atctagaggc tccccacagt cctcttttgt    69900
catcataccc ctaccccatt ctagcctgag gagcgtggct ccacctgtgc ccttggtttt    69960
gttgttccag tccatacatc ctgcacccctt aactgtgttt cttatcccca acttgttcct    70020
ttgtgttatt cttcagtatt atagtctta atataatctg tataatacat ggtgtagtag    70080
```

```
tatatgctcg tagtatacaa ttcagttaga acagatgagt attcaatgaa aagataatct   70140
cctctctaac ccccagtccc acttccctgg ggaagcctgt gttcttgtgt acaattcaga   70200
aaatgtttat acacatattt tttatttatt tattttttga gacggagtct cgctctcgcc   70260
aggttggagt gcagtggcgc aatcttggct cactacaacc tccgcctccc tagtagttca   70320
agcaattcaa ggttcaagca attcgcctgc ctcagcctcc cgagtagctg ggactatagg   70380
cgtgtaccac cacgcctacc taattttttgt attttttagta gagacagggt ttcaccatgt   70440
tggccaggat ggtctcgatc tcttgacctc atgatccacc cgcctcagcc tcccaaagtg   70500
ctgggattac agatgtgagc cactgtgccc agcctgttga tttaattta aacagagttt   70560 cgctcttgtt acccaggctg gagtgcaatg gtgcgatctc ggctcaccgc agcctctgcc   70620
tcccaggttc aagtgattct cctgcttcag cctcccgagc agctgggatt acaggcatgc   70680
accaccatgc acagctatat ttagtagaga tggggggttc tccatgttgg tcaggctggt   70740
ctcgaactcc ggacctcagg tgatccgccc gcctcggcct cccaaagtga tgggattaca   70800
ggcgtcagcc actgcacccc gcctatacac atttttttgt tttttgtttt tttgagatgg   70860
agtctcgctc tgttgtccag gctggagtgc agtggcgcga tctctgctca ctgcaagctc   70920
tgcctccctg gttcacacca ttctcctgcc tcagcctccc gagtagctgg gattacaggc   70980
gccggccact acgcccatct aacttttttgt attttagta gagatggggt ttcaccgtgt   71040
taaccaggat ggtcttgatc tcctgacctc gtgatctgcc tgactgggcc tcccaaaatg   71100
ctgagattac aggcgtgagc caccgctccc agctatacac gtattttaa tgccactcca   71160 gtctatgttg gaaccatttt acttcccctt tcttattttc ttcttgtgtt cttgaaggcc   71220
tagatcagct gttgctgata ggctgtcact gtcactttag aaagcccaga gccttttgtt   71280
ccttagaact ttgtttttaa ttgtattgta gcactcattg tattcgattc taaaagattt   71340
gcttcatttc tgtaactagt ctcttacacc caggagctcc tagttcctac aggaaatgct   71400
gggaattgta tcagtcaaat gtgaatcccc acctcgtcca gacttatgag tgcattgtag   71460
gtactcagta agtgctaaaa atgactaaat agtcccactg ataccaatct atatactgat   71520
actttatata gtatatagat tggtccacat ataacgatga cacataatga gaaactgtct   71580
taaaaagttg ttgaaagtgc cgcaggaata ggaattgatc aaaacaatat gattttttag   71640
gtttatatgg aactttgatg tttgagaaaa ggctgattta gttgagaaga aatggttagc   71700
tgaggatttt gatgacttct ctggaagcac atttgagggt ttgtgatgtt aaatctgatg   71760
ttaatgatta tttcatccag ttttatgtca tttatagtt tttatacatt taagtatatt   71820
tatttctaat gtttaacact accattttag ttatttgacc attattctgg cccttttaaaa   71880 aatgctcaga caagtttgaa tgattttttca gaggcattat tggctcagag gtaaaagagg   71940
aaagattgag aagctgaata tgtactctgt ttcctgggta tggggctggg gatacccaga   72000
agaggttcac acgttggtcg agacatttct ttatgaccac cagcaggtgg catcaccggc   72060
ccaaaatgac taagtttctg cccagaatca gaagagaagg tgttgagagc ccactgctgt   72120
gggggtagca tggaggtggg atacagggc tggaggtgat acaatttgt ttcttcctcc   72180 aacatcgcct gctagtctag aggcttttat aaattgaaaa actaattctt tatcatctca   72240
tctgatggtt tttatgtttt tccttttttc tctctatacc tgtagttcct tcagaaacag   72300
gtaacacttt tctaatagtc acgttgtatt cttgcatctt gttgttacaa tgcttttgtt   72360
tctcaccata ggggatgatg gaaaattaat attctttgac ttatgggcatt ggtaaaatct   72420
```

```
gcatgcaaat tcccacagtt gcctgtagat tagagccagt tgttttttc tcaactttgc    72480 aggaatcctg gttacaacat tgtactattt actaccaaca gtgttttttt tttttaaaat    72540
ccagacttgc tgggcatagt ggctcatgcc tgtaatctca gcgacttggg aggctgaggt    72600
gggaggattg cttgagccca gggctgcagt gattgcggca ctacactcca gcatgagtga    72660
caaagacccc atctctgaaa aacaaaaac aaaaacaaat ttttttaaa gaaacagaaa      72720 caaaaatcca aacttgtaac cactgtaaaa caaatcagaa tttacgatag tggatattat    72780
taatagtgca gaatggatac ccagatcttg cttcctttct agctaatgat gcaatgttgg    72840
cctgaaatgc attacttata gccagggatt ttctcagcat cctgatgata tagcctcatt    72900
tcgtgctaac tctccacttc tgcacatctt cccctaagtc ctttactcat ctttagaaag    72960
agctactttt ggtgaaattt taaaaccaag gaatatcatt cttatagaa tcacacttct     73020 gtgttttccc cttccccatt tctgtctcga aagcgacaga ctgctacata acctgtgaat    73080 acttttttt aaaaaaagtt tggtattgta aacagaagat ttaagattaa aatgtagcat     73140
tgagaaaaat agatttatta ataatgccct cttaacacaa cctaaattct ggtcagtgga    73200
ataaagcctg ggtcctaaag ttttagacgc ttgcttgctt ttccacactg gctcttactt    73260
ggggatcctt ttagaaattt gtttagaata atactgtaaa aacatattta agctactttg    73320
tgtgtacatt tgggatcttt tggttgaag acggcttgac tcaagacttt ctaaatattt      73380
tcacacacac acacataccc tgtagtgaga aaaaaatccg tttatatggt tctataaaaa    73440
tctctagctg cttcgagctt taatttcttg aatcaaaaga gtattgtttt taatactgag    73500
cttctatcta aataaatgct ttattttact aaatgtgtgc ttttcaaaaa ctagtatgat    73560
taagacatta acaggatctt agacgtaaag gaacagtcct gttgcttctt ccagaagata    73620
atatgactcg tttggaattt tcctatagtg tagttttttg tctagtgttg tgagaattaa    73680
agggatttca ggatcttaag gtaggttatt atttgatgtt ttcttggaac attttacatt    73740
cttgaaaata cacatggcta aattaatttt tgccagcaat ccacataact ttaagataat    73800
gtagagaaga acgtgattca ggttagtatc aaataaggtc agatttctag tgccatcagt    73860
agctttcagc aaagatgagg tgttggtaag atagcattag tctcttagaa tctcttagag    73920
agattttcca aaattcagcc atttctagtg aatgctccat tccaccccca gctgagtcct    73980
gctgctctgg ggaactccct cagcacactc ttggctctta gaattgctag caatgggagt    74040
agtgctgctg gtggagctgg cagctaagcc cagaggtgga ttaatgcttt tattccctga    74100
tgtacaggta cacacactca tacctaccca cacctagttt gggataagaa gaggttagaa    74160
ttagctaggc ttgaagttcc atgcttaaat ttgctggctc agatttctta ttttggcatc    74220
actttgccca ttagggagac aatgacagtt atagaagcat tgccaaataa aaaatccatc    74280
tggaataacc tcttttgtag gagtattgtg tgtttagttg ttgattcgtc ccttcctcct    74340
cttagtggca acttacagta ctgggaagga acagtggctg ggagcttata ttcctcagca    74400
gagccagatc agcagaagta ttactcctta gttcgtagta ggtggtaccc tatgggtcca    74460
gtcatttaaa tgcaagcctg tatctacaga gcgtttccta gtgccatcat tgcccagtgg    74520
gcctttattt agctgagtct aactcccaac tagagaaaat ttcctgtgcc agacagcagt    74580
atggtcagct aacatgtgga tgctacattt gctttcataa gtcagtactc ttcaataaca    74640
ttagtagaag agaagaggac acaaagtgag agtgtgttaa taggaagtcc aggtatgcct    74700
gctacctgaa ctttctgaga caggtaatac tgtagggcct gaactttgta gcagagtggt    74760
tatatatgaa gaagtgggtt ctgggagggg ttaaaccact tagaatggct tcatttacta    74820
```

```
atggcaagag tttgctggga tattgaccac tgtacataga catgaatatg gaaagttaaa    74880
aacaaaatcc acatatattt ggctgcaagt actccgaagg tatatctaat tagtgcatcc    74940
attaaacaaa agagatattt taggccgggc atggttgctc acacctgtaa tcccagcact    75000 tgggaggcc aaggtgggtg gatcacctga ggtcaggagt tcgagaccag cctggccaac    75060
atggtgaaac cctgtctctg ctaaaaatac aaacattagc tgggcgtgtt ggtgggcgcc    75120
tgtaatctta gctacttggg aggctgaggc aggagattcc cttgaacctg gaaggtggat    75180
gttgcaggga gccgagatgg tgtcactgca ctccggtctg ggtgaaagag caagctccat    75240
ctcaaaaaag aaaaaaaaaa aaagagatat ttttgatgga ttgatagaaa ttttctttttt    75300 cttttttttt ttgagacagg gtctcactct gtcgccaggc tggagcacag tggcgtgatc    75360
tccattcatt gcaacctcca cctcccgggt tcaaacgatt ctccttcctc agcctcccga    75420
gtagctggga ctacaggcat gtgccaccat gcccaactaa ttttgtatt tttagtagag     75480 agagggtttc accatgttgg ccaggatggt ctcgatctct taacctcatg atccacctgc    75540
ctgggcctcc caaagtgctg gtattacagg catgagccac cacatctggc cagaaatttt    75600
cttggtcact tctgagacat gcagagtaat tacctgtaat ataatttaat gaattatgtc    75660
aatatattaa aatatgcttc atgtgggctg ggcatggtgg ctcatgcctg taatcccagc    75720
actttgggag gccaaggtgg gggtatcact aggtcaggag atcaagacca gcctggctaa    75780
cacggtgaaa ccccgtctac taaaaataca aaaaattatc cgggcgtggt ggtacacacc    75840
tgtagtccca gctactcggg agactgaggc aggagaatcg cttgaacccg ggaggcagag    75900
gttgcagtga gccgagatca cgccactgca ttccagcctg gcaacagaa cgagactcta    75960 tctcaaaaaa aaaaaaaaaa tgcttcgtgt ggcttaaaat tatatgaaaa gaaaatacct    76020
ttactgatag tcatctgtga ttccatttgc taaattaaac gtgaaagcat acttttactg    76080
aatactatat attccgtatc agtttagata gcagtttatc ttcacataca taagttttaa    76140
gtttaccttt attatagtgc attggtcttt tgttttcatc aacctaaatt atgttcaata    76200 aatgttctg ttagatttta agttaaacaa ttatgtgaaa ttcattttc gtaattgttt      76260 tttaacatat gtctttgttg gtaattcacg tgtgtgagtg taactgattg ccagattata    76320
taaactttca accaaaacca ttcttttgcag atgcttttac tgactctgct atcagtgcta    76380
aagtgaatgg cgaacacaaa gagaaggacc tggagccctg ggatgcaggt gaactcacag    76440
ccaatgagga acttgaggct ttggaaaatg acgtagtaag taacatcttt gtaattattg    76500
ctagactctg gtcagtatga catcctgtca cttggttgta atttaaatgt gcttttgttg    76560
ttgttgttat tgtagtgagt gtatttagag cagcaggttt ttgtgtataac tagagacttt    76620 ctcccaagca atatataaag aaaaatgttt gtcattttac ttgtagggt taagcaggag     76680 tactgtctgt tcttgtggat gctcatgaat tacttctttg tgattaaaat aaataataag    76740
aagtagctta aattaaaatt agaaccatg ggaaatgccg gtgtgttttg ctttaacacc     76800
cagccaaata aggtagccta aggaaagtgg tgtcttaatt gttgacttca cctagagaag    76860
aggttgaagt aggacatttt aagcctcttg tctgaagaaa aggttgtcat taagataaat    76920
aattaggtta cattggaatt aaagcattac ataaatttct tggtcttaaa tttggattat    76980
tctccacaaa attctttat ttctaaaacg cctcttgtca catactagtt ttgtttctct      77040
ctttaatgca ttatctgtac ttgaagtgct tagctgggta tgctggcaca tgcctgcagt    77100
cccagctact tgggaggctg aagcaggagg atcacttgag cccaggagtt ggagtccagc    77160
```

```
ctgaatgaca taaggagacc ccttctctaa gaaataaaaa taaaaacaaa tacttaataa    77220
agactctgtc tttaggatag agagcataga gatataaagc aaagtgtctt gccaaaaatg    77280
agtgttatgg taccaatatt tgagtagaat gaagaatctt ccattgagta gaaagagaat    77340
ttgtaacata tctgtgtttg atgtttaagg cataacagct taataatgac actcttcctc    77400
agacaggaag cctgaaatgt cctactttga cctaaagtct agtaataaaa ctggacatac    77460
acaggcaaca tgtcattaat tctcaaactt taacaaatca tatataaccct aatataatgg    77520 ttctcaagtc tgtacatcac gtcacctgta tgaaaatat gaggaaacag agacttcttt    77580
tacactattg gtgaggtgga taaattgata gagtcttcct ggagagaatc tggcaatgct    77640
aatcaaaatt taaaatgcac atacactttg ttccagcagt tctatctcta gtaatttatt    77700
tttgccctca tatatccata agacatgcaa ataattatat gtgaagattt ttttttttc    77760 tttttctgca gagacagggt tttaccatgt tgcccagggt gatctggaac tcctgagctc    77820
aggtaatcca cccacctcag cctcccaaag tgctgggatt acaggtgtga gccatcatgc    77880
ctgaccagga tttttttttt tttcagcatt atttcttttg ttgttgttgc tgttgttttg    77940
agagatggag tctcactctg tcacccagac tggagtgcag tggtgcgatc tcggctccct    78000
gtaacctcca cctcctgggt tcaagtgatt ctactgcctc agctttccaa gcagctggga    78060
ctataggcgt gcgccaccac acccagctaa tttttgtatt tttagtagag acggggtttc    78120
accatatgtt ggccaggctg gtcttgaact cctgacctca ggtgatctgc ccacctcggc    78180
ctcccaaagt gctgagatta taggcgtgaa ccaccatgcc tggccatagc attatttcta    78240
atagtgaaaa attggaaaca tgctaagtgt ctatcaatat agcatgagtt agatttatga    78300
tgtcaccatt caattgaaac actacatatc tcccaaaaag aatggtgttc caatatggaa    78360
agatatctaa gatttattaa gagaaaaagc acattgcaga acactgggat cctatttgct    78420 ttttttttc tttttttgag acagagtctt gctctgtcac actgcaacct ccgcctcccg    78480
ggttcaagcg attctcctgc ctcagcctcc tgagtagctg ccaccatgcc cagctaattt    78540
ttgtgttttt agtagagaag gggtttcacc atgtttgtca ggctggtctt gaactcctga    78600
actcgtgatc cacctgcctc agcctcccaa agtgctgcga ttactggcat gagccaccgc    78660
acctggccat gaaattttt ttttttttta aagagctgtt catattctta ttgcctagaa    78720
gatgtctgaa attacaccca agaaactctt tttgagacgg agtcttgctc tgttgtccag    78780
gctggagtgc aatggcgtga tcttggctca ctgaaaccct tgccttccag gttcaagcga    78840
ttctcctgct tcagccttct gagtagctgg gactacaagc gcccgccacc acatctggct    78900
aattttttgt atttttagta gagacagggt ttcaacatgt tggccaggct ggtcccgaac    78960
tcctaatctc aggtgatcca cccaccttgg cctctcaaag tgctgggatt acaggcatga    79020
gccactgcgc ccggctgaaa ctctttttt ttctttaag atggagtctc gctctgtcgc    79080
ccagacttga gtgcagtggt gtgatctcag ctcactgcaa gctctgcctc ccgggttcac    79140
accattctcc tgccctagcc tcccaagtag ctgggactac aggctcccgc caccacacct    79200
ggctaatttt ttgtattttt agtagagaca gggtttcacc atgttagcca gcatggtctc    79260
aatctcctga cttcgtgatc ctcctgcctc ggcctcccaa agtgctggga taccaggcat    79320
gagccaccgt gcccggccag aactcttaat agtagttatt tatgcacgct gggattggaa    79380
gacatttact ttttactgga tgtctttccg tattgtgtgc tttttttttt tttttttat    79440 gtagggcata cattacttaa gtaatttaa agcctccata agtaagtgtg atttcctgcc    79500
catgtgtttg gcaaaaggaa ttgcattggt ggtagactta cattatagtc ttacctggag    79560
```

```
tagcacagga ggacccaagg ttaataggtg aacttcgagg caagccttag cattgaggtt   79620
gccatcagca ttgcttggtt gatgtgttca ttcttctggg atggattaca acctttactg   79680
gactttatac ttttcaccag taaggcttta aaaaggagt tgaaacatta gagaataatt    79740
atccaggcag taatattcac tggtaaatag tcttccagcc tgtggcccaa ttggttgatt   79800
cttttacgtt aaagaatgca gcctcagctg ctctgcctat ggagtaggat tcttttattt   79860
actttcttaa taaacttgct tgcccctggc tccccccac caaaaaaga aggcagcctc     79920 cctttgcga atggtaattt cctatagttt cctcgtagaa ttgtggagtt acctatgctg   79980
aggttatagg ttagggtatt gagatccaga gttgccactt ctgaggtgtc acaactgcta   80040
atggtaaaac catttctaaa gcccagttct tgtgactttg tccagtgatt gcctgttcac   80100
cgtttcatgc tgccttccca tttgagcatt cccaggagga aggggaggtt gccagggacc   80160
tagtaccata gtccgacctt ggaatcgttg aatatgaggg aaagcgttgg cttctcccct   80220
ctttctccca aacattggaa gtattttgg ctgttaaaaa gcaccccttg ttccatgtgg    80280
aatcccttgt ttaaaagaag taaaatatgt acctcctgtc ctccacagac ctgaggacca   80340
gtgtgatctc aagaaggtta caggtaaatg tagatgtctc taactgaaag gtggcttta    80400 caggttagag aaaagagaga accctgatct gaaggctatt ttatgaagta attaaaatgt   80460
tctaaacttt aaaaataact gctcaaataa ttgtgttgta tagttactta tcaactggag   80520
gggctgataa gtattttct aaaacatttt taaggaaatt ttttcctatt ttctaatttg    80580
ctaattttgc tcaagtagtt tgttagatat tgttaatata gatgttggtt ataactgaat   80640
gaaagggaac aactactttg acattttgaa aaacaagctt cattttcttc tagtctaatg   80700
gatgggatcc caatgatatg tttcgatata atgaagaaaa ttatggtgta gtgtctacgt   80760
atgatagcag tttatcttcg tatacgtaag tttgaaaagt ttgttttat tttagtgcat    80820 ttgtctttga ttttcatcag cttaatttat gatgaataaa tgtttgttag tttttaagtt   80880
aaacaattac atgaaataat ttttctctta ttaccaactg tgataaattt ccattaaaaa   80940
aagggaataa atgtagtttg cctatacct gttttatgc tctaaacaaa ttttggtttt     81000 gtctttttt ttcttttgag agggaatctc gctgtgtctc caggctggag tgcagtggtg    81060
caatctcggc tcactgcaac ctctgcatcc cgggttcaag cgattctcct gcctcagcct   81120
cccgagtagc tgggactata ggcgcgtgct accatgccca tctaatttct gtattttag    81180 tagagacggg gtttcaccat gttggccagg atagtctcga tctcttcacc tcgtgatcca   81240
cctgcctcgg cctcccaaag tgctgggatt acaggtgtga gccactgtgc ctggccggtt   81300
ttgtcttcta agttgttaaa aaatatctaa atttgcaagg gcagagatta tggtgaacag   81360
tttaaccagt ttttgaaata tgttcctctg gagaaaaggt aacagaaaaa aagttgaaa    81420 ttttgattta taaatacaca gatcactata acttttagtt ttagttttag ttttagtttc   81480 tgttttacc agtattctaa actctaaact ttccttagtag ttgattatga cagatacata   81540
aactgtggct ttaaaggact catttgtctt ttcttttcct catgtttcag agtgccctta   81600
gaaagagata actcagaaga attttttaaaa cgggaagcaa gggcaaacca gttagcagaa   81660
gaaattgagt caagtgccca gtacaaagct cgagtggccc tggaaaatga tgataggagt   81720
gaggaagaaa aatacacagc agttcagaga aattccagtg aacgtgaggg gcacagcata   81780
aacactaggt atttaaagga aatcatgatg cagtattttg gatacacaac tcaaggtctg   81840
tgtgagacgg tgtattgtta ttatatttcc tcttccttta atatagctta ggtagagaat   81900
```

```
gcaagtagaa ttggtttaag atctgttaga gaaaaggtta tggtgatctt ggaaaatatg   81960
cttttgagag taagctctgt ggagccaagt gttggtatat cacggtgagc aatccaagat   82020
cttgaagagc ttgttaaaat agttatctgg tgggggacac gtgtaacaat cacagcagta   82080
caatatgatt tgcttggtta aaggcatgtt caaagtacta ggaacataca gaatgaggag   82140
gagctagcat aacctgtaga gtcagagaaa acctcattga ggaggtgaca ttttgtgata   82200
agataatagg gtcttttgaca cttagagaag agttgggaga agagtttatc acctgatgaa   82260
aagccatgta caagcatggc tatgagaaaa tttggccagc tcaggagagg gctggttgtt   82320
gcatgtgtct ggaacacagg atctgtgtca ggtgcagcag tggcagttga tagtaggaac   82380
tgaggtcatt aaaggacttg gcatgtcatg ctaaagagca ccctgttgga aggagatggg   82440
gtgaataaac cctggggcat tgaggactgg ctgagacaca gagaacagtt agtgcactga   82500
aatagttcaa ctgtgagaat ttggtaacca cctagttaag ggatgagcct gaggtttatt   82560
tgataactaa gtgacttaat ggatgtactg gtaagagaga gaggaaacat ggagcaagtt   82620 tgagggaaa aacagtgact ccgtttgtgc agctaattgc atatgtgggc ttgtgggtct   82680
ttcatttatt cataaacgtg ttgagaaata cctgctacct atctagtaaa gtaagagatg   82740
catcctctct taaaggcagt cagcttagag tctggtgatt tgaattgaca tgtccactga   82800
tagatgttga cactgtgaga ctggcggttc agtttgaggt ttcatcagca ttgccgatat   82860
tggagccatg aaaaaccaaa gaacagccag tgagagaaga gatctcagag aaaataaaat   82920
tgagaaagtg aaggacaaaa atgttgtga agatagacca agattgatgg aatcagccat   82980
agagaggtca gtgggatga aatgagcac gcatctgtta aactttgtgc ttaggagcag   83040
aatctaaggg aagggacagt ccagaggtta gaactcaggg taagatggaa gaacagggggc   83100 atctgggagt gaggcagttt ggtttagtgt agaacctttt tgtaacaagc attcccttct   83160
gtctagatga cttttagata tgtttcattg gcttggtacc ttttagaata aatgattta   83220 gaggatctct cattttcagg gaaaataaat atattcctcc tggacaaaga aatagagaag   83280
tcatatcctg gggaagtggg agacagaatt caccgcgtat gggccagcct ggatcgggct   83340
ccatgccatc aagatccact tctcacactt cagatttcaa cccgaattct ggttcagacc   83400
aaagagtagt taatggaggc aagtatttg accagacttg tcaatatcat tgataaaata   83460
gttttctaaa tacttaaaat acttaaaata gtttacataa ctgatatgaa tgtgcacttt   83520
aatgatttgg tgagtagctt tcacttcagc attacttaaa attggctttt gtggatatta   83580
aattagtaaa acattgtata tgtcattgac atatatatta tttagcatga tgaaatattc   83640
atgatgtact aagataaagt gctacattta acccaagaca atcacttggc caaaaacact   83700
tcacatataa agaaattgga aactttgggt aggttctcaa ttttaaaaac actggataat   83760
aaaatttttt agacataatt tatatggaaa attctaacct atgtgcaaca ctgtggttaa   83820
tatagatcaa ttttcattat ttgttttctat attatgctta cttcaagaaa ggatctgagg   83880
taacttataa tacaagacat gatcaagagt catgtgaaga aagtgactag agaaatttgc   83940
ttaaaaaaca acaaaaacaa cccttagtct aagggtggat gttacagttt agcaacttaa   84000 gtaaagaaa cctgaatctt tagtaggaag acatttttta ctctacctct aaatctaggt   84060
tgaatatatc ttgtaggttg tggatctttt ccataaatca gggatactga caacagttc   84120 tatggatggt atgaaatag taatagcaat agtatgttac taactttgtg ggaaaagagt   84180
ggacattcaa ttttagctat ttaaatttgg aaagttagat gaaaatagag aacactaagt   84240
ttccaatttc atttgttttc attgagtctt ttctccagaa ttcctctcca aatggacact   84300
```

```
cttgagtatt ttcagtactt aatattgggg gtgaaatttc tttgctcact gaggaaagat    84360
tttagttgtt tataaacaga atttttaaagt taaaaaacct gaaggggggct gagaaatata    84420 tgatacttaa gtgtgtggaa ccctatggag aggagacctg gactgtttga taagattaag    84480
gtaagtgata tgtaatgtta aatactagct gtatctttac ctaggcatat ccatcagtat    84540
aaatttattt ggtgatgact gctttgtagt tgcagtattt attaagcagt cgcttagata    84600
agtgtttaac tgtataaatt atttagaagg tctcccttt tctagtttaa tgaggtcaag    84660 acttttttt tgaaatagca atgaatatta tcatttgata ctcacaggag tcacaaactc    84720
tagaagagta atgttttatt tctacttaaa tgggacttgc ttaataagat tccaaactga    84780
gttctgggtt caagtgtaaa cctgatgaaa atcatagata attgtaagga accagcattt    84840
ctaattggat ataatagcta ctgcttattt tcgttatgcc tcagagttaa aactaataca    84900
gtaaataatc ttactcctga gtaggaatta ttgtgattta ttatgtgaaa ttatctagtg    84960
tatgttatat tcctttaaac aaccagttac tgagaaacag ttatagaagc aggattaata    85020
ggcaaagtct taactgtctt cttcaatagt gtgtatagat cctaattaac cctttgggaa    85080
cgtgtattca tttaaacaga cttaatctta aggaggttaa agtaaaatgt gaatttatgt    85140
cagttaagtt atgctaaaac ttatcacaaa tcaaatgact gtcctcaaag ggttaaaatg    85200
tacaagaaat catttttgtc atttttacttt ttttctgttt acttttttcc ctcatttttt    85260
tctttagttt ttatactttc cttcatatca tttgttctgt caggtgttcc ctggccatcg    85320
ccttgcccat ctccttcctc tcgcccacct tctcgctacc agtcaggtcc caactctctt    85380
ccacctcggg cagccacccc tacacggccg ccctccaggc cccctcgcg gccatccaga    85440 cccccgtctc accctctgc tcatggttct ccagctcctg tctctactat gcctaaacgc    85500
atgtcttcag aaggtacaat accacaattt gttcatgttt ttgtttgtct ttgtttaact    85560
cctatgtgag tttataatta caaaatagtt tcctcttcat tatttaataa cctataatttt    85620 ctgtgtttta actttagttt attaaaacta tttctattaa ccttttgttc attagagaga    85680
aatttgataa atgtgtgaag ctataaactc tcttgaattg ttgttaaaaa gggggtttat    85740
ctctgcctga taattatgct tctttacagc cccagaaggg tctgcccac agccttcccc    85800 ctccttattt gcactgtata cagtagttaa acaaatgaac tttcttcagc cagtcttgaa    85860
cttaggttca ttttacagct cttttggccaa ggtcctagtg aaccttccta ttggccataa    85920
gcagggatgg tgttttctgg gtcttttttg agagcgacag cccatgtagc tgactttgcg    85980
tgtctgccct tagattaaag tagttgattt ttagaatgcc agaagaattc taaatttaac    86040
tgagtaattt ttttaaagtt agctttgcaa tcttacatag tgaaaggctg ctttaatctg    86100
gaagaagtcc ttgatctgag ataaaattga taaaaacgac atatgaattt gaatatttag    86160
ctatttcttt cctcgtcaaa aataagaata aaatcttgta attcttattc agtatttggc    86220
gctaaatcca tcattgccac atatcaaata cagggatatg ttgtagaaag gtaacattct    86280
aatttaaatg ccacccatat attaaaaacc tgttttctga atcataatgt cctttttgata    86340 ctagttctga atatttgtgt taaaatttta atctgatttg ttcattaaaa ttagttaata    86400
ttgcttatgt tgggactaat aaagttttcc gcacaaaatg tgtttctcct gcttccctgg    86460
agaaaactgt attggctact tttaaataaa ttgttaccat ctaagcaggc aggtcatatg    86520
actttgactg aagcatctaa ccttgaagag caagttccac tgattttcaa ggtgacttct    86580
ttgctcaaaa gggccttaat agtggtcact aaaatgcaaaa ttctgttgat attttttcttg    86640
```

```
tagtccatca tttgagtaag cgatgtttat ttaatgagaa tatattaaat aaaacatgat    86700
cattaatgac tgtgaacatc tttattacat taagatttaa ggactgctca tgtattaact    86760
tcacacagaa atatactttc tgtgtcattc agagatgttg aatatttcca tttgaaaatt    86820
atagtgtata acattagcat tcttctaaag atcatgttcg tgtttaaatt cctgttggaa    86880
gccaggcatg gtggctaacg cctgtaatct cagcactttg ggaggctgag gcaggtggat    86940
cacttgaggt caggagtttg agaccagcct ggccaacatg gtgaaacctc gtctctacta    87000 aaaatacccca gctacttggg aggctgaggc aggagaatca cttgaacctg ggaggcagag    87060
gttgcagtga gttgagatcg taccactgca ctccagcctg ggcgacagag acagactctg    87120
tcttataaaa ataaaaataa aataataatt ctattggcaa catatattaa tttgaagttc    87180
taaagagttt ggcagccggg tgagagagtg aggagatttg ctttgacat tagggaagtt    87240 ttcgcttggt gttaacacca gtaggcttct ctgatgaggg ccattctgtc cactctttta    87300
cctgatagat tggtctaatg cacagtagac tgatttagaa agagtagtca ctagtggcat    87360
ggcagaatca ataatgtaga attttgacaa ttcatatagt gctgatttct cccccaaatg    87420
tcagttattt tggtcatcta ttaatagact aatacaagtc atccctttaa tagaattttc    87480
agctcacagc ctgctaagcc taagaaactg cttacaggtt actgcttact gttttaagcc    87540
gagttttaaa attgatgatc atgatagaag agataaataa actaaaattt tagagaaatt    87600
taagaagggt atgtacatat gttttagtgg tatcggggtg tatagggatt aatagtcttc    87660
tgtttaaatt tttttttttct aattttagaa gtaatgtaga aaattcgggt cagggaaagg    87720
taaaatatat ggaaagttaa aaatatttta tcatgtagtc ataatttcta gtaacatatt    87780
tctttacaaa taagacatag ttgaaacaga ttgctacagt tcttttaaga gttgacatct    87840
tattgttgat ttcttaccac caacttcatc cctcccttc tttaaaaata aagggaaata    87900
ataaaattta tttataaaac tttgtggcat tccacaaaat aattctgaaa gaattagtat    87960
ggccaaaaaa atatgtatgg tgttttttt ttttctattt ttaaccaagg aaaaactgta    88020
gagtgagtga gtgtgtgtgc atgtgtgtgt gaatgggtgt atttagcaga aaagtagtac    88080
tgatgaatat catggaattt atgtgatgtt cactgtttct tccttagggc ctccaaggat    88140
gtccccaaag gcccagcgac atcctcgaaa tcacagagtt tctgctggga ggggttccat    88200
atccagtggc ctagaatttg tatcccacaa cccacccagt gaagcagcta ctcctccagt    88260
agcaaggacc agtccctcgg ggggaacgtg gtcatcagtg gtcagtgggg gtaggtaaca    88320
cttgggcata atgatggtac tcattttgtc attacactag atataaagag ggctgagcta    88380
caactctgtt tgaggaagtg taagtatgta tatgttaaaa atagtagaat caccaggaat    88440
tgggaaaccc atattttttat tctgggctct accacttatt catcatatat taaagcaagt    88500
cagacactca ttctgaagtt gagatttcgc agtgagtaaa gtgttaataa ttcttgccta    88560
gtctacatta tgggattgtg atgagattcc tataaggttc ataaatacag atatattgta    88620
aaactataaa gtttttgtaaa gtacctctct aatatgaggc aaaacagta tgtaacacta    88680 tttggaggga ccgtatttcc ttatcttttt agcagctttg tttatcagta cattctataa    88740
acatttattt ttggcttaca ttgtagtgtg tttctatagc atctgtatat ggcactaatt    88800
cccaactata tttccataat aaggaatatc aaatacaaat aaagggtcca agttttattt    88860
gtgattagca taaggaatat gctgacagca gctataaaag tataaaaatt aggctgggtg    88920
tggtggctca cgcctgtaat cccagcactt tgggaggctg aggtgggcgg atcacaaggt    88980
caggagatcg agaccatcct ggctaacacg gtgaaacccc gtccctacta aaagtacaaa    89040
```

```
aaaaattagc cgggcatggt ggcgggtgcc tgtagtccca gctacttggg aggctgaggc   89100
aggagaatgg catgaactcg ggaagcggag cttgcagtta gctgagatca cgccattgca   89160
ctccagcatg ggcaacagag caagactctg tctcaaaaaa aaaaaaaaaa aaaaagttta   89220
aaaactagac gttgacatga ttttacaata aggctgactg cttttgctac tttgccaatc   89280
agtccttagt gctttgttcc cataactgtg gtaagcaaga gcttacaaag aatacttaaa   89340
acaaacaaac aaacaaacaa aaaaacact ttttctcttt taatcagtcc agagaacctt   89400
taaaagaaac aagatcggcc agttgctgtg gctcatgcct gtaatcccag cactttggga   89460
ggctgaggtg ggtggatcac ttgaggtcag gagttcaaga ctggcctgac caacatgatg   89520 aaacccatc tctactaaaa atacaaaatt agctgagtgt ggtggctatt gagaggctg   89580 aggcaggaga atcatttgaa cccaggaggt gaaggttgca gtgagccaag atcacaccat   89640
tgcactccag tctgggtgac aagagcgaaa ctctatctca aaaaaagaa aaagaaaca   89700 agatcttcaa gcttaaggaa acaaaaacaa aactcagctg tgttaaatct gtttttagtt   89760
gctatacatt tctgctcagc ttcatgtgat gcacattcat gtaattgtat cctaaattcc   89820
tttgtacttt ttattttctt ccttggtctt caattatctt aagactacca agaaaacaaa   89880
aattttaaaa atcttcttca gccggtcagg cgcagtggct cacggctgta atcccagcac   89940
ttggggaggc tgaggcgggt ggatcacgag gtcaggagtt caacaccagc ctggccaaca   90000
tggtgaaacg tcgtctctac taaaaataca aaaattagct gggcattgtg gcgcgttctt   90060
gtaatcccag ctgctcagga ggctgaggca ggagaattgc ttgaaccagg acccgggagg   90120
tgtaggttgc ggtgagcgga gatcgcgcca ctgcactcca gcctgggcta tagagtgaga   90180
ctccatttca aaaaaaaaa aaaaaatctg cttcagctat tctgttaatc ttttgacatt   90240
acttagatgg tctggaaata aattttgaga ataacatgat tagaagtgag agagtataag   90300
catagttttg gagatacact cagaatagca ttatagattt tctctttta ctaattggaa   90360 aaatggcagt tgttgaataa tagttttctt ccgtgaccct tgtgacttaa aaaaaaaaa   90420 acactgaaat gaaataatcg aaccattttc tctaaaccctt tgaatctgag ctctgcagtt   90480
aggtttataa tggtatatga aacctattag atatatactt ggaagtcata tgggatacaa   90540
accctgcttt tattatcttc ccctttgac taacttgggt ctcaagtttc cttaattact   90600
gcacagtgga ccttgatgtt gctataaaga atgtgtaggg ctgggcatgg tggctcatgc   90660
ctgtaatccc agcactttgg gaggccaagg taggcagatc acctgaggtc aggagtttga   90720
gaccagcctg gccagcatgg tgaaacccccg tctctactaa aaatacaaaa aaattagctg   90780
gttgtggtgg cgagtgcctt taatcccagc tactccagag gctgaggcag gagaatcact   90840
tgatacattt agttaggaga gaaaatcata cttatgttag taattgctgc tgttcttcat   90900
atacttgtgg tttttgattgc cagcaaattc ctaacatttt ggaaaagaaa acagtaatgg   90960
gataaagggt aagggctaga gaggacagtt ttatttacct agatcttcag agaagcctga   91020
agcctctttt aggaagtaac atttgaactg agaatgtaat aaatacattt tccctttctt   91080
ctagttccaa gattatcccc taaaactcat agcccaggt ctcccagaca gaacagtatt   91140
ggaaataccc ccagtgggcc agttcttgct tctccccaag ctggtattat tccaactgaa   91200
gctgttgcca tgcctattcc agctgcatct cctacgcctg ctagtcctgc atcgaacaga   91260
gctgttaccc cttctagtga gggtatgtaa caaagggctt ctggatccat aatctcagct   91320
gtgaaattga atgttagagg gtgatattat atgaaaaaaat tctaggttat ttttattcat   91380
```

```
agacaagtat ttttagtgca catttaaaag tttatgtaaa ttttgatgtt gtttaatact    91440
actaatttaa tatagtgtct gtgttacaaa ggttaacatt cctgggtgtc aaatacctac    91500
ataaataaaa ttattggtgt ttcatatgac atctgcaaag gaaaaaaagc ctctgtttaa    91560
atgaaagcat tattttccaa aaacatagga aatcaaaatt attgttcagt gttttcttgt    91620
tttgcttttc taacttatct gaattttttt taaaaaattg ttttctagct aaagattcca    91680
ggcttcaaga tcagaggcag aactctcctg cagggaataa agaaaatatt aaacccaatg    91740
aaacatcacc tagcttctca aaagctgaaa acaaaggtta gagtttaaag agtcattaag    91800
cttaactgta ggaataggaa gaagtatgtc taatttcatg cccatacaga atattttgt     91860 tcaacatttc ttcttactat tgtgatagat aaatgtattg cttgacaaat tccaaaatcc    91920
aaatttaata tttgaaatta ttttctgatc ttatatctta ttctaatttc tatcatctca    91980
tactaaaaag aatgtgatgt taaagtttaa aaataaacct gtgtcttaac agttcttaat    92040
tttacaggta tatcaccagt tgtttctgaa catagaaaac agattgatga tttaagaaa     92100 tttaagaatg attttagggt aagtattgta ctaactgatg aatttgagtt ttagaaaata    92160
agcattacta aagatttatc tatttataaa aatgcgttat gtatacagtc agaaacatca    92220
aaccatatat gtagaaagca gaacattttt aaagtggtct ttgcctatcc tttaagtggg    92280
ataactaaaa tcatgagatt tggtaacaac aatatgtagg tatcaaatga gagtatagcc    92340
ctgacatttg aaaccaccat agcacagctt actatttgat ggtcatttgt actttgttca    92400
gtgaagctag atattagtag agcaaggcca agtcattaat aatctagtgt ggcaaatgga    92460
agatgtactg gactctggtg ttctgaggta gttggagatt tatactttgt acacaaatat    92520
attgtggtca aaatctttct gtaacattat ttctctgtct tagcacaggc tttacttaac    92580
atctctcctt gattgtcatt tcattctttt gcatgttatt tactataggt atcgaggtag    92640
attttgagac caaccaataa atcttcttga aacttagctt cttagaaagg aaaatctaaa    92700
taccagcctt ttaaaaaaag tagctgaatt aaaggatgag tgaaccaaag gcaaaggtag    92760
cctttcctca gcctgtgttt tagctttcta aatgttaaca atagcttcat tcttgactta    92820
ttggtaacat tcaaaatact acttattatt tcatacttta gcacatgtat ctattcagct    92880
ttaatgctat taacagttgt taacctaagt tttcatttgt tggcgggcac ggtggctcac    92940
acctgtaatc ctagcacttt gggaggccga ggtgggcaga tcacctaagg tcaggagttc    93000
gagaccagcc tggtcaacat ggtgaaaccc tgtcttgacc aaaaatagaa aaattagcta    93060
ggcatggtgg cgcacacttg taatcccagc tacttggcag gctgaggcag gataatcgct    93120
tgaacccagg agacagaggt tgcagtgagc cgagatcaca ccactccact ccatcctggg    93180
cgacagagca agactgcatc tcaaaaaaaa aaaaaaaaa aaaagtttt tcaatttgtt     93240 aaacaatagt taacacatac aaatgataca aagaatattg aatatgatca tgtgcccact    93300
acccagctta gtaaataaag cattctaaca cagttaaact cctcttatgt atctgcccct    93360
cctcagctgc ttcccctgt ttccttccaa aaggaagggt ttcttttctg tgcagttctt     93420
tatatttata ctgcatatga atatatctgt gagcaataga tgatattttg cataatctta    93480
aatttgctat aaagtctttt tttttttttt aattgatcat tcttgggtgt ttctcgcaga    93540
gggggatttg gcagggtcat aggacaatag tggagggaag gtcagcagat aaaaagtgaa    93600
caaaggtctc tggttttcct aggcagagga ccctgcggcc ttccgcagtg tttgtgtccc    93660
tgggtacttg agattaggga gtggtgatga ctccttaacga gcatgctgcc ttcaagcatc    93720
tgtttaacaa agcacatctt gcaccgccct taatccattt aaccctgagt gacacagcac    93780
```

```
atgtttcaga gagcacaggg ttggggtaa ggtcatagat caacaggatc ccaaggcaga    93840
agaatctttc ttagtacaga acaaaatgaa aagtctacca tgtctacttc tttctccaca    93900
gacgcagcaa ccatccgatt tctcaatctt ttccccacct ttcccccttt tctattccac    93960
aaagccgcca ttgtcatcat ggcccgttct caataagctg ttgggtacac ctcccagacg    94020
gggtggtggc cgggcagagg ggctcctcac ttcccagaag gggcggccgg gcagaggtgc    94080
cccccacctc ccgacggggg cggctggctg ggcgggggct gacccccccac ctccctcccg    94140
gatgggcgg ctggccgggc gggggctgac ccccacctcc ctcccggacg ggttggctgc     94200
cgggtggaga tgctcctcac ttcccagacg gggtggctgc caggcggagg ggcttctcac    94260
ttctcagacg gggcggctgc cgggcagagg ggctcctcac ttctcagacg gggcggccag    94320
gcagagacgc tcctcacctc ccagacgggg tcgcggccgg gcagaggcgc tcctcacatc    94380
ccagacgggg cagcggggca gaggcgctcc ccacatctca gacgacgggt ggccgggcag    94440
agacgctcct cacttcctag acgggatggc ggccgggaag aggtgctcct cacttcccag    94500
actgggcagc cgggcagagg ggctcctcac atcccagacg atgggtggcc aggcagagac    94560
gctcctcact tcccagacgg ggtggcggcc gggcagaggc tgcaatctcg gcactttggg    94620
aggccaaggc aggtggctgg gaggtggagg ttgtagcgag ccgagatcac gccactgcac    94680
tccagcctgg gcaccattga gcactgagtg aacgagactc cgtctgcaat cccggcacct    94740
cgggaggccg aggctggcag atcactcgcg gttaggagct ggagaccagc ccggccaaca    94800
cagcgaaacc ccgtctccac caaaaaaata cgaaaaccag tcaggcgtgg cggcgcgggc    94860
ctgcaatcac aggcactagg caggctgagg caggagaatc aggcagggag gttgcagtga    94920
gccgagatgg cagcagtaca gtctagcttc ggctcggcat cagagggaga ccgtggaaag    94980
agagggagag ggagaccgtg gggagaagga gaaggagggg gagggggagg gggggagagg    95040
gagagggaca atgatgtctt gctgtaggta ttcttcccca tttgaatttt ttcctcagca    95100
ttattttttt taacatcatt cagtctcctc ttatactaca cttggattga atttaatatc    95160
tcatgaagaa aaacatttc tactttgaag catgtgaatt agcatgtttt tataacagct     95220
ttattgagat ataatttaca tatataaata aaccgtttaa agtgtataaa tcagtggttt    95280
ttaatgagat ataatttaca tatataaatc aaccatttaa agtgtataaa tcagtggttt    95340
ttaaaatatt cacaatgttg tacaaccgtc ttctcagttg attttaaaac atactcttca    95400
cccccaaaag aaacccccgtg cccagtttag cagtcgttcc acatttgcct ccagcccttc    95460
tctttccccct actcccaacc ctaagcaacc gttaatctac tttctgtctc tatggatggg    95520
cttatttggg gcaaattcca tttcatacaa atggaataat aaaatatgtg gcttttatga    95580
ctggcttctt tcactcagag tagtgttata aaagttcatc catgttggag catgtttcag    95640
tacttcattt cttttgtga ctgactaata ttccttgatg tggataatac cacatttgt      95700
ttatccatta atcagtttgt agctatttgt ggtgttctca ctgtttgact attctgaata    95760
acactgccac aaacatgagt gtgcagtttt tttctcgtcc tatcttttca tttcttttgt    95820
gtacctacct aggagttgaa ttgctgggtc atatggcaac tgtgtttaac cttttgagga    95880
actaccaagc tatttgccaa gatatctaca ctattttaca ttcccaccag cagggtatga    95940
gggtttctgt ttctccacat ccttgctaac acttattgtc ttgtcttttt tgattatagt    96000
catccttgtg ggtgtgaagt gttaacctca ttgtggcttt aatgtgcagt tctttcatgg    96060
ctaatgatgt tgaacatctt ttgtgtttat tggccattta tatatcttct ttggattgat    96120
```

```
gtctgttcaa atctttaccc attttaaaaa ttgagttgtc tttttattat tgggttgtgg   96180
gagttcttta tatattgtgt gtacaagtcc ctgttagata catggtttgc aaatgttttc   96240
tcctgttctg ttggttgtct ttttactttt tcatcccttg aagcacaaaa attttttaatt  96300 ttgatgaagt ccaatttatc tgattttgaa gtaagctttt ggtgtcgtat ctaagaaaat   96360
actgtttcat caatcattaa ggtttattac tcttctgggt ttttttaaga attacattta   96420
gaggtgtgat ccatttggag caacttttt ttctttga cacagaatct cgctcttttg     96480
cttaggctgg agggcagtgg tgcaatcttg gctcacagca gcctcagcct cctgggctca   96540
aatgagtagc tggtactaca ggtgtgcacc accacccttt gctattaata acttttgtat   96600 tttttttgtag agacagaatt tcgccatgtt gcccaggctg gtctcaaaca cttggactca   96660
agtgacacgc ccacctcagc ctcccaaagt gaaaaattgc tttcaccttg cactgcggac   96720
tcgccctgaa ttctttcttg tgcaagatcc aagagccctc tctggggtc tggatcggga   96780 cccctttcct ataacaatat tatgagaata acatttgatt tttttaagt gaaacaaatt    96840 gttattaaaa aattaaaaaa ggtcatagga gagtgacttg gtgctcagcc cattttgagc   96900
agttatttaa tatagcataa ggtgggttc aaattcattc tttatattaa ttttttattt    96960
ctaattgaca cataaccata cacttataac cattttact gtgtaagttc agattcattc    97020
ttccgtatgt aggtattagt tgtcccagca ccatctgtta aaaagactat tcttggccag   97080
gcacagtggc tctcaacgcc tgtaatccca gcactttggg agtcccaagc aggcagatca   97140
catgaggtca ggagttcgaa accagtctga ccaaatggtg aaaccgcatg tctactaaaa   97200
atacaaaaat tacctgggtg tggtggcgca cacctgtagt ctagtcccac tactgtagtg   97260
gctgaggcag gagattcgct tgaacccagg aggtagaggt tgcagtgagc tgagatcatg   97320
cactccagtg tgggcgacag agtgagactc catctcaaaa aaaagactat tctttcctcc   97380
attgaattat cttcacatgc ttgttggaag tctgttgact acaaatgtga aagtttatta   97440
ctggactctg aattgtcctc cactgaatct ctatgtctta tccttatggc agtaccatac   97500
tgtcttgatt agagttactg tatttttaaaa ggctgtactt tttcagttag cagaaaacat   97560
tttagctatc agcacaactt tctgtaaacc ttcattaatg cttgacttaa attccaagaa   97620
ggagcaacat aaaaagtctt atctctttag gagttttagt cttactactt ttaggtgcct   97680
gaataaccaa atgtattatt tagcctctta ctaataactc cttgatccat aggggcatac   97740
caggaagaaa agaagtggtt tttaaaaaat gagagtgggc cgggcacggt ggctgatacc   97800
tataatccta acactttggg aggctgaggc gggtggatca cttgaggtca ggagtttgag   97860
accagcctgg ataacatggc gaaaccctat ctttattaaa aatatataaa ttagccgggc   97920
atggtggcac atgcctgtaa tcccagctac tcaggaggct gaggcaggag aatcacttga   97980
atccaggagg tggaggttgc agtgatccga gattgcatca gtgggcgaca gagcgagaat   98040
ctgtctcaaa gaaaaaaaaa gagagtggaa aaaaaaaata tgtgtcccag aacttaaatt   98100
ttaattaaaa aaaaataaaa gagtgaactt tctaattgtt ctcttcagat aatataatgt   98160
tattctctta tgttttattg cgtatttcct gtgtaccaga tgctgttctt catgcttgta   98220
tgttaaatct tgtctaacat ctctgtcaag caagttctgt ttgtatctgc actgtgtata   98280
ttaggcagct tgggcaaaga gaagttaagt aatctgccca aactcacatg gctagtaagt   98340
aagagggctg accatctggt gtttaagctt ctagcagtgc tttgaatagt aactaatgca   98400
tagtgcatgc tgcactgtca gtcagtgatt cattagagct aacttcatga catgctcata   98460
gccccaaact gcatttgttc acaaatatct gtagtccttc atttaggcag aaatagaaat   98520
```

```
accttgtgtg tttgttgttc cttcccttt gagccatatg cagagtgctg atagctttat    98580
ttgtgtaaga atttgctagta atttgatctg ttttgggtta ataatgtggg ttttagaggt  98640
aaatggacct aggtttgaat gttggcctct atacatcatg tgcgtaacat tgtggcatgc   98700
tatctacttc ccccaagcca aaatgggtta attttagaac ctgcttcata gtgttcctgt   98760
gagagctcga tgagatattg cctataaagt gtttagcata gtgcctagca catggtatgt   98820
attcaataca tgttcattct tactagcaaa atatagatga cccagtattg tacagagtat   98880
gtacaatggt gtcattgtac catttcatgt ggagtcacat aagaatttca gttttctgct   98940
gggcatgatg gctcactcct gtaatcccag cactttggga ggctgaggtg gatggatcag   99000
ctgaggtcag gagttccaga ccagcctggc cgacatgatg aaacccatc tctactaaaa    99060
atacaaaaaa ttagccaggc gtggtggcag gtgcctgtaa tcccagctac tcgcaagact   99120
gaggcaggag aaatgcttga acccgggagg cggtggttgc catgagttaa gatcgtgccg   99180
ctgcactcca gcctgggcaa taagagcgaa actccgtctc aaaaaaaag aaaaaaaag     99240
aacttaagtt ttccattaga tttagtatag tgcagagagg aaatacagca gagtgctata   99300
ttccatatat agcaatatag cattagaaca atatattcca atacagcaga gtgctatatt   99360
cagataccaa ctagtggact tgctatttgt aagatggcaa taatagtatc tacatcaaat   99420
agggctgttg tgaagactaa atgaataagt ctataaatag tttagaacag tgtctggaca   99480
ggtacagtgg ctcatgcctg aatcttagca ctttgggagg ctgagacagg tggatagctt   99540
gagctcaggc attaaagacc aacctgggta acatggtaaa accctgtttc tacaaaaaaa   99600
tacacacatt agccaggtgt ggtggcacat gctaatagta ccagctactc aggaggctga   99660
ggtgggagaa tcacttgagc ctgggagatg gaggttgcag tgaggtgagc ttgcaccact   99720
gcgctccagt ctgggcaacg gagtcagacc ctgtttggaa aaaaaaaaa aagtgtccaa    99780
cccatagtaa gaaatgcaga tgtgtttgac attgtaagaa aaagcaacac caaagtctg    99840
attttttgcct tcactcaaga actcttatga taattaaact ccgaagtcct tggcaatata   99900
tatagttggt ctgttatgtg gatcgcctct actaaagatt tttgtgaaca aatgaaagtt   99960
taagtagtaa gttcctacat cgtgacttaa attgccagtg tgcccacata aatacctgt    100020
caacatttgc ccttagccac ttgactcttt agctatattg gtaatgcagt aaagcttgcg   100080
atgcgccaga gttgcataat gctgtttgcc atgacaccaa gagccttggt aatgaaacca   100140
ttgaaattgg tttgcctata ctgaggctga agaggtatct tggctctcta attttaaggc   100200
aacctttttg gctgtgtagg tttctcttta gcttgtttct caccacctgg ggctgtggct   100260
taggtccgtt gtcctaacct gtggcttagg ttctgttttt gttgcttgta cttgctcccc   100320
cttttttcag ccattcctgt tttcttttctt ttgtagagga tgccatctta aatcatcttc   100380
agccagtggt agcattttat ttttttctggt ctgcaaactt aaaaacctca tcacttattt   100440
tgctaatatc tttgtcttct gttcttttg atggtccttg gttttgcagt ctactttaaa    100500
ggttttattt tttttatggg tacatagtag acgtattatt catagggtct gtgagatatt   100560
tagataaagg catataatgt gtaataatca cattagggta aatggggtat ccatcaccat   100620
catcattcat catttctttg tgtaatgaac gttgcaattg tactccctca gttattctaa   100680
aaagtacaac aaattaatgc tgactgtagt caccctgctt tgttgtcaaa tactagatct   100740
tattcattct ttatttaact ttttaaattt taaacttatt ttatttattt attttttagac  100800
ggagtctcac tctgtcgcca ggctggagtg cggtggcgca gtctcaactc actgcaacct   100860
```

```
ccgcctccag ggttcaagtg attctcctgc ctcagcctcc tgactagctg gaactacagg   100920
cacgtgccac cacgcccagc taattttttgt attttttagta gagacggggt ttcactatgt   100980
tggctgggat ggtcttgatc tcttgacctt gtgatccggc tgccacagcc tcccaaagtg   101040
ctggggttgc aggcgtgagc caccgtgccc ggccttttaaa attattttaa atcattttaa   101100 tatcttttttc atttctgcct ccggtcctgc agagttctta ttcgttcttt ctaaattttc   101160
tttgcaccca ctaatcacct catttcccctt cttctcccca ttacccttcc caacttctgg   101220
taaccattct gctatctcca tgtgttcaat tgtttttatt tttagtgcct gcaaacgagt   101280
aagaatatgc aaagtttatc tttctgtccc tggcttattt tacttaacat aatgtcctcc   101340
agtgccatct acattgctgc aaatgacagg atctcattct ttttttatggc tgaatggtaa   101400 tctattgtgt atatatacca catttttcttt ctccatttgt ctgtcagtgg acacgtaggt   101460
tgattccaaa tcttggctgt tgtgtatata gtgccgtagt aaacatggga gtgcagatat   101520
tccttcaata aactgatttc ctttctgagt atatacctag cagtgcaatt gctggatcat   101580
atggtagctc tatttttagt ttttttgagga atttccatac tgttctccat agtggtttta   101640
ccaatttaca tgtccaccaa cagtgtgtga aggttcccct ttatccacat cgttaccagc   101700
atttgttatt gcctgtcttt tggataaaag ccatttttaac tggggtgaga tgatatcttg   101760
ttgtagtttt aatttccatt tttctggtga tcagtagtat tgaataccttt tcatatacct   101820 gtttgccatt cataaataac gatgaggtct tgctgtttgg cccaggctgg tctcgaactc   101880
ctgggctcaa gcaatcctcc caccttggct tcccaaaatg ctgaaattat agttgtgagc   101940
cactgcacct ggccttgtat gtcttccttt ttttttttgtt ttgttttgtt tttgagacag   102000
agtctcactt tgttgcccag gctggagcgt agtggtgtga tcttggctca ctgcgcccta   102060
cacctcccgg attcaagcaa ttctcctgcc tcctgccacc atgtctgcct aattttttgta   102120 ttttttagtag agacgggatt tctccttgtt gcccaggctg gtcttgaact cctaacctca   102180
ggtgatttac ctgcctcagc ctcccaaagt gctaggatta caggcgtgag ctgctgcgcc   102240
cagcctgtat gtcgtctttt gagaaatgtc tattcagatc ttttgcccat tttaattga   102300 gttactaaaa ttttccctat ggagttgctt gagtgccttt tatattctgg ttattgatcc   102360
cttgtcagat gagtagtttg caaatatttt ctcccattct gtgggctgtc tcttcacttt   102420
gttgatggtt tcctttgctg tgcagaagct ttttaacttg atgtgatccc atttgtccat   102480
ctttgctttg gttgcctgta cttttggggt attactcaag aaatctttgc ccagagtaat   102540
gtccctggga gtttaatgtt ttcttttagt agtttcatag tttgaggtct tagatttaaa   102600
tctttagtcc attttgattt gattttttttt taatatggtg ggacacaggg gtctggtttc   102660
attcttctgc atatggatat ccagtttttcc cagcaccatt tattgaagag actgtccttt   102720
ccccagtgta tgttcatggc ttcttttgtgg aaaatgagtt cacttagacg tatggattca   102780
tttctgagtt ctctgttctg tttcattgat ctatatctttt ttttatgcca gtaccatgcc   102840
attttggtta caataatttg aagtcagata atgattcctc ccgttttgtt cattttgctc   102900
agtatggctt ttgctctttt gggccttttg tggttccccta caaatttttag aattattttt   102960 gtctacttct gtgaggaatg tcattggtat tttgataggg attgcactga atctgtagat   103020
tgctttgagt attatcaaca ttttagcaat attaattctt ctaatccata aacatggaat   103080
ctcttttcat gtttttttctg tgtcatcaat ttcagtgttt taaagttgtc attatagaaa   103140
tcttttactc atttggttaa gtttattcct aagtatttta ttatatttgt agctattgta   103200
aatgggattg cgtttaaaaa attttttcaga ttgtttgctg ttaaatataa aaatgctcct   103260
```

```
gattttgtg tgttgatttt tgtatcctgc aattttactg aatttgtttg tcagttctaa    103320
taggtttttc ttttttggag tctaggtttt tccaaatgta agatcatatt atctgcaaac    103380
aaggataatt tgacttcttc cattccagtg tggatgcttt ttatttcttt ctgttgtctg    103440
attgctccaa ttaggacttc cgagtattat gttgaataac aatggtgaaa gtgggcatcc    103500
ttgtcttgtt ccagatctta gaggaaagcc tttcagtttt tcccttttca gtatggtact    103560
agttatgggt ctgtcatata tggcttctgt tttgttgagg tatattcctt ctatacccag    103620
ttctttgggg tttttttgtt tgtttgtttt tgagatggag tctcactctg tcacccaggc    103680
tggagtgcag tggcgcaatg ttggctcact gcaagctcca cctcctgggt tcatgccgtt    103740
ctcctgcctc agcctcccga gtagctggga ctacaggtgt ccgctaacac gcccggctaa    103800 tttttttgtat ttttagtaga acggggtttt caccgtgtta gccaggatgg tctcgaactc    103860
ctgacctcat gatctgcccg tctcagcctc ccaaagtgct gggattacag gcgtgagcca    103920
ccacgcccgg ccaagggttt taatcataag gggatgtggc attttatgtg atataaatta    103980
tatatttata tcatgtgata tatatttata tcatacacag tataaataat atatatatat    104040
attttttagt ctttgtcttt tattctgtta agatgtacca tgtttattga tttgcgtatg    104100
tcgaaccatc cttgcatccc tgggatgaat cccacttagt catgatgaat gatctttta    104160 atgtgttact gaattcggtt tgctagtatt atattgagga tttttgcata atgttcttca    104220
gagacactgg cttctagttt tccctttttg atgtgtcctt tggttttgta tagggtaata    104280
gtggccttgt agaatgagtt tagaagtatt ccctcttcct gtattgtgtt ggaatagttt    104340
gagtaggatt ggtattagtt cttctttaaa ggtttagtag aattcagcag tgaagccatc    104400
aggtccatgg cttttctttg ctgggagact atttcttata gctttgatct cgttacttgt    104460
tattggtctc gttacttgtt attgtatttg ggttttggat ttctttgtgg ttcagtcttg    104520
gtaggttgta tgtgtctagg aatttatcca tttcttcaag gttttccaat gtatcagcat    104580
atagatgctc atagtagtct ctaatgatcc tttgaattttc ggtggtaaca attataatgt    104640
ctcctttttc atctctcatt ttattatttg ggttttctct tttttttctg agtctggcta    104700
aaggtttgtc agttttgttt atctcttcaa aacaatttac tgttttattg atcttttgta    104760
ttttcttcat ttcaattta tttatttctg ctttgattt ttttatttct tctactgatt    104820
ttaggttttg tccttgcttt tctagttctt taggatgtat tggcagatga agttttcca    104880 cttttttgat gtaggcactt actgctgtaa acattcctct tattgttgct tttactgtat    104940
cctataggtt ttgataagct gtgtttccat tttcattgt ttcaaggaat tttccagttt    105000
tcttcttaat ttcttcatgg acccactggt cattcaggag catattgctt aattttcatg    105060
tatttgtata ctttccaaag ttcctcttgt tatctagtgt tattttattt tatttttatt    105120
tttgtttttt tgagatggag tctcgctctg tcacccatgc tggagtgtag tggcgcgatc    105180
tcggcttact gcaacctctg cctccccagt tcaagtgatt cttctgcctc agcctcctga    105240
gtagctggga ttacaggcat gtaccaccac tcctggctaa ttttttttg tattttagt    105300 agagacgggg tttcaccatg ttggtcaagc tgatctcgaa ctcctgacct cagatgatcc    105360
acccaccttg gcctcctaaa gtgctggaat tacaggcatg agccaccgtg cccggcctct    105420
agtgttatct tattgtgatc agagaagata gttgatatga ttttaacttt tttgaatttt    105480
tatttattta tttgtttgtt tgtttgtttg tttgtaacag agtctcactc tgttacccag    105540
gctggagtac atgtcatgat cttggctcac ctgcaacctc cgccttcctg gctcaagcaa    105600
```

```
tcctcccacc ttagccttcc aagtagctgg gactacaggc acatgccgtc acatatggct   105660
gatatttttg gattttttt tttttgtag agatggggct ttgcgatgtg tcccagggtt    105720
gtttcgaact cctgagctca agcaatccac ctatttcggc ctcccaaggt gctgggatta   105780
cagacatgag ccactgtgcc acgtcaaatc tttagacttg ttttgtggct taacataggg   105840
tctatctttg agagcaatcc atatgttgag gagaagaatg tgtattctat agctgttgga   105900
cacaatgttc tgtaaatatg tattgggcct atttggtcta tagagcaaat taggtctaat   105960
gtttctttgt tgattttctg tctgaatgat ctgtccattg ctgagagtgg ggtgttgaag   106020
tttccgactg ttactgaggt ctgtttctct ttttgctct aataatgttt gctttatata     106080
tctggatgct ccagtattgg ttgcatatgt atttatactt gttataacct cttgccgaat   106140
tgatcccttt atcattatac aataatcttc tttgtctgtt tttatagact ttgtctcaaa   106200
atctatttta tctaagcata gctactcctg ttcttttctg gtttccattt gcatggaata   106260
ttgttttcca gctcttcaat tttagtctat gtgtgatttt ataggtaaag tgtgtttctt   106320
gtaggcaatg gatcttggt tttttttttt ttttttttga cacagagttt tgctattgtt     106380
gcccaggctg gagggcaatg gcgctatctc agctcactgc aacctccgcc tcctgagttc   106440
aagcgattct cctgcctcag cctcccaagt agctgggatt acaggcgcct gccaccaagc   106500
ccagctaaat ttttgtatt ttcagtagag atggggtttc agtatgttcg tcaggctgtt     106560
cttgaactcc taacctcagg tgatttgcct gccttggcct cccaaagtcc tgggattaca   106620
ggcgtgagcc accgcaccca gcctttttt taaatccatt tagccactct gtatcttttg     106680
attggagagt ttagtcgatt tacattcagt gttgttactg attagtgagg acttaactac   106740
taccattttg ttacttatta tctggttgtt ttgtagtcct actccctccc ttccccttc    106800 tttttactt cctcttcgct cctttttcc ctccctccct tccttgtttt gaaagtgatt      106860
ttctctggtg gtatgtttta atttcctgct ttatattttt tgtgtatctg ttgtaggtgt   106920
ttttgattta agatcaccat gacagctggg tgcagtggtt cacacctgta atcccagcac   106980
tttgggaggc cgaggtgggt ggatcaagag gtcaggagat tgagaccagc ctggctaaca   107040
tggtgaaacc ccatctctac taaaaataca aaacttagcc aggcgtggag gcacgtgcct   107100
gtaatctcag atactcagga ggctgaggca ggagaattgc ttgaacccag gaggcagagg   107160
ttgcagtgag tcaatattgt gccactgcac cccagcctgg gcgacagagt gagactccgt   107220
ctcaaaaaaa aaaaaaaaa agagatcaca taagggttgc aaataacatt ttataaccca    107280
ttattttaaa ccaatgacaa cttgaaactt tgattgcaaa acaagcaag caaagagaaa    107340 actaataaaa actctacact tcatctgccc gcttttaac ttttgttgtt tttatttata    107400
tctttattat actatgtctt aaaaaactgt agttataagc caggcgcagt ggttcacgtg   107460
tgtaatccca gcactttggg aggctgaggt gggcggatca cctaaggtca ggagttcgag   107520
accagcctag ccaatatggc aaaaccccct ctctactaaa aatagaaaaa ttagccggac   107580
atggtggcgg gtgcctgtaa tcccagctac tcggaggctg aggcaggaga atcacttgaa   107640
cccaggaggc ccaggttgca gtgagccgag agtgcgccac tgcactccag tctgggcaac   107700
agagtaagac tgtctcaaaa aacaatacaa aacaaaacaa acccctggcc tagtggctca   107760
cgcctaatcc cagcactttg gaaggcaaag gtggggcgaa tcacaaggtt aggagttcga   107820
gaccagcctg accaacgtgg tgaaactctg tctctactaa aaatacaaaa attagccagg   107880
cgtggtggca cgcacctgta atcctagcta ctcaggaggc tgaggcagga gaatcgcttg   107940
aacctgggag gcggaggttg cagttagccg agatcgcgcc actgccgtcc agcctgggca   108000
```

```
gcagagcaag actctgtctc acaaaaaaaa aaaaaattgt agttcttatt tttgaaaggt    108060
tcatttttta ttcttcctgc tcaaaatatg agtagtagtt tatacaccac aattacagtg    108120
ttacaatatt ctgtattttt ctgtgtactt gttaccagtg agttttttgca ccttcaggtg   108180 atttattatt gtttgttaac atccttttct tgcagattga agaacttttt ttttttttt    108240 ttttttttga gacagagtca tgctctgtta ccagcctgga gtgcagtggt gccatcttgg    108300
ctcactacaa cctccaactc ccaggttcaa gcgattcttc tgcctcagcc tcccaagtag    108360
ctgggattac aagcatgtgc caccacgccc agctactttt tgtatttta gtaaagacgg     108420 ggttttgcca tatttgccag gctggtcttg agctcctgac ctcagggtga tccgcccgcc    108480
ttggcatcct aaagtgctag gattataagc gtgagtcatc gtgcccaact tggttgttta    108540
ttttcaaata gcctgaattc aagctcacta atgttttctg ctgcttgata catttctgct    108600
attgagagac tgatgcattt ttcagtttgt caattgaatt tttccacttt gggattctg     108660 cttgattctt tttactaata attattgcag tctcttttt aaatttatag gattctgaat     108720
ttgttctctg tattatcttg gatttcgttg aactttctca aagcattcag cttgaattct    108780
gtctgaaagt tcacatatct cttatcactt gggaattggt cactggtgtc ctttattttt    108840
agttcatttg gtgaggtcat gttttctcag atggccttga tgcttgtgga tgttcatcag    108900
tgtctgggca ttgaagagtt gggtattctg ttctttgtag tctggttttg tttgtacgca    108960
ttcttttttt tttttttctg tttttgagac agagtctcgc tctgtcgccc aggctggagt    109020
gcagtggcac agtctttgct caccgcaacc tccgtctccc ggattcaagc aattctcctg    109080
cctcagcctc ctgagtagct gggattacag gtgcgtgcca ccacgcctgg ctaattttg     109140 tatttttagt aaatatggtg tttcaccatg ttggtcaggc tggtctcgaa ctcctaacct    109200
cgtgatctgt ccgccttggc ctctcagagt gttgggatta caggcgttag ccactgcatc    109260
cggctcccat tcttcttgag aaggttttc aagtattcaa agggaattaa gtgttgtcat     109320
ctaagtcttc gctcactgca gccatacatg cattagaggg caccccaaga ctagtaatgt    109380
tgtgactctg tagaggtatc accttggtag tcttggggaa gatctgggag aattccctgt    109440
attaccaggc agtctcttgt cctcttacat ttctccaaac aaatggagtc tctctttgtg    109500
ctgagctgct tggagtttgg ggaagggtga cacaagcact gccatggcca ccgtcactgg    109560
aactgtactt ggtctcaccc aaggcctgtg gcagctattt tctggccacc actgatgtta    109620
atttaaggcc caagggtgct ttagtcagta ggtgaagaat cctgcaagaa ctgggtcttt    109680
actttcagtg cagcaggttc ccttctggcc cagggtgtgt ctagaaatgc tgcccaggag    109740
ccagggcctg ggatcgggag ctttaggaat ctgctttatt gtactggggc tgagctggca    109800
cccacttgca agataaagtc ctttttactc ttctctcacc tcaagcaggt gggtctcccc    109860
atggacacca cagctgtgaa tgtgcggggt catatctgaa gctggcacaa tacgacatgg    109920
caccttgttt tttattcaag gcacaagggc tctttagtca gctggtggtg aatcctacta    109980
ggactaggta tttcccttca aggcaatggg ttcccttctg gtccagaata tgtctagaaa    110040
tgtcatctgg gagctatggc ctagaattga ggcttcagaa ctatgcttgg tgctttattt    110100
tactgtggct gaactagtat ccacattgca agacaaagtc ctcccctactc ttccctctcc   110160 tcccagagct gtgagctgtg gtacctggag ttgggggaag gctggcacaa gcactccctt    110220
ggccacccta gctggtgtct cagtgggtca catgtacccc aagtccactg actatgagcc    110280
cagcacagta ccatgacttg tccaggaatt gcagtccttc tggtctagac tgcctttcaa    110340
```

```
gtttatttag accccagag actttaccc acggtggtgg ggcttaccaa aattaagatt   110400
cttttggttt tttttggcag agtttcgctc ttattgccca ggctggagta tagtgacgca   110460
atctcagctc accacaacct ccgcctcccg ggttcaaata attctcctac ctcagcctcc   110520
tgagtagctg ggattaccgg catgcgctac cacctctggc taattttttt gttttttagt   110580
agagatgagg tttctccatg ttggtcaggc tggtcttgaa ctcccgacct caggttatcc   110640
gtccgcctcg gcctcccaaa gtgctgggat tacagaccat agtgcccagc ccgaaattca   110700
gattctaatc actgggatgg acaattcccc tctgactagg gctagtctaa atactccctc   110760
tgtgggtgct ggctgaattc tgtcctatgc tgctttccac tgtgacaggg cagcactgag   110820
tttcaatgca aaatcccaca gtcatttctc tctctctccc ccgagcacac agattctttc   110880
tccaccccac actgcattgt gggggaatgt caggggtgtt ggaggggcag ttcaagacta   110940
tcttccttat cttttttggt gtcttttttcc ttgataggat gtcaaaactg ggtactgtga   111000
tcgcttacct aattttggt tcttatgaag gtgctttctt gtgtggatag ttgttcaatt   111060
tggtgctcct tgttggggat gatcactgga aggttctgtt tggccaccat gctctgtctc   111120
ttctcccctg ccatctcctt tttttactta ggggtttaga atgtctaact gaccaatatg   111180
tacagtcagg tctcattctg aattcaccta cttaatgacc ttccaagctg actaggccca   111240
gcgcttagtc cagcctccat gacggtccct ccacatccta attagcctcc ctccagttca   111300
tttcacacaa agctgctgtg ttcacctttc tgaactataa atctgcccag tactctaccc   111360
tacttaaaat tccgtataga ctgcccattt gccctgagaa ttaaaagcca agtcctaaa   111420 cgtagctttt taaaactttt tttttttttt ttttaatttt tagatggagt cttgctctgt   111480
cacccaggct ggagtgcagt ggtgtgatct tggctcactg caacctccgc ctcctgggtt   111540
caagcaattc tcatatgtca gcctcccaag tagctgggat ttacacgtgt gccatcacgc   111600
ctggctaatt tttttttttt atctttagta gagacggagt ttcaccatgt tggccagtct   111660
ggtcttaaac tcctgacctc aagtgatcca cctgccttgg cttcccaaag tgctaggatg   111720
ataggtgtta gccactgcac gcagccctga acatagcttt taagttcctt tattgtcata   111780
ttccttttga cgagtctatc attttctgac tcacttgtac atgtgtgtct cacccttggt   111840
ccagccattg gtgcttttct ttacttcttt attttttgtta ttttattttta ttttattatt   111900 attttttaaa tgagacaggg tatcactatg ttgcccaggc tggtcttgaa ctcctgagct   111960
taagcagtct gcttgtctca gcctcccaaa gggctggaat tacagtgatg agctactgtg   112020
cccagctcat tggtgctatc tttttttttt tttttgagac ggagtctcgc tctgtcaccc   112080
aggctggagt gcagtggcgt gatcttggct cactgcagct ccacttccca ggttcacacc   112140
attctcctac ctcagcctcc cgagtagcag ggactatagg cgcctgccac catgcctggc   112200
taatttttgt atttttagta gagatggggt ttcagcgtgt gagccaagat ggtctcgatc   112260
tcctgacctc gtgatccgcc tgccttggcc tcccaaagtg ctgggattac aggcgtgagc   112320
caccgtgccc ggcccccatt ggtgctattg ttttatgtga tagagccagc ttctcccttt   112380
tctttggatt tttaaacata ctcttccttt tacttagact attctccatc ccaacacctt   112440
tcctaaactt cttttcacacc ttagactagc tgacactttta ctgagaaacc tttctttttt   112500
ataggttgct ttttctatag actctcttag catttactca ttttattgtg aagtgtctga   112560
tcttatttaa atgacaagta taagaggata gaaactattt catattttc tcacccagca   112620 ggcacaattt ctgacatgtg gtaagcactc agtaaatatt gaactttaga ggctaggaca   112680
tttgagtgct ttggtgactg tggttgtgct atataggtac tctgttattg ttagtttata   112740
```

```
gtaaaagcat tactcttaaa gtatgaaaaa agccttattc agaacatttc atgcgtatag    112800
ttaatattac gtagcttgtg ctcatggcaa aaatgtatta ctaaagttat ttaagatatt    112860
taagtataat tgtttccttt atttagttac agccaagttc tacttctgaa tctatggatc    112920
aactactaaa caaaaataga gagggagaaa atcaagaga  tttgatcaaa gacaaaattg    112980
aaccaagtgc taaggattct ttcattgaaa atagcagcag caactgtacc agtggcagca    113040
gcaagccgaa tagccccagc atttcccctt caatacttag taacacggag cacaagaggg    113100
gacctgaggt cacttcccaa ggggttcaga cttccagccc agcatgtaaa caagagaaag    113160
acgataagga agagaagaaa gacgcagctg agtgagtaaa cctggaactt agaccatcct    113220
gttactcaat taactttttt tttttttaaag gcatttaggt ccttccaact gtgaagaatc    113280
catctggact tttagactac tttatacatt gcccttagtt tacaaacagc tagtccaaac    113340
aaatgacatc ttaagtaaat gaggttattg caccctgtgc tactcttctg ttcttcccct    113400
tttttgtacc ccagggctag aaaaacaagg cataaattaa gaaagttttt tctgtaaatg    113460
aacaggagtt gaaaaattat caattcaggg gacctatctt tactggattc cactcattag    113520
tcaccctcac tgtgctgcta ggttgaaaaa ctgccactgt caaggagaga agcatgcggt    113580
gcttctactt ggaattcaaa atattttttca tcagaaactg tgttttagtt aatgtttaga    113640
tttgttaaga tagacttaat tctgcacatt cagtatatta attaaatgga cttttagggg    113700
ctaacctcag aacttaacta ccattgactt aggtgtttgg gtaccaaaca atccagttaa    113760
agctgaagtt ttggaatgca gcttattgat aaattgggga ctgcttattc ttgatttgag    113820 gcaattttt  tttacagcca tgactttttc caggtatgtc atgtaaaata tcttctcaca    113880
taagaattac tgcatgctag aatattggta tgttgactgg tagctcatac ctataatccc    113940
agcactctgg gaggtccaag caggtagatt acttgaggtt aggagttgaa gaccagcctg    114000
gccaacatgt gaaaccctgt ctgtactaaa aatacaaaaa ttagccaggc atggtggtag    114060
gtgcctgtat cccagctact cgggaggctg aggcaggaga attgcttgaa cccagaaggt    114120
ggaggctgca gtgagccgag atcatgccac tgcactccag cctgggtgac agagcgagac    114180
tctgtctcaa aataaataa  ataaataaat aaaaggatac tgttatgtta agaattgctt    114240
ttaaggatat ttcataagta gctactgtct tttcagctca agtgtttgtt gattggccag    114300
gcgtggtagc tcatacctgt aatcccagca ctttgggagg ctgagtcagg cagatcactt    114360
aaggtcagcg tggccaaaat ggtgaaaccc catctttact aaaaataaat attaaaaaaa    114420
attagctggg cgtggtggca gtctcctgta atcccagcta atcaggaggc taaggcaaga    114480
gaatggctta aactcgggag gcagaggttg cagtgagcca agattgcact gctgcactcc    114540
aacctgagca acagagtggg actctgtgaa ggaaaaaaaa aaagtatttt ttgattgcct    114600
ttgagaggaa cggttgtata ttactcagat ttttaaaaaa ttgttctttt atggctgtat    114660
tctttaaggg attaaggaat gggcaatata agtgtatatg tttcaataaa acgattagt    114720 gatcttctag tgagaacagt ttaaatctat atttagcaat tttttttaaa ttgtcaggta    114780
tggaagattt tagagcaacg taaagtccat gtagatttca ctggccttta tattttttt    114840 aggcaagtta ggaaatcaac attgaatccc aatgcaaagg agttcaaccc acgttccttc    114900
tctcaggtag gtttattact ttctttgagg ttatctagtc ccaaaaaaag aaaaattatt    114960
agtaatagtc cttcttccat acctgccatc tgaattttgt tttagtgtgc tgaaccaacc    115020
ttctttcttt tttttacatg gccattaatg aatacttttt aaacattaaa aaaggtctt    115080
```

```
tgttttgtca tcaattagat gtgatcttgg gcaaatcttt gaatttctct gacccagaat    115140
ttgacgatgg ttggctagct aggctgtcag gtttatagat acgtcctctg cacctgaggg    115200
ttttgcatca ctggattcaa ccaaccatgg atcaaaaaca tagttaggat aatctatact    115260
gaacacatgc agacgtttcc ttgtcattat tccaaaacaa tacagtaaag catttaccct    115320
gttttaggta ttataaataa tctagagatg atgtaaagta tataggagga tatgcatagg    115380
ttgtatgcga atactacatg atttatgta agggacttga gcattccaag actttggtat    115440
cttcacaggg tactgtaacc aatcccccac agatactaag agatgactgt actattgtta    115500
ttattcgact gagatcataa gaagatatat ttatttttaa ttttttaaaaa cacttccatc    115560 agtttcttaa aaatagctgc cactgttttt aatatttttt aattgacaaa gttttaagtt    115620
cctactgaaa cattttttct tttattgaaa tgtgaaaatt tatgtgctgt gtttttgttt    115680
tcaataaaag ggacatagtt aaagcaagta aaattagaaa gactgggaaa atccgtcttt    115740
aaattgcaat aatagttcat ctgttaccttt gagataattg aatttattgt tgttttgta    115800 gccaaagcct tctactaccc caacttcacc tcggcctcaa gcacaaccta gcccatctat    115860
ggtgggtcat caacagccaa ctccagttta tactcagcct gtttgttttg caccaaatat    115920
gatgtatcca gtcccagtga gcccaggcgt gcaagtaagt catagaattt gatgttcact    115980
tagcctcccc aattgtttgt atctgacacc aagcactctt taggttttca gtgacttgag    116040
ggtgtgatgg ttatgcatat gcatttgaaa cagacaggca tgcagagatt cagtgtgttg    116100
ttaagtatga ggacctaaat ctgagaatgt tttctgtgaa aaagatggtt tagatttact    116160
gtagtttggg gtttgttcct tttagctgtg ggtatgatct aattttttaa tgactaatgg    116220
agaatcagga aaccttctca tgcctagctc tctagcaata taaaactaag agtgacagaa    116280
taccttgtta ttatcatagg tgcctaatgt taatttttttt tttaattctc tcaagccttt    116340
atacccaata cctatgacgc ccatgccagt gaatcaagcc aagacatata gagcaggtaa    116400
aggtgagaat aatcctgcct gtgtttgctt gtagtttgca tgctgcatga attgagtaac    116460
taagtttata atgaataaat agttgtagtt tagctctgac ttttttgatga ggctatgcat    116520 tggcttttga tgaacaacat tacatagata ttcacatgga ttttatgaag aaaaacaggg    116580
gagaaaaaat gcccatcagt tgtgattata tagtatcctc ttcaaaaaga gtaattggag    116640
gcctggtgtg atggctcaca cctgtaattt tagcactttg ggaggccaag gcaggaggat    116700
tgcttgagct caggagccca agatcagcct ggacaacaga gactttgtct ctactaaaat    116760
tcaaaaaaat tagctgggca tggtggcata tgcctgtagc cccagctgtt tgggggactg    116820
aggcgagagg atcacttgag cccaggaagt agaggctgca gtgagctgtg attatgccac    116880 tgcccctccag cctgggcgac agagtgagac cccgtctcaa acataaatac tggctgggca    116940
tggtggctta tgcctgtaat cccagcactt tgggaggccg aggtgggtgt atcacctgag    117000
gtcagtagtt tgagaccagc ctggccaaca tggcgaaacc ccatctctac taaaatacaa    117060
aaattagccg gacatggtgg cacctgccgc ctgtaatccc agctactagg tggggctgag    117120
gcaggagaat tgcttgaacc cgggaggcag gggttgcagt gagccaagat cgtgccactg    117180
cacttcagcc tgggcaacag agtgagactc catctcaaaa caaacaaaca aacaaaaac    117240 aaacaaacaa aaaaccaga ctaattggct ggacacagtg gctccatgcc tgatatccca    117300
gctggaggat gacttgaacc catgagttcg agagcagcat gggcaatata gtgagaccct    117360
atctcaaaaa aaaaaaaaaa agttaattcc aaagctttt gatctgaaat ctgatttaaa    117420
tctgaactta aatttgaaga agagggtttg ctagattaat ttactagatt gctaaccttg    117480
```

```
ctttatatat acctacagtt atttccccaa agccagaatt tcttttgaag cagaggggca    117540
actaacttca accaatgtta agatcctatt agaaggatgt ttcggctagg cttggtggct    117600
cacgtgtaat tccagcactt tgagaggctg aggtgggcag atcacatgac cgggagtttt    117660
aagaccagcc tgggcaacat ggcaaaaacc tatctctgca aaaaaaaat agaaatctta    117720 gccagccgtc atggtgtgct cctgtagtcc tagctacttg ggagactgag gtgggaggat    117780
caattgaaac cagaaggtcc aggctgcagg gaactgtgac tgcaccactg gctccagct    117840 tgggtgaaag agcgaaaccc tgcctcaaaa agaaaaataa gatggatgtt tctgcattaa    117900
aattagggag ttgtcgtata atgtagttgc ataaactagt attctgtgct tgtgtggtta    117960
aagagccttc gtagaaaaaa tcccacattt ttcttaaaag gaaatctttt ggccaggtgt    118020
ggtggctcac atctgtaagc ccaacactct gggaagccga ggtgggcaga tcacttgagg    118080
tcaggagtac aaaaccatcc tggccaacat ggtgaaaacc cgtctctact aaaaatacaa    118140
agatcagctg ggcatggtgg tgcgtgcctg ggtgacagag cgagactccg tccaaaaaaa    118200
aaaaaaaaaa aaaagagttc ttttaatgtt ggaaaatgct aaagggtttt tttttgcca    118260 accagttaat ttagagtgat taactgctat cagttgagaa actatagaaa gtagaataat    118320
ttatacagaa aagacatttc tcagtgccca ataattgcct ttctgacata aagttttcat    118380
ttttcctgaa ttaataagat ttcctcaatg tgttttttg ggtgttttgt gtgtgtgtgt    118440
gtgtgtgtgt gtgtgtgtgt gtgtgtgtgt gtatgtgttt gatacagggt cttgctttgc    118500
tgctgaggct ggaacgcagt ggcgctatca tggctcaatg cagccttgac ctcctgggct    118560
caagcgatcc tcccttctca gtcccctgga tagcggggc tacaggtgca caccaccaca    118620
cctagctaat ttttgtattt tttgtagaga tgggttttgc catgttgcct aggctggtct    118680
caaactcctg ggctcaagcg atctgcctgg ctctgcttcc caaagtgcct gcgcccagcc    118740
aattttctcc atgtttgacc taattgtgat ttcatagatg ttaactaaaa ctcttaattt    118800
tcgttttctc agtatgctat tttttttttt tttagccttg gaacatatga acctgttgaa    118860
agaactctgc ctgaaataat gtaatcaaat tatagagttt aatcttattt tgagggcctt    118920
tagaaattct gagaagaaag tgggtttttt ttttactgc cattttaatg tagtgttaag    118980
gtgttcatgt atcaccagca ggtgtagctg ttttcaatga ttacttaaaa caatgcaatg    119040
ggaacttttt gttgtcatta aaatataaaa ggttactgta gtaagagcaa gcatgacagt    119100
ttggctatct gatgggagag tcacattcta acttcaggag gtactgtctt tttaatagaa    119160
atgatatact cagagtctgg gcacggtggc tcacgcctgt aatcccagca tttgggaggc    119220
cgaggtgggc agatcacgag gtcaggagat caagaccatc ctggctaata cagtgaaacc    119280
gtgtctctac taaaaataca aacaattagc tgagcgtggt ggcaggtgcc tatagtccca    119340
gctactcggg aggctgaggc aggagaatgg catgaacctg ggaggcagag ctggcagtga    119400
gctgagatgg tgccactgca ctccagcctg ggtgacagag cgagactccg tctcaaaaaa    119460
aaaaaaaaaa aaaaatagt agagaaaggg ctttgccatg ttggccgggc tggtcttgaa    119520
ctcctggcct caagtgatcc acctcccctcg gcctcccaaa gtgctgggat tacaggtgtg    119580
agccactgct cctggcctga atataccact tttacctatc atcagttgat gaacatttgg    119640
attatttcct ttttctggca atgagtaatg cttttgtgga ttttcatgta caaatttca    119700 tatgaggctg ggagcagtgg ctcatgccta taatcccagc agtctgggag ctgaggtgg    119760 gcagatgact tgaggtcagg agtttgagac cagcctggcc aacatggtga aatcccatct    119820
```

```
ctactaaaaa tacaaaaatt acactggcat ggtagcgtgc acctataatc ccagctattc    119880
aggaggctga ggcaggagca tcagaatcgc ttgaacctgg gaggcggagg ctgcagtgag    119940
ctgagatcac accactgcac cccagcctga gtgaaagagt gagtctcaaa aataaaaaa     120000 taaaattttt tttcatgtgg ccttagattt tcatttctcc taaagtagaa atgctgtgat    120060
ggaactgcca aacttttcca aagcagctgc atcattttgt atttctacca gtaatgtaca    120120
agtgttccag tttctccaca tcctcataaa taaccgatat gtctttggtt tgggttatgt    120180
ccattctagt ggttatgaag tgtcattgtg gttttttgtt ttttgtatt gttttgagat     120240 cgtgcccagg ctggagcaca gtggcacaat ctcggctcac tgcagccttc gcttcctggg    120300
ttcaagcaat tctcctgcct caccctccca gatagctggg gctgcaggca tacgccacca    120360
caccaggcta atttttatat ttttgtaga gatggagctt ctccgtgctt cccaggctgg     120420
tctcgaattc ctgagctcaa gcgatccccc tgcgtcagcc tccagagtag ctggggttat    120480
aggcgtgcac caccgcgctc ggcccatttt tgtattttta gtagagatgg aatttcacca    120540
tgttggccag gctggtcttg aactcctgac ctcaaatgat ccgcctgcct caccttccca    120600
aagtgctgag attttagacg cgaaccacca tgccctgact ataggttatc ttttacttg     120660 cttgatggtg ttctttgtaa cacagttttt aattttgatg aagttcaatt tatctgtttg    120720
ttttttcttt tgttgctgtt gctcctgatg tcatatcaga caaagcattg cctaactcaa    120780
ggccacagag atttactcct atgaaacgcc tataaaactc ctatgatttt tatagtttag    120840
ctcttaacat ttaagtctac aatctctttt gagttaattt tgtgtatga gatgagagta     120900 gtggtccagg ttttttcttt tgcttgtgga tatccgttgt ccccacctca tttgttgaaa    120960
agactattct ttcctcttaa attgtttgtt tgtttattta ttttgagat ggagtgtcgc      121020 tctgatggag tggcgctaac ttagcttcac tgcaacctcc gcctctcaga ttcaagcgat    121080
tcccctgcct cagcctcctg agtagctgga attacagggg tgcgccacca cccagcta     121140 attttgtat ttttagtaga cgggggttt taccgtgttg gtcaggctgg tctcgaactc      121200
ctgatctcgt gatctgcctg tctcctggca ccctgggagg ctgagaggct gaggtgggag    121260
gatcacttga gctcaggagt ttgagaccag cctgtaccat tatgcctggc taattttaga    121320
atttatctta aagtataaaa tgtgaatcca atttatcttg ttctaaatga ctatccaaaa    121380
tgttttaacc agttttatta gtctgtaatt tacatacaag aaaatgctca tctttttatg    121440
tttacatttt aatgagtttt gacaaatata tttgctcatg taactacttg cttcatcagt    121500
gaagatggaa acattgtgc ctgttcctct tctctgtcca actgtacttt attaccacta     121560
gctccagtta accagtaatc tgccttcttt tactatagat tagatttatc ctctttagat    121620 ttcttttct tttttttttt ttgattaggt ttttttttt cttttttac gtaaaaaaat       121680 ctttttttgg agacgtctca ttatattgcc caggttggtc tcgaactctt gagctcacct    121740
cagcctccca gagtgctagg attacagatg tgagccacct cagccagccc ctagattttt    121800
tttttttttt taataaatgg aatcaaacag cgtgtaacag aggtgttcaa tcttttggct    121860
tccctgggtc atattggaag aagaattgtg ttgggccaca cataaaatac agtaacacta    121920
atgatagctg atgaacaaaa caaaaaaaaa tagcaaaact tataatgttt taagaaagtt    121980
tatgaatttg tgttgggcca cattcaaagc cgtcccagga cgcaagttgg acaagcttgg    122040
tatataattt catatgtgtg tcctaaacag tgtagtaatt tgaatttcat gttagtatca    122100
gcttattcct ttttgtttgt ttgtttgttt ttgagatgga gtcttgttct gtgtcccaga    122160
attggtctgc aattccactg cctcagcctc ccaagtagct gggattacag gcacgtgcca    122220
```

```
ccacacctgg ctaattttg tctctctctc tttttttttt tttttttttt tttttagca 122280 gagacgggat ttcaccatgt tggccaggct ggtctcaaac tcctgacccc aaatgatcca 122340
cctgccttgg cctcccaaag tgctgggatt acaggtgtga gtcaccgtgc ccagccagct 122400 tattccttt tattgctggg tagcatttca ttttatgatt ataccacagt taatttaccc 122460
attactagtc gatgggcatt tgagttattg ccagcttttg gctattatga atgaagctgc 122520
tgtgagcatt tgtgtacaag tgtttgtgtt tttatttctt ttagttaaat acctagaatt 122580
ggaattgctg aggtatggta agtgcatatt tcattttttt aaaaaattta ttttattttt 122640
tatttattta ttttttttga gatgaagtct cactctgttg cccaggctgg agttcagtgg 122700
cgtgatttca gctcatggca acctccctgt cccgggttca agcaattctc ccgcctcagc 122760
ctcccaagta gctgggatta caggcgcgca ccaccatgcc tggctaattt ttttgtattt 122820
ttagtagaga cggggtttca ccacgttggc caggctggtc tcgaactcct gaccacaagt 122880
gatccacccg ccccagcctc ccaaagtgtt gggattacag atgtgagcca ccacacactg 122940
cctggtaaat acatatttca attaataaga aactagcaat cttctaaagt gattgtgtca 123000
ttttacattc caactgatca ggtacatgtg taggttccat gtgttctgca tccttgccaa 123060
cacttggtat tgtgttatct ttttaatttc aacaggtcta atgggtgtct tatggtatct 123120
cattgtgatc ttaaatgtac atttctctga tgatgactga tccaggagca cctcatcatg 123180
tgtgtgtttg ttttcagctg tcaaccttt tttagtaaat ggttcaaatc ttttttccat 123240
tttatttatt tatttatta tttgatggaa tctcactcta ttgcccaggc tggaacgcag 123300
tggtgccatc ttggctcact gcaacctccg cctcccaggt tcaagcaatt cttacgcctt 123360
agcctcccaa gtagctggga ttacaggcat gcgccaccat gcctggctaa ttttgtattt 123420
ttagtgtagg tggggtttca ccatgttggt catgctggtc tctaactcct gacctcaggt 123480
gatctacctg cctcggcctc ccaaagtgct gagattacag gtgtgagcca ctgcgcctgt 123540
cctaataatt tctttttgtc tcaatgtttc tgcctgggtg cactggctca cgcctgtaat 123600
tccagcactt tgggaggcca acctggatgg atcatttgag ccaacagttt gagaccagcc 123660
tgaggaacat gacaaaaccc tgtctttgca aaaaaaaaa agaaaaaaga aaattagcc 123720 aggcacagaa gcgcattcct atggtcccag ctacttgggg ggctgaggtg ggacaatcgc 123780
ttgagcgagg ttgcgggggt ttggagggcg atggagggt gatcgaggtt gcagtgagct 123840
gagattgcac tactgcactc cagcctgggc aatagagcca gaccctgtct cacaaaaaaa 123900
agaaaaaaaa gtcatgtttc ttttcttact gtgaaaataa agttactact tttagtaaat 123960 tatttttaagt tatttatata ttctggttac aagtcctttc tcagaatatt gtgaatattt 124020
tctcccagtc tgcggttttt tttgaagagc cagtattgtt aatttaatg aagccttatt 124080 tatcaagctt ttctcttaag gttcatgctt ttttgtatca taatagaaaa tcttttacgt 124140
accctaggtt atgaatgttt ttatggttag gtatatggtt gatttcaggt taggttttgt 124200
gtagggtgtg atgtaaaggt ctagcttcat tttctccacc ataaatattt actcggtttc 124260
tctggcacca gcctcgtttt tccattggtg gctttatttt ttttctgttc ttgaaacaag 124320
agtctcgatc ttgttacca ggctggagtg cagtagtgtg accttggctc actgcaacct 124380
ccacttccca gggtcaagcg attctgcctc agcctctcga gtagctagga ttacaggtgc 124440
ccgccactac acccagctaa tttgtatttt tttttttttt tttttagta gagacagggt 124500 ctcaccatgt tggccaggct agtctcgaac tcctgacctc aggtgatctg ctcatctcag 124560
```

```
cctcccaaag ttctgggatt acaggcatga gccactgcgc ccagccatag tagctttatt   124620
gaattcagtt gactgtattg tatgtgtgtc tatttgtgaa ctgttttgtt gtattgatct   124680
ttgtatatat ccttatgcca attctctctt tattgctgtt actttgtaac caacctttaa   124740
gttcatatga gtctcccagt tttattctcg tcaaaattac tcttattctg cgttctttga   124800
atttgcaaat aaattttaga atcagcttgg gattgtgcac tgaatcttta tatcagttct   124860
gggagaaata tcttaacaat atggaatctt cattgaggtc atcatatact gctccattta   124920
tttaagtctt aagtttcacc agtgttttct agttttcttt gtatcagttt tgtgcctgct   124980
ttcttaaatt tatcccttaa tatttcatct gttttgtgct gttgtgagtt atatttttaaa  125040 aactttcaac gtttgtttat tcgtaaatag agatgcactt gattttttgaa tattgacctt   125100 gtgtcttgat gtgttggtaa acccactgtt tctggcagcc ctttaagact taaacataca   125160
atcatgatct aatcaccatg ttggtgtttt tgggtttttt tttttttgtct tattgtactg   125220 gtgcattact gaaaaaggca tgagattttg ccatgctccc attttaggg  gtgagacatt   125280 gtctttcact attaagcata cagttaggtg ttacttcagt tcctaatttg cagaggtggg   125340
tttgttttct ttttaatcat gaatggttgt tggattatgt tcaaatactt atcatctact   125400
aagtatatca tattgaccag gaacagtggc tcatacctgt aacctcagag ctttgggagg   125460
ccaaggcagg aggatcgctt gaggccagga gttcaagacc aacctgggtg atgtaggaaa   125520
accccatatc tacaaaacaa tttaaaaatt tgctgggtgt ggtggcacac acctgtagtc   125580
ctaactactt gagaggctga ggaaggagaa ttgcttgagc ccagtagttt aaagcagcag   125640
tgagctgtga ttgtaccact gtactccagc ctgggtgaca aaggagacc  ctgtatttaa   125700 agtgtgtgtg tatgcgtgcg catagatgga tagataataa tgtaattcca ttatggtcat   125760
acaaactgat atgaaatgcc attttatcat ataacaagtg tcttttttgtg gttgaatttg   125820 tttctggatt tttcactctg cttcactaat ctaataggac taccttctca tccactcact   125880
gccaacattg atttttttttt tcagattacc ttgaattttc tgtttatttt tccatatgaa   125940
ctctataatt aacttactac taaaaaaatc agttgccttt ttaaaaccaa ctgatcttta   126000
aaatatatct tggctgggcc cggtggcagg cacctgtaat tctagctact tgggagactg   126060
aggcagaaga attgcttgaa cccaggaggc ggaagttgta gttgagttga gattgcgcac   126120
ctgtactcca gcctgggtga cagagcaaga ttccctctta aaaaaaaaaa aaaaaaaag   126180 aaacagaaaa gataaatctt tttacaataa tttgttccaa ttagggtcca agtcaggctt   126240
gcaatttgga tttgtttata tgttgaagtc tttttttttt tttaattgtt tcatattgtg   126300
gtaacttttt ttttttttttt ttgagatgga atcttggctc tgtcacctag gctggagtac   126360
agtggcacaa tctcaactca ctgcaacctc cccctctggg gttcaagcaa ttctcctgcc   126420
tcagcctccc aagtagccca gcctttttt  tttgagacag agtctcgctc tgttgcccag   126480
gctggagtgc agtgatgcga tctcggctca ctgcaagctc cgcctcttgg gttcatgcca   126540
ttctcctgcc tcagcctcct gagtagctgg gactacattc gcccgccacc acacccggct   126600 aattttttttg tattttagt  agagacaggg tttcaccgtg ttagccagga tggtatcgat   126660
ctcctgacct cgtgatccgc ccgcctcggc ctcccaaagt gctgggatta caggtgtgag   126720
ccactgcgcc cggccttgta ttttaatag agatgggggtt tcaccatgtt ggccagcccg   126780
gtcttgaact cctgacctca aatgatccac ccgcctcggc ctcccaaagt gctgggatta   126840
caggtgtgag ccatcgctct cagccttgcg gtaacttttt attacgaatg tattgagaca   126900
ttaataacct aggccagtca tgtttcatcc ctacccattg tctcttaaaa gctttgagtc   126960
```

```
cactggatta ttctgaagca aattctagac attgcatcag tttatccacc aacattttag 127020
tgtgtatctt taagttggtt ttggttttgt tttttgtttt tgagatgggg tctggctttg 127080
ttgcccaggc ttggagtgca gtagtgcaat catagctcac tgctgctgcg aattcctggt 127140
ctcaaaggat cctccctcct cagcctctca agtaactgtg actacaggca catgccacct 127200
tgccagcttt tcttttcttg tcttgtcttt cttcttcttt gttttttttgt ttgttttttg 127260 ttttttttg agacagagtc tcaccatctt tctatcttgc ccaggctagt cctaaattcc 127320
agggcttaag ttatctttct acctcagcct cctaaagtgc taggattaca ggccagcact 127380
ttaggaggtg ctggatgagc catcacaccc agccaagtca taggtttttt tgtttgtttg 127440 tttttttgaga cagtgtctaa ctctgtcacc caagctggag tgcagtggca tgatttcagc 127500
tcagtgcagt ctctaccaat tgggcttagg tggtcctccc acctcaacct cccaagtagc 127560
tgggactaaa ggtgcgcgcc accatacctg gctaattttt gtatttttg tagagacagg 127620 gtttcgaatt cctgagctca agcagtctgc ctgccttgac tcccaaggtg ccaggattac 127680
aggcatgagc cactgcactc agccctcaca gttttaatta cagtttttcc cttagttttt 127740
gtcttgttca tatccagctt gtcttgtatt ttttcccac gatctgaatt ttgctgactg 127800
tatccctgtg ttgatattta aagtagactt ctgtcccctg taatctttgt aaactgatag 127860
taaataatga aggcttgatc agattgggtt tttttttttt ttcccaatg tttcacagat 127920 gtgtgtactt tcagtgagga gtcatgtaat cagtctttt cctgatagga gtagtcagtg 127980
agttcctaga tgttttatct atccaggaga taatatgtcc ctttagcgcc ttaatttttt 128040
tggtgtgttt tttagcagcc attgatgata attgtctagc ccaagatcag ttatttcctt 128100
aggggttgta aaatggtgac attctttttcc tttcatccct tcttcaatta ttgcctggaa 128160
tatttctata aagaaaaact ttcccatatc cagctgtttg gttaccctga ggtatagctt 128220
tcttaggaaa agtaatttaa aatgttaatc atttcccttt ttaaggcagt cttcaaaata 128280
atgagttggt tttctgttat cctccaaagg taaccagtga ggtggttttt ttgtcgttgg 128340
ttcttactat cagtataaac ttctggaatt tttttttttt ttttaatttt ttggagacaa 128400
ggtctggctc tgttacctag gctggagtgc agtgggatga tctgggcata ctgcagcctc 128460
aacttcccga gctaaggcaa tccccccacc tcagcctccc aagtagctgg gactacaggc 128520
aagcaccacc gtgcctggct taattttgt atattttgca gagacagggt ttcaccatgt 128580
tgcccaggct ggtgtcgaac tcctgagctc aagcagtctg cctgtgtcag cctcacaaag 128640
tggtgggact acaggcatga gccaccatgg caggccagaa tcacaataaa cttataaatt 128700
aacttgagaa gaaatgattg atgtcttcat gatgttgagt cttcctgttc aagaacaaag 128760
tataccttca atagcatatt aaagtttatc cttggctgga tgcagtggct gacgcctgta 128820
atcccacctc tttgggaggc agaggtgggc agatcacctg aggtctggag ttcgagacca 128880
gcctggccaa catggtgaaa ccccgtctct actaaaaata ttttaaaaaa agtattagct 128940
gggtgtggtg tgcacctgta gtcccagcta ctctggaggc tgaggtagga gaatcgcttg 129000
aacccaggag gcagagagtg cagtgagtca agattgcacc actgcactcc agcttgggca 129060
accgagcgac actctgtctc aaagaaaata aataataaa aataaagttt atctttaagg 129120
ttttgtacat tttttttcagt gtatgcctta ggtaggttct tttttaatgt tagtgtaacc 129180
cagggacttc tcttccattg catcttctaa gtaattactt atgaagtacc atatatgaag 129240
gctattgctg tttatatgtt agttttacc ctgctccttt actaaattcc aatcctttga 129300
```

```
ggtattggat aaaaatattt ttagcatttt tcaaataaca ggcagagtca agggcttggt   129360 ttctttctt  ccctcctgt  ccctaccct  cccttttt   gagacagggt ctcacttctt   129420
cgccgaggct ggagtgcagt ggtgcagtta cggcttaccg cggcatctgc ctccctggct   129480
gaaaagttcc tcccacctca gcctcctgag tagctgggac catagatgca cagcaccgca   129540
gctggctaat attttttgtat ttttttgtgga ggcagtgtct ccccatgttg cccagggtgg  129600
tcccaaactc atgagctcaa gcagtccgct cgccctggcc tcctaaagtg tagggattat   129660
aagcgtgagc cactgcgcct ggcctgggga tcatgtttta acatgagaat tagtggagac   129720
aaacacatga tatctaaata atagcaccat agtatacttg actagctttt taattatttt   129780
ttaaatatac aggaaggtaa taagtaacaa agtaataata gtgaatagtt taagctcagt   129840
tagcataatc gggcaaactt tcatttgata aaagtgataa gtagttttca gtggcttttt   129900
tgtttaccag aaggaggtgg tttttaaata cgtgcatcca agataaaata taaaaaaatg   129960
ttcaggtttg ctttcctaca tagataaaat aatatgtaac tagctctccc aaatttcagc   130020
aacagttagt gaatgtttag ccacaaattt gcagttaatt atataatcag ttcttaggat   130080
tttatgaaca agttctatat tctttgtgcc ttatacctag ttgtaagcag tcattccaca   130140
attattttcc tgaagtggct tggttaatgc cacaccagaa acaggtcaca gacaatagtg   130200
ctgtaagaaa tgtgtgagga aagaggcaca tgggaagtag ctagctcgtg ctggaggaac   130260
tggaaaaaaa cctcacatgg gagatgacag ttgagctgaa ttcttaacta gagttgtaac   130320
agggcgaggc ccttacatgc agaccacctg tgtggattaa gataagacat aaagtaatct   130380
tttaaaagaa ctattattta gaaacctggt atatgctaca tggtgctgtg ttatactggg   130440
tttgagaaag aatgggaagt gttacaagga ttcagtggtt ggaaattaag gaagatagaa   130500
agttagtgtt ggatctgttt tggctctttg gtcatgcctt tgttttctc aaaatgaatg    130560 cagtgcccgt cccagaaaat accatatgag aagcgatttc ataatgctgt gagagtctgt   130620
tacagggact tgatcaagtc tgagggccat gagagaaagt ccctctgagg aagttgcttt   130680
caagctgaca cctgaaggat gaagcagaat tatcccagct gggatttggg aactggtgtt   130740
tgaggctgag gactagcatg catgatagga aaataaccca gagtggcaga agtgggagtg   130800
gtatgagatg gcatcagaga cgcagattca gggtcaaatc attcagagcc tcctagacca   130860
tgtgaacaca tgtattatgc tgtggagata ctgtttaata ggcagtctgc ttttttttct   130920
gcagtaccaa atatgcccca acagcggcaa gaccagcatc atcagagtgc catgatgcac   130980
ccagcgtcag cagcgggccc accgattgca gccacccac  cagcttactc cacgcaatat    131040
gttgcctaca gtcctcagca gttcccaaat cagcccttg  ttcagcatgt gccacattat    131100
cagtctcagg taaggctggt aaggcctaac tcttaatttt tgtaccatat aaaaaaactt   131160
ttaatatggt aaagggattt tcctttataa tttttgcttt tgtgtgatgg tagggtagat   131220
agctaaggac ttggggaccc ttttcaatat atattcgaag gttactgatg attgtaagag   131280
gttcagagga aacagccaag aaagatttga gagtttacag ctgtttctgg aaatctggaa   131340
accatggagt taaaaatctt aactaaagtc tgcttggctc tatttgcagt gttaatgtgc   131400
tttctttatt ttttgtttga acacagcatc ctcatgtcta tagtcctgta atacagggta   131460
atgctagaat gatggcacca ccaacacacg cccagcctgg tttagtatct tcttcagcaa   131520
ctcagtacgg ggctcatgag cagacgcatg cgatgtatgg taggaagcac tttgtttgtc   131580
tcttccagtg tgtgtgactc ttcttaattt aagtttctga aaacatactc tatctaagaa   131640
taacctgacc ttttatgaca ttgagggtca agaatctgaa ggaaaagatg aacccatttc   131700
```

```
tttgcctgac ttgctttata acttttggca aatagtttct acttctgtac ctggtcttca   131760
gatctctttc ctgctttaac taaaatgtaa tgatgtatat aatggcaaag catctttgtg   131820
gagaaaggta cctttctcct cttcctcatc aatattatgc tttggtatat cctgcctacg   131880
acatgcaaga gaattttata ataataaaag cataaaggtg ttctccagca tgaaaacatt   131940
ttgcttcact acttgatctg agggtcactg gcattacata ttttttttgc tgtttgttat   132000
aatgataata ctatgtttct acatcatgct gtattttaat ggttgaatat tatgtcatat   132060
tagatatatt ttagacatga gtcacacttt aaatataacc aatgtgaaca gaatgctgaa   132120
atgaaaatga gaagtatttt atgtaaaact aagcagtatt tatatgtgag aataataagc   132180 aaaaaaccc atcttcgttt tgtgactaaa cagagaaatt tgtgtagatc aacttagcag    132240
ctgtctaaag taccaaaata atagatttt cactgttgat aatttaaaat aaaatgtcca    132300
tttgtatatc ttatgataca gaattaatgg attgcttcaa atgttttca gaatatgttt    132360 ttaaatagta ctgatttcat taagatgttt tgttctgaat atttctgaga actaccgtag   132420
tgtcgtttag ttttcctatt tgcgtttttg gttgtttgga gtaggggata attttggttt   132480
attcatacag ttgaaaagtg tactgctatg agaatgagat tatggttaca tgtaactaca   132540
tgggcatttc atttttaaag cctctttgaa cttttgaaa tactaagaat ataaatttt     132600 tatttttaa gtttagatgt cctgaacgag tatgttagg caaaattgag ttatttaaga    132660
atttataggc tgggcgcagt ggctcacgcc tgtaatccca gcactttggg aggccaaggc   132720
tggcggatca tgaggtcagg agatcgagac cagcctggcc aacatggtga acccccatct   132780
ctactaaaaa tccaaaaaat tggccgggtg tggtggcatg tgcctgtagt cccggctact   132840
tcggaggctg aggcaacaga attgcttgaa cccgggaggc agaggttgca gtgagccgag   132900
atcgcgccac tacactctag cctgagcgac agagtgagac tccatctcca aaaaaaaaa   132960 aaaaaaaaaa gaatttacag atttctggca aaccttcttc ttgagacatt actacttttc   133020
ataccacctc tgtcctttt gaagaataaa agttttaaca ttccgtaggt taatgagaat   133080
aggacttggg cagcagcaat catccttcct gtcacctgta acccacagct tatgctttct   133140
tcctggaggt tcttgtctgc cacaaaggct cactgctgat aggaatttgt atatgatcaa   133200
aggtgtttag ttttataaaa cagttaagtc cagtcttaat tttccacatt atcactttca   133260
attttgtatt gtggattacg catttaaat aaaaaattgt gtgattgcta cattttggaa    133320 aacattttt tcaagaggcc catccgtaat ttaattgtaa aagatactga caaactaact   133380
tggtttatta ttttggttat gaccccgtca tttgacttgt ctttagttgt cttaacgggg   133440
actgaatatg cgtgcaaagg cacgattgat ttatcatgct ggcttttatg caacttgtat   133500
atattttaac aatttttcctg tttgctaaag gcttaggtta aaagttcatt atgattgttt   133560
atacatttct ggtgaataca tcatgattta acaagtggaa agaacatctc tttccttcca   133620
ttttctggca tactcccctt ggaatcagat ctgaaacttt taagctaaaa tttccattgc   133680
atttggagag tagttatttg tgtatgcatg cttttgagac attgtagcaa taatactgta   133740
atgttgagcc gaatcttct cctcattgtg ttcattcact gccaacatct ggcttcatct   133800 tttgatgaa tgttcattgg ttttgaaaca gcctataggg taaatactgt gtttgaggta   133860
cagatgattt tcataactac ttcctagaac atgtccattt gaagagcagt ggggccttag   133920
accccaaagt ccatttatgt gtgggcaaat aggaaatgtt gcaaacaaaa caaagcacta   133980
gatctaatgt ccagtgaaat ctggaatgaa ctagtcatta gagccggttc tttcatgcca   134040
```

```
ggaaaaagtt actcagccaa atctgaacta ctctcctgca gtttacacag gtggtattta    134100
attgctgtct gtatggaggc aggctaggag caaggctgtg gacttgttgt gattgtcact    134160
agttaatcaa gattcccttt gtggtgctta agaccctaaa aaggacacta ggagctgggc    134220
atggtggctg acacctgtaa tccaagaact tggggaggct gaagtggagg atcgcttagc    134280
ccaggtgttc aagaccagtc taggcaagat ggcgagatcc catctctacc aaaaaaaaaa    134340
aaaaaaaaaa aaaaaaaaag cccagtcatg gtggcacatg cctgtagtcc cacctacaca    134400
ggaagctgag atgggaggat cacttgagtc caggactttg aggctacagt gagctatcat    134460
ggcaccactg taatccagcc tgggtgacag agcaagaccc tgtctctatt taaaaaaaag    134520
aaaacataag aaagaattgt tttgttctat gccatcataa gccataattt aatctgctta    134580
agcatgttct tcattaaatc tgcagtgatt tatttgaatt attagacttt caaagcctta    134640
ttatatcaaa tataaacaaa atttgaagta cattcttata aactacaaca aacttacata    134700
gaagtgttaa ttttatactc atcttccctg aacaatttat attttataaa tatattaaat    134760
atattgtaat aaatttctc aaaggaacca atactttga gtatgaattg tgcttttctt    134820
tttaagctac atcatatcta ggttttaaa acatttaatg caaacagaag aacatgcacc    134880
cagatgttgg tgacaatttt atgtcacctt ttctcattca ttaattgtta tagccatagc    134940
caaaggcatt gaaaacatag gaccactaat gactgcaaaa tgaaatcctg attattgttt    135000
ttaaattttt agtatgttta atacacatat gctaacatta ctgaacagtt aaatgataaa    135060
ataggataat tattttattc taaaaaagta ttgaccttga cctctttcta gctatcttag    135120
aaagggcttt tgtcaaaaac cttatctctt tgatgtctct ttttttgaga tggagtctct    135180
ccctgtcgcc caggctggag tgcagtggcg tgatctcagc tcactgcacg ctccgcctcc    135240
tgcgttcacg ccattctcct acctcagcct cccgagtagc taggactaca ggcgcccgcc    135300
accatgcccg gctaattttt tgtatttgt ttagtagaga tggggtttca ctgtgttagc    135360
caggatggtc ttgatctcct gacctcgtga tccgcctgcc tcagcctccc aaagtgctgg    135420
gattacaggc gtgagccact gtgcccagcc tcttttttt tttttatttt ttatttattt    135480 tttattttt ttttaatttt tgagaaggag tctccctctg ccacccaggc tggagtgcag    135540
tggcgcgatc tcagctccct gcaaactccg cctcctgggt tcaagcagtt ctcctgcctc    135600
agcctcctga gtagctggga ctacaggtgc ccgccaccac acctggctaa ttttgtgtt    135660 tttagtagag acagggtttc accatgttgg tcaggctggt cttgaattcc cgacctcagg    135720
tgatccaccc acctcagcct cccaaagtgc tgggattaca ggcgtgagcc actgccccgg    135780
cctctttgat gtctcttaat ctaacttcca tcattgcctc tacccatcc cttctaagaa    135840 gttactttaa tttttttcc tctcacatct actctttttt ttttttttt tttttttg    135900 aggtagtctc actctgtcac ccattctgaa gtgcagcggt gcgatctcag ctcactgcaa    135960
catctgcctc ccaggttcaa gcggttttc tgcctcagcc tcccgagtag gtgggactac    136020
aggtgtgcgc caccacgacc ggccaatttt tgtattttta gtagagacgg ggtttcaccg    136080
tcttggccag gctgatctcg aacttctgac cttgtgattt gtctgcctag gcctcccaaa    136140
gtgctgggat tacagatgtg agccaccacg cccagcctca catctactct tctaatccat    136200
ctaattttgt tttatggtga tgcttttacc tttcagaaac agtaataata caacttttcc    136260
gactaactag agccattagg aagaattaga tccagaatcc ttttttgatt tgttttggt    136320 agtttaatgc agataagtaa gaaaatatag ttaagttaaa aaaaaaaaaa atgaaaagca    136380
tccataatcc ctccacctga caactgcctt ttaacatttt gatgtgtatc cttccaggtg    136440
```

```
tatttaaata cactcaaata ccctacccct ttatgtagac atgttttaat aagaaataat   136500
attcatgttt atattcttgc tatgatccta aattttgga tccattacta gataatcttt   136560
caggataatg acatttccat tagtaatgtt tttgcaaaat tgtgtgtcta ttgaattaaa   136620
cttgtaaaat agttttattt tggtacatga tttatatcaa ggttgttcag tagaatgcca   136680
tgttggtgtt tttattagat aatgatttta ttccttttac ttttaagcaa gtcagcatga   136740
caacttgaca cctaagtaca gaagaacagt gtcttccggt ttagtccttt cttttaaaat   136800
tctgtagcag tgtttaaagt gcttgtcatc tcttatgaaa atgaattatg catgaataca   136860
aaagaaatt actaatatgt caacctttcc agaaaatttg gaaaatgcac acctcaaaag    136920
gctaatttac ctttctattt cccaaattca gcatgtccca aattaccata caacaaggag   136980
acaagccctt ctttctactt tgccagtgag ttgggttttt tatactaatt tttaattgta   137040
cagtaaaaca ctttttaaag gatacatgtt aagggagtag acttgttgaa caatattttc   137100
cttgtgccag tcaaattatt gaaagtactt atatatataa ataattcagt ttttaaaatg   137160
gaaataccca atttaagaag gctggagtta atgaaaaatg gagttgtttc agaaatcaat   137220
ttttgcatac caagcaaatg tgactgggaa atgcctaata ttttccttgt tagagaaact   137280
tcctaaacag ctttatacac acacacacac acacacacac acacacacac aaacacacac   137340
acccaagcca caagcttggt ataaatttaa aatgtttatt tatacacaca cacacacaca   137400
cacacacaca cacacacacc ccaagccaca agcttggtat aaacttaaaa tgtttattta   137460
tattctgata agatgaaatt tatgcctacc aggattttta attgaatagg attgatgaaa   137520
tactaaggga aaaactttc agtcctgtgc atggctaaag gtttaaaata ctcaggaagg    137580
gccaggcacg gtggctcaca cctgtaatcc cagtgctttg ggaggctgag gcgggtggat   137640
catctgaggt cagcagttca agaccagcct agccaacatg gtaaaactcc atctctacta   137700
aaaaatacaa aaatcagcca tgcatgctgg catgcgccta aatctcagc tactaggag     137760
gctgagacag gagaattgct tgaacttggg aggcagaggt tgcagtgagc cgaagtcgtg   137820
ccactccact ccagcctggg tggcagagcg aaattctgtc tcaaaaaata aaatattcag   137880
gaagcagacc cctcaggata tcttgagctt aagcaagaga tcatgacctc tcaggtcatt   137940
atcttggaca gcacaggtcc cctctcccca cctggcaaaa agtacagaaa tagttgctcc   138000
ttcatggaga aagtctgggc agagcttct tctggaaatg aacttttaag gtacattttt     138060
cctatttgta gggcaatttg taaaaataag ggccggacgt ggtggctcac gcctgtaatc   138120
ccagtacttt gggaggccga ggtgggtgga ttgcttgagg ccaggagttc gagaacagcc   138180
tggccaacat ggtgaaaccc tatctctacc aaagcatggt ggcacgcacc tgtagtccca   138240
gctacttggg aggcggaggc acaagagttc atgaaccct ggaggtggag gttgcagtga    138300
gctgagattg taccactgca ctcaggcctg gcaacagag agagactctg tctcaaaata    138360
aaaaataaaa ataaggctag tcttggactt tggtatttaa ataggaagga gtactaatat   138420
ttgtagaaat cctttagaaa tttgtgccat taatattgtc accttgtatg aaatgttgtg   138480
ttctagagga tattaaggat tcaaatttta tgttaggcac attttgagtt attttggggt   138540
gactcaatgt ctgactctac taaatgccat attagcattt aaaatgcatt tgaccttaaa   138600
tctttgttaa ttatgccatg acttggtatc caaaaataag ctgatacata catacataca   138660
tatatgtgtg tgtgtgtgtg tgtgtgtgta tatatatata tatgtatgtg tgtatatata   138720
atttatttgg tgctaggaaa tgttaaattt aatcctttaa tagatgctct ttaaaaagga   138780
```

```
gtcttgctgt atgtatatac tattaaaggg gaaactatgt ctgtgattgt agtgtgtaaa   138840
agatagtagg tgattttatt atgtactcaa tttgaggtct caaatgtagt tatcctcacc   138900
atcttactgt ctctgttagt agtttggtgt tgttttcctg gtaagtagct aaggtcctta   138960
atcattaaca cctaagcctt aattgcctta gcacaacttc ccctaaaagg gagtatcagt   139020
acttttttaaa agaaactaac agttgggctg ctaatttaat ctgctgcttc atttccccct   139080
gttctaagcc attttatgat ggtttggtca agttgccttt tattcccctt ttagagtttt   139140
caactttcct tcacttccct ttttctgaat ttaacatcag atttacaagt tggaagattt   139200
tgttttgttt tataagtttt gcaatgctgg tgatctctta tgacttgtgc atccaaagtc   139260
aaaatgacaa aacctagtta caaattaaac acacagcttt ctgtacttaa tttgcttcag   139320
tgagatcaca gctgaggaaa ctagttctgg aatgtggtta gtgttattaa ggattttga   139380
ctgatcatat gtttagaatc ttaaatattt atgtcaagga acactgagtg ggaaacttct   139440
ggactaggtc tggaccaaag aagcatatgt ctttgattat ctttaatcta aaagattta   139500
tgaagactaa agttttataa atagaagttt aactgatgaa taaatcagta ttacaaataa   139560
aattaacttt attttaacc tctctgggat ctttagccag aatgagcata tataacaaaa   139620
gcagtgaaat aatatgtgtg ggtcagaacc cactgcccct cccactccac tctccttttc   139680
cctgattctc ctgtgttttt tccttcttta ccttatcttg gttccttttt tttttttttt   139740
cttttgagat ggagtctcac tctgtcgtcc aggctggagt gcagtggtgc gatctcggct   139800
cactgcaacc tccgcctcct aggttcaagc aattctctgc ctcagcttcc agagtagctg   139860
ggattacagg cgcctgctgc cacacccagc tatttttttt tgtatttta gtagagacag   139920
ggtttcacca tcttggccag gctggtcttg aactcctgac ctcgtgatca cctacctcgg   139980
cccctggttc cttttttgtc tctcttgtct tccaagctat ttttttcctt ggcttttaaa   140040
ttttcttcct accctgcttt gtgtcactgt cacttaactg gcctatcaag gaaccgaact   140100
gtatttttgt tactagtatt gatttaaagt ataagtttca catttctccc aatttattat   140160
tattatttat ttatttattt gtttatttta ttttttgaga cggagtttcg ctcttgttgc   140220
ccaagctgga gtgcaatggt gtgatgtcgg ttcactgcaa cctccacctc ccgggttcaa   140280
gctattctcc ttccccactc tccctagtag ctgtgattac aggtgcctgc caccacgccc   140340
agctaatttt tgtattttta gtagagacag ggtttcgccg tgttggccaa gctggtctcg   140400
aactcctaac ctcaggtgat ccgcccgcct cggcctccca aaatgctggg attacaagcg   140460
tgagccaccg tgcccggctc catttctccc aatttcaaat tcaaggagga aaagaattcc   140520
tgattaaggt acttctttca gatcttttga gctagaacaa aaaaacaaag ggaaatattt   140580
ctaattaact cttttttaaat tttgtttaca acgtatgata catattttac acatcctttg   140640
tggtttttgt tcgtcttgtt tttaatcaat gccttgcaag tttaccggta tttaggtagg   140700
gaaaggattt tgtttttgtt tttttaaaca aagccctatgt acattcactc agcttgggta   140760
tttgtgctat gcatgcaaat tagctataga ttagaaaacc gtattatagt ctttaaatac   140820
tggtaaactt aaattgcaga gatgcctttt aaaaatgcat agtaaaaata tttcatcttt   140880
acttttctct tcaaatgatt ttaagatttt tacattttc cagttgatga ataacttaaa   140940
ttatgagatt tcatgggcat aattattttc tatatttatt gttacttttt aatattctta   141000
atactttgct tagaaggtat ttaaaagtga aatttcaaac ttttttagtac aaaatttctt   141060
gaataaataa agttacaaaa aaaaaacaaa aacctctgag attccgtact gtatcttttat   141120
gaacctccat gaacagaatt tgggatttgg gaattgcttt tccttagaca gatttagatt   141180
```

```
gttacaaatg acatttttaa gaggctgggg tggcggtagg ggttagtgct aatggtttaa    141240
cagtagggga ccatggacaa ctgtagacat cactatccag tagaacattt tgtggctggg    141300
cgcggtggct cacgcctgta gtcccagcac tttgggaggc caagacaagt ggatcacctg    141360
aggtcaggag ttcaagacca gccagaccaa catggtgaaa ccctgtctct actaaaaata    141420
caaaaaagtt agccaggcgc gcctgtagtc ctagctactc aggaggctga cacaggagaa    141480
tcgcttgaac ccgggaggca gaggttgcgg tgagctgata tcacgccact gcactccacc    141540
ctgggcaaca gagcgagact ccgtctcaaa acaacaacaa aactgcactg tccaccgtat    141600
tagctactta gctacatgtg gcttttttat tattcaaaaa taaattttta ggccgggtgc    141660
agttgctcac acctgtaatc ccaacacttt gggaggccga gatggacgga tcacttgagg    141720
ccaggagttt gagaccagcc tggccaacat ggtgaaaccc cgtctctact aaaaatacaa    141780
aaattagcca ggtaatccca gctactcaga ggctgaagca ggagtatcac tttaacccag    141840
gaggcggagg ctgcagtgag ccgagatcgc tccactgcac tccagcctgg gtgacagcaa    141900
gactgggtct caaaaataaa caaacatggc cgggcgcagt ggctcatgcc tgtaatccca    141960
gcactttggg aggccgaggc ggatggatca cttgaggcca gtagttcgag accagcctgg    142020
ccaacatggt gaaacccgtc tctactaaaa atacaaaaat cagccaggca tggtgatgct    142080
tgcctatagt tccagctact cggcaggctg aggcaggaga tcgcttgaa cccgggaggc    142140 ggaggttgca gtgagccgag atggtgcccc tgcactccag cctgggcaac agagcgagac    142200
tctgtcaaaa attaaacaaa taatacatt tttaaaatga acgtaagatt ttacaagta    142260 caacaaactc aggttcgaaa tttacatcaa atctttaga ccaagtcagt gcctatacaa    142320
cttggaggag ctggaagtaa acttaatgag tatgatgatg atggagggcc tgttaataag    142380
ccaccaagtt agaaaaaaag gactgtctta tagacttatg ggactgtgaa gctcaggaag    142440
gcttcatcgt ttgtacatca tttgttctag ctcccagaag acgttcacta ctcttaaaaa    142500
cattcagaga ctatgttgcc acagtttct tgttaaaata ttctggcata tgttaattcc    142560
tacagtctgg aaaatttcc cagtgtataa acaaagctgc tgtatccagt ctaaactgga    142620
tatgaaggaa tattaatgcc agctgtggca ttggcagtgg atgcacaggt gatcctagaa    142680
ctggctcttt gccttgccct ttccctgct aagagatagc tttgcagctg gagacgtaac    142740
tgttagggct ggagagttgg tggcccttag ccctacaaca cctaggatta tagaactgct    142800
ccatgtgcct agcctaaccc tctgcacacc atttacgtgg aatatacca gagccgtcta    142860 tgctggtgac tcggcagcct tgcctaccag actgctggaa ctagggtgcc tcttcccaaa    142920
gctgtgcttg cttctctcac caatcagtcc tgcatatgtc tgtgtttgct aacacgttat    142980
atgaagaatg tggggaacta ttttggaatc attctgtgt atggcttat tatcttgagg    143040 gattttagga tttgtttctc aagagagggc tgggaactat accttgctag agttgtcttg    143100
agaacgctct attctcagct cattgcctcg tggaggttaa ttttttatca tcggtgtgct    143160
gtccatagtc actggaagca gtgaacacat cctactctgc ttctgattct caacttactg    143220
tttttgaagc acatgaacag gccaggcacg gtggctcacg tctgtaatcc cagcactttg    143280
ggaggctgaa gtgggcggat catttgaggt caggagtttg agatcagcct ggccagcatg    143340
gcgaaacccc atctctacta aaaatacaaa aattagctgg gcgtggtggc acatgcctgt    143400
aatctcagct actcgggagg ctgaggcagg agaattgctt gaacctggga ggcagaggtt    143460
gcagtgagcc tgggcaacag agtgagtgag acttatatct caaaaaaaaa caaaaacaa    143520
```

```
aaaactgaaa gacatgaaga aatggttttt gtaccaaggt ttggcccacg ctgagattca    143580
caaagaactg gctttcagtt cttatcttta ttttgattta aactggccca tcatgttgtc    143640 cttttgaagtt agtctagtaa atttctttcc aaagggctgg ggcactcaga agggagttta   143700
cttttctata tttatttcat aaagcaaaga tgggagatcc tccattaggg cttgggaaag    143760
taaactgagt ggcagaaggg ctcctgtgat tagctgagag agactgtggt ccttcggccc    143820
tgatgataga tccctggcct tgccacatac catacacagt gcccgcaccc ccatccccca    143880
ccacacccaa tatagtctgt gccctcagga cattgctcca gggcagtagc atggtgaggt    143940
tagcctgatg atggccttga gctaaagagt gtgcacctaa aatgcacttg tttgagtagt    144000
ttctgcctat gccttcaagt tgccttttg ggaaaaccta gtgaccgtta agagtaaatg      144060
caaactaatt tgattttaat atcatatgta gagctgtatt atatgaacca aatgctagtc    144120
tgttaagcaa tagctacact tatttttca agacaatgga tggtttaaat ggagtcatct     144180
atagaaattg gtagtggcgt gagttatgca ttgtaaccat caagaaagtt cagttgatga    144240
agtgtagagg agcgatggag gttgtcagac atcggttgtg tacatgctcc ttttctttc     144300 actttagttt ccacgggctc ccttgctcag cagtatgcgc accctaacgc taccctgcac    144360
ccacatactc cacaccctca gccttcagct accccactg gacagcagca aagccaacat     144420
ggtggaagtc atcctgcacc cagtcctgtt caggtaaggg caactcagag gtctgcatgg    144480
agtggcttct ttatcctagt atctgagtgc tttcttcagg tgccaggtat cgcatcgtca    144540
gaacacatgg catgtccacc ctcgtgaaga tggatacagc tgtgcccctg gggtggtggt    144600
tttaagaatc acatttaaag gctgggcgca gtggctcacg cctgtaatcc caccactttg    144660
ggaggccgag gcgggtggat cacgaggtca ggagattgag accatcctgg cgaacactgt    144720
gaaactccgt ctctaataaa aatacaaaaa aattagccgg gcgtggtggt gggcgcctgt    144780
agtcccagct tctcgggagg ctgaggaagg agaatggcgt gaacccggga ggcggagctt    144840
gcagtgagca gagatcgcgc cactgcactc cagcttggac aacagcgaga ctctgtctca    144900
aaaaaataaa aaattaaaaa aaatcacatt taagatacat gttgataata aggtgattgg    144960
ataagctctg gaaacttgca gtaatgaaaa atcaaattta acataaagtt cataaggcaa    145020
attcctattt gcttgggact ttttaatttc taaggtttat gtgatgaggt tattttccta    145080
tgagcttctt gaattatgtt tgctaatgga ggcagttaaa gatgtctttg atatctatca    145140
gttccctggg gcagtagtct ttttgactt tagtatgtat gctcagaagt ttctaactgc     145200
cagactgaga atcaggcttc tgtaccctag aaaggagttg tccagatggg aggcacctcc    145260
agccttgctc ttaccaccct gtacattctc ctgtactttc cagtgaccct catcataggc    145320
ccaagtgtgc aaagcttagc tttgtgggta tcccttggct gcttttcatt aaagaagttt    145380
tcctctcaat tctttcctgt cgctttgcag caccatcagc accaggccgc ccaggctctc    145440
catctggcca gtccacagca gcagtcagcc atttaccacg cggggcttgc gccaactcca    145500
ccctccatga cacctgcctc caacacgcag tcgccacaga atagtttccc agcagcacaa    145560
cagactgtct ttacgatcca tccttctcac gttcagccgg cgtataccaa cccacccac    145620 atggcccacg tacctcaggt aataccagct ttagccaact ttctgtgaag gccaagtaga    145680
atgtgaaggt tatcagtaag cagctagagg ctctcccagc taggaaaccc tgtgtgtcat    145740
gccatttgcc tgtctccctt tccctctcaa atacacgtga tctggcccta agggaatgtt    145800
tgtgtggttt tgtcatggga tcagtgaagg tgctgattgg tcagtccttt agttttccaa    145860
ctgagacctt aaaaatatct ttgactctgg aatgcaaccc agtccttctt tcctttctgt    145920
```

```
gtctgctttg ctatgtctat atagcctcac tactatatat atgtgtacat atatattccc  145980
ctacacactt accttggaag ccaggcaggg atgatggcct tcacagagtc tcagctctct  146040
gaagtgacta ccggggcctg tcaacttgat tgttactcac atgagttcca gacacatctc  146100
tccaattgtt ttccctggtt atccatatat ctgctttgac cataagttgt actcttgaga  146160
gggcttggcc ttggacattg gtgcagtgta actagaagct ggaagcaccc aggtggtccc  146220
attttctttt aagagcagcc ctggaagcac tttggagctc acctccagtg taagctgcta  146280
caggtgaaag gtgtgcttgc catctcagtg gttgctgtct gcatcagctg ctgacaaagg  146340
tccctgcact ccagggccca ggggattgtc ttaatgagga gaaggagctg cactgaagtt  146400
gggctctaac gctggccttg aggccctccc tggggctgtt acgggtgaat tggctgtatt  146460
agatgtctct gctactttca taacagaact ctctgaggcg gtctaagtg agacctgcca  146520 caatgaattc catttcctgt taaatagtgc gccagtgagg ctctggcaag gtgtgggcta  146580
gagatgcgac tcagttggat ctatctctca gaaggctacc ttgtaagtag agttccacag  146640
ctctgggaag tttgggcgtc ctcaccctgc aaagtttagg ttctgtggtg tagcgcactg  146700
cagttgattt gcttttttgat agtggggagg gaagccggtt tggtccgtgt gggccagcgt  146760
ggtttggtgg agtcagcttc ataagagctg gggtcctgta ggtgtctacc agaggctggt  146820
ggctaagtag gcatgtgaac ttacatgtaa gtcaggatc cctaaaacct cactctgttt  146880
ttgtgctgaa agggcaaaaa ggttaacaca gggaagctca aatttgccat gtgcccgttt  146940
gaatatgtga gagtaaaaac ggcatttcat ccaaggctta tcgtagtcta aacagtgca  147000 cagtgtggga aaaggaaac aagggctctt cctggccctg ccaaccccct gcagagctgg  147060
aatccagctg tttgggctga ctaaaatcac ctttccaact tgacagtgag tgagaccagg  147120
ttgaacttgg tacagagacg ctgggctggc ccagatgact tcaggttact cctttccatc  147180
tcactggagc cattaaaaac tccaactcct cctcctcctc ctgctccatc agcatatctc  147240
tgagagagtc acgggggcct aagagtctct tttcactgcc tggtgagcag accagaagca  147300
gagggagaga ggcaaatgaa cagaggtcca agtaattcac atacttgact gtgcagtct  147360 ctgcttatta atgtaatctg ttttcctatt tgaaagggat gttatctgca aaactacctc  147420
aggccccaca tggcagcctg attctgaagc atcattgaat cttgtatgat attaagttga  147480
gaaagctgcc cttggatcca gtgtctaatc tttgtgaaga tcttacccca tacatagaat  147540
acaatgatca gaaatgtcaa gggttaggac agcacagccc tgacttctac ccaggctcac  147600
ttgttgcctg ctccctgacc cttgcaggat ctgcccaaag gtgaagcgcg tcttcaggtc  147660
aatagataat ctactagaga ttgtccccag agaacagaac tgggccctga ggcccaccgt  147720 tgcccttttcc tgagagtccc agcccagtga aggaacaca gttgacatgt tgttgaagcc  147780
ggagatgttg cctgtatgcg taaaagagct ctctgtttca ggctcatgta cagtcaggaa  147840
tggttccttc tcatccaact gcccatgcgc caatgatgct aatgacgaca cagccacccg  147900
gcggtcccca ggccgccctc gctcaaagtg cactacagcc cattccagtc tcgacaacag  147960
cgcatttccc ctatatgacg cacccttcag gtgaggcgtg tgtgtgcagg ggccgccggg  148020
gcaccccaaa gcattctgct cgcacaggtg gaatggcagg cagggccagt gcttcaagcc  148080
ccgcatttga gaactagcaa gacccgtcca ggagtgtgca caggagggac tgtgacgatc  148140
agttcagcat cagggcctga ggcttccggg agccgagtct gtgtgtgttc tgatggtata  148200
caggatttgg cttgatgaga agcagcagca gcagcaacag cagcctgatg catgcctagg  148260
```

```
actcagttgg ccttccttgt tatgacaggc tggacagggc agtgttttcc ttcctgagtc    148320
ccaaaagtct gacatgtggg gggttattac catggcagag tttgattgta gctctggaga    148380
agatactgct gagaaagcgc tgtggatgga ctggctttga gtgtagcgtt agccccagcc    148440
cctgaacagg ggagagcgcc ctgtgattgt gctctactac ttgatggctg ccatggcgat    148500
acttcacagt ctgacctgtt attctgaaag caatactggt gcttggctaa tatttgggga    148560
gggggtttgt taaggccttt ttttctaccc catgaacaag tcttctggga gttttatctg    148620
aagtggtttt acgtctgact ggtttgtttc tacccaccca cccaaccctc cccactttgg    148680
tgcagatggg aggggaaaa gcgaattcaa ttttgagttt tgttcagcta gcacgaggat    148740
agtttacaat catgtgctgc agagacacta ggctgatgtg tggtgttgcc agttttctgt    148800
ttcaatgttc gcttttcttt ttacagtaca agcccaccac caacagcagt tgtaaggctg    148860
ccctggagga accgaaaggc caaattccct cctcccttct actgcttcta ccaactggaa    148920
gcacagaaaa ctagaatttc atttattttg tttttaaaat atatatgttg atttcttgta    148980
acatccaata ggaatgctaa cagttcactt gcagtggaag atacttggac cgagtagagg    149040
catttaggaa cttgggggct attccataat tccatatgct gtttcagagt cccgcaggta    149100
ccccagctct gcttgccgaa actggaagtt atttattttt taataaccct tgaaagtcat    149160
gaacacatca gctagcaaaa gaagtaacaa gagtgattct tgctgctatt actgctaaaa    149220
aaaaaaaaaa aaaaaaatca agacttggaa cgcccttta ctaaacttga caaagtttca    149280
gtaaattctt accgtcaaac tgacggatta ttatttataa atcaagtttg atgaggtgat    149340
cactgtctac agtggttcaa cttttaagtt aagggaaaaa cttttacttt gtagataata    149400
taaaataaaa acttaaaaaa aatttaaaaa ataaaaaaag ttttaaaaac tgatcaagtt    149460
agtgtgtgtc tgtataagct acttctttgt aggatactta atatcaaagc aggtgtgcta    149520
agggtgcatt ttgaatatcc cggaaggtag ctgtgaaatg atttttcttc ttcacccctta   149580 gttctggttc aaggtatctc tagaaaaaga caagactgag ctattctctt tggtggatta    149640
gagatctgct tcaggaggag gaaggttggc cagagttggg cagcactgaa attccacatc    149700
ctcgggctga caccgattct gtaagcttcc ttttttaatat ctcctgaacc aaaatgagtg    149760
tcattagctg gaagttccca attcgggcat ttttctactt taccagtagg gggcaggaga    149820
cactcagaaa aaaattgcaa taagaaatc cagagggcat gaaggctgaa aagatacaaa    149880
gatgtacaaa gctgcttatt gacatggatg gactcataag catttgttag tattcccaga    149940
ttgcaacggg gaggacaaag ggaagagcga gtatttgggc agggcaagga ttttgtagag    150000
acaccatggt cttaatagag cctttaaata ttatgacagc aaatcaagat tctgaaaact    150060
ttttaattca catatagcaa tttgtacatt atagcaaaat ttgcattatt caagaataag    150120
ttacttgtac agtacataaa acaatacata aaaatttgcc aaataccttc tgcctataat    150180
gatacaagat gaatccactt tatgttatca caatgtgctg tatattctaa ccaaacacag    150240
gatgtcagat gtgtccttgt taatatactc gcaagttcct ctagcttgtg ggagatgtta    150300
gagctaacac atttgcagta agggacttag tcctgaatag aaagcatgaa ggaatctcag    150360
gcaaccctca gggaagagtc caaggccttg actttaggtt aagaaactgt tatgtaaaaa    150420
tagtgttctc tggcccaaga ttttaatgat tgctattcct ttttcctacg gtccagaaat    150480
gatcaaaggc agaagattta taccagataa agccatatgg attgctggtc taaaattcaa    150540
ggcaggttag ttgacttaat tctttggtgc tggtgactgt tagtttgtaa aagttcaata    150600
agtcagatga aggaagggat ggtgccggga gctgtcaagc tgtactggtg gggtctgtaa    150660
```

```
ttagagctaa ctggagggat catgatgtct actgtccagt ttggtgttga gccatggctc    150720
tcggtagaag ttgccggctg gggcctggtc aggactggaa ggagagtggt gggatgtgct    150780
gtgcctatgg tgggctagct gcagccagtg gggtgcctgc cccacactgc tgcccacccc    150840
ttcatcagct gattctgctc ccacataaag aaaggtgttg gcttagtgtc acttcttcct    150900
agagccatgg gagttttctg tcagcatgtt tttgagctgt cctggtaact tggacgggaa    150960
gcagtctgga ggtgggtgcc ttccaaatct ctgccacaga a                        151001
```

<210> SEQ ID NO 3
<211> LENGTH: 863
<212> TYPE: DNA
<213> ORGANISM: homo sapiens
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t

<400> SEQUENCE: 3

```
gtctgtcggg gctctctccc cgcccctcc ggatcctggg naagnacggn ggacggggtg      60
gagacaagtg ggccttggcc cccgcacccc tctgcgttcg tgtccgaggc ggcggcgggg    120
gctcccgaac tcccctgaaa tcgtggggct ccatgtggcc tccggcagcg ttccaccctc    180
ccccacctgg ggaagggaag gggtggggag tgcccggccc cgtcccggcc ttcctccttc    240
ccccgccaga cctctccggc gcgcgggtgg tggccgatcc gcattgctgt tcgaggccgc    300
agtggagaag gcgcctgtgg aacatcgagg tcgaaacagt aacaaaggac tgcctcagtc    360
tacgatttct tttgatggaa tctatgcaaa tatgaggatg gttcatatac ttacatcagt    420
tgttggctcc aaatgtgaag tacaagtgaa aaatggaggt atatatgaag gagttttaa    480 aacttacagt ccgaagtgtg atttggtact tgatgccgca catgagaaaa gtacagaatc    540
cagttcgggg ccgaaacgtg aagaaataat ggagagtatt tgttcaaat gttcagactt     600 tgttgtggta cagtttaaag atatggactc cagttatgca aaaagagatg cttttactga    660
ctctgctatc agtgctaaag tgaatggcga acacaaagag aaggaccctg cagcccctgg    720
atgcaggtga actcacagcc aatgagggaa ctggaggctt tgnaaaatga cgtatctaat    780
ggatggaacc caagatatg tttcgtttaa tgaaaaaaat tatggcgcag gggccaccgt     840
tgaaagcagt ttatttcgga tac                                            863
```

<210> SEQ ID NO 4

<400> SEQUENCE: 4

000

<210> SEQ ID NO 5
<211> LENGTH: 27
<212> TYPE: DNA
<213> ORGANISM: Artificial sequence

```
<220> FEATURE:
<223> OTHER INFORMATION: Primer

<400> SEQUENCE: 5
accaaagagt agttaatgga ggtgttc                                              27

<210> SEQ ID NO 6
<211> LENGTH: 19
<212> TYPE: DNA
<213> ORGANISM: Artificial sequence
<220> FEATURE:
<223> OTHER INFORMATION: Primer

<400> SEQUENCE: 6
agaaggtggg cgagaggaa                                                       19

<210> SEQ ID NO 7
<211> LENGTH: 19
<212> TYPE: DNA
<213> ORGANISM: Artificial sequence
<220> FEATURE:
<223> OTHER INFORMATION: Probe

<400> SEQUENCE: 7
ctggccatcg ccttgccca                                                       19

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ccggctcgca cgccgggcgg                                                      20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
catacaccgg ctcgcacgcc                                                      20

<210> SEQ ID NO 13
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 13
ggcttcagcg acatggtgag                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cgacctctgc ccaggccggg                                               20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
tgcatagatt ccatcaaaag                                               20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
aagtatatga accatcctca                                               20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ttcacttgta cttcacattt                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tctgtacttt tctcatgtgc                                               20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
```
ctggattctg tactttttctc                                          20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
ctctccatta tttcttcacg                                           20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
tctttaaact gtaccacaac                                           20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gagtcagtaa aagcatctct                                           20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
cagggctcca ggtccttctc                                           20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gcatcccagg gctccaggtc                                           20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
tcttcattat atcgaaacat                                           20

<210> SEQ ID NO 26
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 26
gctaactggt ttgcccttgc                                                 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
gtatttttct tcctcactcc                                                 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
tgctgtgtat ttttcttcct                                                 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
gaaatctgaa gtgtgagaag                                                 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
cctccattaa ctactctttg                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ggaacacctc cattaactac                                                 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ggcgatggcc agggaacacc                                                 20
```

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
gtagcgagaa ggtgggcgag                                                  20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
agagttggga cctgactggt                                                  20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tggaagagag ttgggacctg                                                  20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ggagctggag aaccatgagc                                                  20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gagacaggag ctggagaacc                                                  20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ttgtgggata caaattctag                                                  20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ggaaccccac tgaccactga                                                   20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tcttgaagcc tggaatcttt                                                   20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aacctaaaat cattcttaaa                                                   20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
agttgatcca tagattcaga                                                   20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ctggtacagt tgctgctgct                                                   20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctgccactgg tacagttgct                                                   20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tttgcattgg gattcaatgt                                                   20

<210> SEQ ID NO 46

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
gaaggctttg gctgagagaa                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
gtagtagaag gctttggctg                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
tgacccacca tagatgggct                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggtattgggt ataaaggttg                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gtcataggta ttgggtataa                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ggatgctgag actgataatg                                              20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
```
acatgaggat gctgagactg                                              20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
aatttgggac atgcatacat                                              20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gtctccttgt tgtatggtaa                                              20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
tgaacaggac tgggtgcagg                                              20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
gactgctgct gtggactggc                                              20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ctgactgtac atgagcctga                                              20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ccattcctga ctgtacatga                                              20

<210> SEQ ID NO 59
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 59
cagttggatg agaaggaacc                                                   20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
catgggcagt tggatgagaa                                                   20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
accgccgggt ggctgtgtcg                                                   20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tttgagcgag ggcggcctgg                                                   20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gctgtagtgc actttgagcg                                                   20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
agactggaat gggctgtagt                                                   20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
gcgctgttgt cgagactgga                                                   20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggaaatgcgc tgttgtcgag                                        20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
ggcttgtact gaagggtgcg                                        20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gtggtgggct tgtactgaag                                        20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
ctgttggtgg tgggcttgta                                        20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
caactgctgt tggtggtggg                                        20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
gccttacaac tgctgttggt                                        20

<210> SEQ ID NO 72
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 72
ttcggttcct ccagggcagc        20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ttctagtttt ctgtgcttcc        20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
aataaataac ttccagtttc        20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gaatcactct tgttacttct        20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
cagcaagaat cactcttgtt        20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
tttataaata ataatccgtc        20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
aagttgaacc actgtagaca        20

```
<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
atcggccacc acccgcgcgc                                                 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
caaagggtta attaggatct                                                 20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
cccaaagggt taattaggat                                                 20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
aggacagtca tttgatttgt                                                 20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
ctttgaggac agtcatttga                                                 20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ctgacagaac aaatgatatg                                                 20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 85
tattgggtat aaaggcttga                                                   20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
ggtattgggt ataaaggctt                                                   20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ctcttttacg catacaggca                                                   20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
aggaaggcca actgagtcct                                                   20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
ggtcagacgg aagcagaacg                                                   20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
ccacctggct gcggcgaagc                                                   20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
gccgttgccg ttgctaccaa                                                   20

<210> SEQ ID NO 92
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 92
ggcccataca ccggctcgca                                                    20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
gcttcagcga catggtgagg                                                    20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
ggacattggc agccgcgggc                                                    20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
gattccatca aaagaaatcg                                                    20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
caactgatgt aagtatatga                                                    20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
ccaaatcaca cttcggactg                                                    20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
```

-continued ctcatgtgcg gcatcaagta                                                  20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
catttgaaca aaatactctc                                                  20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
ctgatagcag agtcagtaaa                                                  20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
gggccactcg agctttgtac                                                  20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
aggaatatat ttattttccc                                                  20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
cccatacgcg gtgaattctg                                                  20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
tggagcccga tccaggctgg                                                  20

<210> SEQ ID NO 105
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 105
agaagtggat cttgatggca                                               20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
ggagaaccat gagcagaggg                                               20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
ggcccttctg aagacatgcg                                               20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cactggatat ggaacccctc                                               20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
gtgggataca aattctaggc                                               20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
actgaccact gatgaccacg                                               20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
ctgggtctat gagttttagg                                               20
```

```
<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
tggaataata ccagcttggg                                                 20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
ggcatggcaa cagcttcagt                                                 20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
taggagatgc agctggaata                                                 20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
gaagcctgga atctttagcc                                                 20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
ccctgcagga gagttctgcc                                                 20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ttcagaagta gaacttggct                                                 20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 118 caatttgtc tttgatcaaa					20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
tgttactaag tattgaaggg					20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
aagtgacctc aggtcccctc					20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
atgttgattt cctaacttgc					20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
gtataaactg gagttggctg					20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
gtgcaaaaca aacaggctga					20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
gactggatac atcatatttg					20

<210> SEQ ID NO 125

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
ggttgcacgc ctgggctcac                                               20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
tcataggtat tgggtataaa                                               20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
ttgattcact ggcatgggcg                                               20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
gatgatgctg gtcttgccgc                                               20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
atcattctag cattaccctg                                               20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
atactaaacc aggctgggcg                                               20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
```
acatgcatac atcgcatgcg                                        20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
tagaaagaag ggcttgtctc                                        20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
cgcatactgc tgagcaaggg                                        20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
tagctgaagg ctgagggtgt                                        20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
caccatgttg gctttgctgc                                        20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
actgggtgca ggatgacttc                                        20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
cgtggtaaat ggctgactgc                                        20

<210> SEQ ID NO 138
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 138
ttggaggcag gtgtcatgga                                                    20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
tggcgcatgg gcagttggat                                                    20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
ctttgagcga gggcggcctg                                                    20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
gtcgagactg gaatgggctg                                                    20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
attcctattg gatgttacaa                                                    20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
atcttccact gcaagtgaac                                                    20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
tatggaatta tggaatagcc                                                    20
```

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
gcaagaatca ctcttgttac					20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
tgtagacagt gatcacctca					20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
ggccaaggcc cacttgtctc					20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
cactgcggcc tcgaacagca					20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
aaattcctca ttttcttttc					20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
gttatagtaa tctgtaatca					20

<210> SEQ ID NO 151
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 151
aggattgtaa aatgatacag                                          20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
gtaggattgt aaaatgatac                                          20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
ttatatatgt aaattatatc                                          20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
aaccactgat ttatacactt                                          20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
ttaaaaacca ctgatttata                                          20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
atatagcact ctgctgtatt                                          20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
taccaagctt gtggcttggg                                          20

```
<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
ttataccaag cttgtggctt                                                    20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
cctcgatgtt ccacaggcgc                                                    20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
gagttcacct gcatccaggg                                                    20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
tccagttccc tcattggctg                                                    20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
ggttccatcc attagatacg                                                    20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
ttaaacgaaa catatctttg                                                    20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 164
gcccctgcgc cataattttt                                             20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
ataaactgct ttcaacggtg                                             20
```